(12) United States Patent
Kriesel

(10) Patent No.: US 8,083,717 B2
(45) Date of Patent: Dec. 27, 2011

(54) TWO PART FLUID DISPENSER WITH TWIN RESERVOIR

(75) Inventor: Marshall S. Kriesel, St. Paul, MN (US)

(73) Assignee: BioQuiddity, Inc., San Francisco, CA (US)

(*) Notice: Subject to any disclaimer, the term of this patent is extended or adjusted under 35 U.S.C. 154(b) by 185 days.

(21) Appl. No.: 12/316,972

(22) Filed: Dec. 17, 2008

(65) Prior Publication Data

US 2010/0056997 A1     Mar. 4, 2010

Related U.S. Application Data

(63) Continuation-in-part of application No. 12/231,556, filed on Sep. 3, 2008.

(51) Int. Cl.
    *A61M 5/20* (2006.01)
(52) U.S. Cl. .................................. 604/134
(58) Field of Classification Search .......... 604/85, 604/86, 191, 156, 157, 134–139, 246, 207, 604/212, 216, 132, 133, 153; 417/472, 473
See application file for complete search history.

(56) References Cited

U.S. PATENT DOCUMENTS

| | | | |
|---|---|---|---|
| 2,236,084 A | 3/1941 | Brown | |
| 3,884,228 A | 5/1975 | Hahn | |
| 5,009,251 A | 4/1991 | Pike et al. | |
| 5,380,287 A | 1/1995 | Kikuchi et al. | |
| 5,632,315 A | 5/1997 | Rose | |
| 6,056,716 A | 5/2000 | D'Antonio et al. | |
| 6,236,624 B1 | 5/2001 | Kriesel et al. | |
| 6,355,019 B1 | 3/2002 | Kriesel et al. | |
| 6,416,495 B1 | 7/2002 | Kriesel et al. | |
| 7,220,245 B2 * | 5/2007 | Kriesel | 604/134 |
| 2005/0033232 A1 * | 2/2005 | Kriesel | 604/131 |
| 2005/0038387 A1 * | 2/2005 | Kriesel et al. | 604/133 |
| 2006/0206052 A1 * | 9/2006 | Kriesel et al. | 604/82 |
| 2008/0027376 A1 * | 1/2008 | Kriesel et al. | 604/84 |
| 2008/0319385 A1 * | 12/2008 | Kriesel et al. | 604/88 |

* cited by examiner

*Primary Examiner* — Nicholas D Lucchesi
*Assistant Examiner* — Jenna Zhang
(74) *Attorney, Agent, or Firm* — James E. Brunton

(57) ABSTRACT

A dispensing device for dispensing medicaments to a patient that includes first, second and third stand-alone, inter-connectable assemblies. The first of these assemblies comprises a fluid delivery and control assembly that includes a novel flow control assembly that functions to control the flow of medicinal fluid from the fluid reservoirs of the first and second assemblies of the invention toward the patient via a plurality of fluid flow control passageways. The second and third stand-alone reservoir defining components, which are interconnected with the fluid and delivery control component, each include an integrally formed, hermetically sealed collapsible container and a spring for controllably collapsing the container.

13 Claims, 50 Drawing Sheets

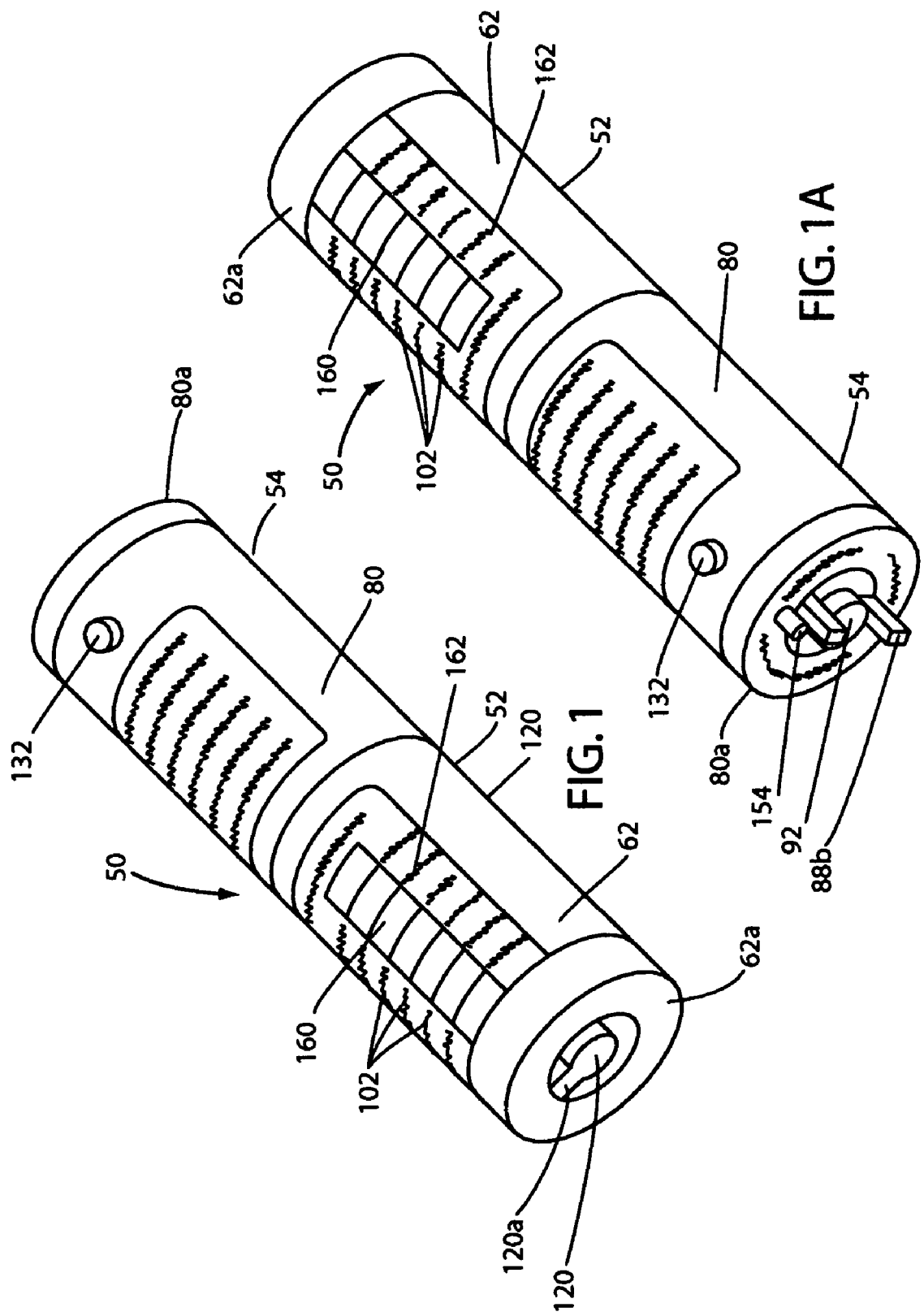

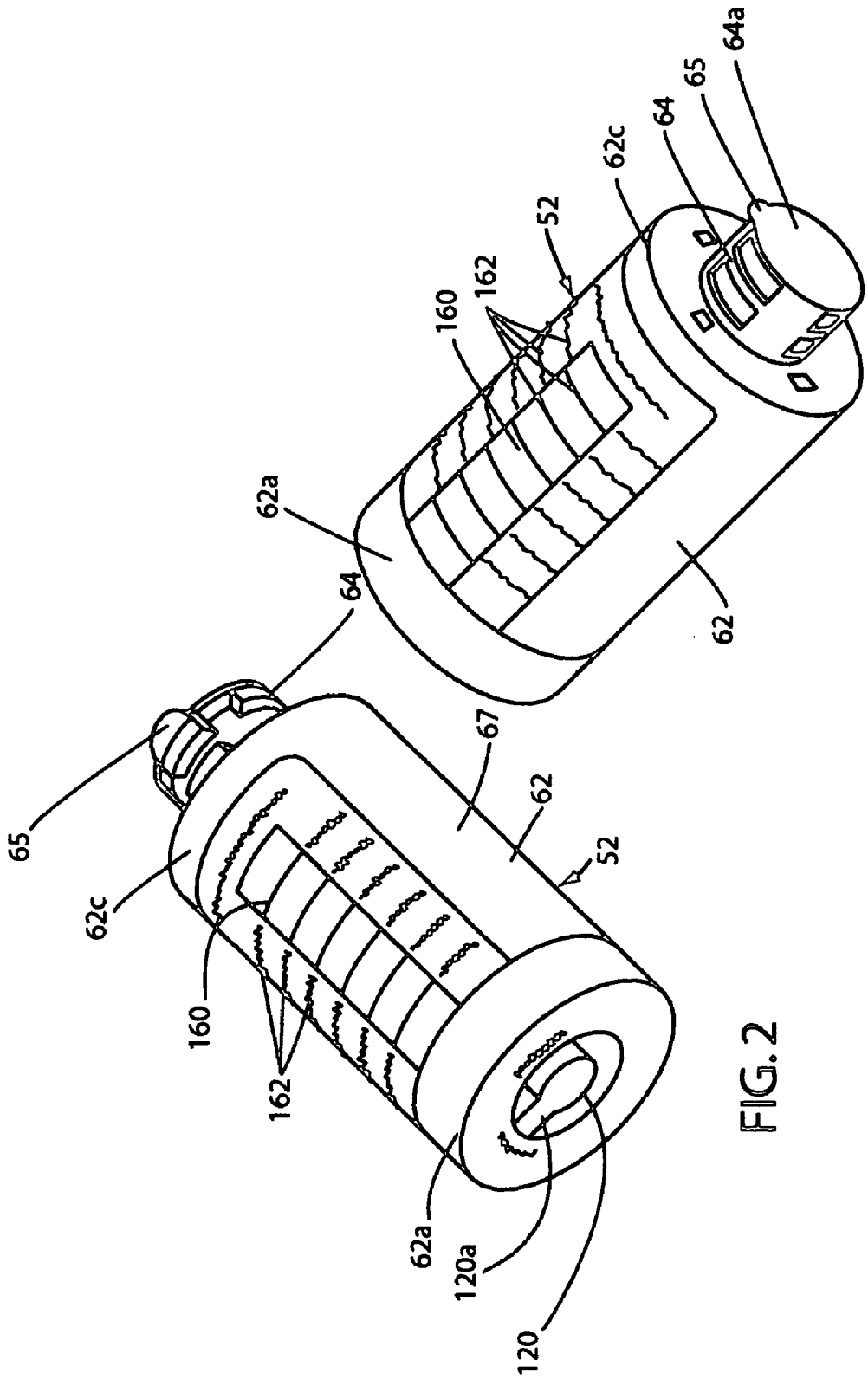

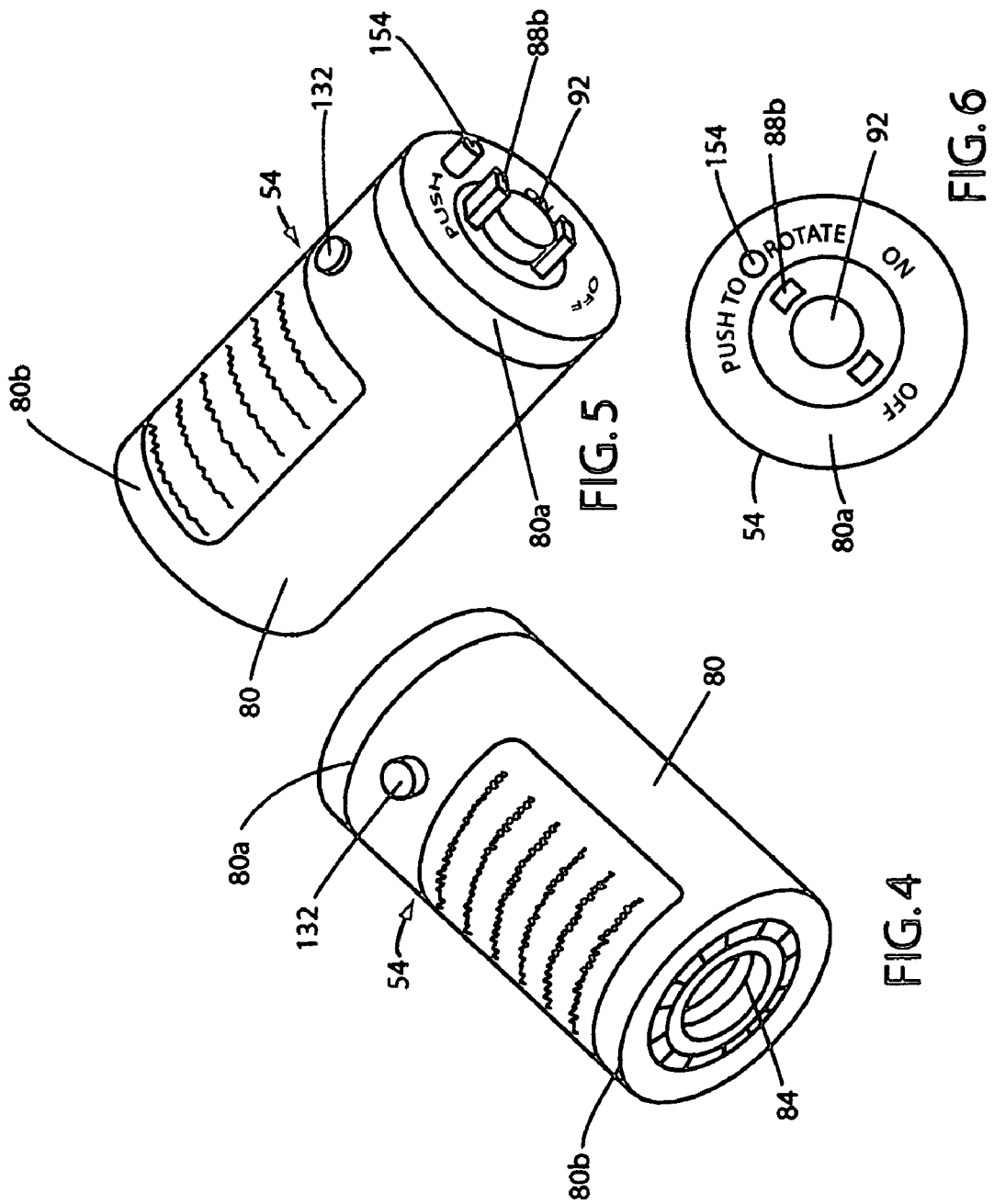

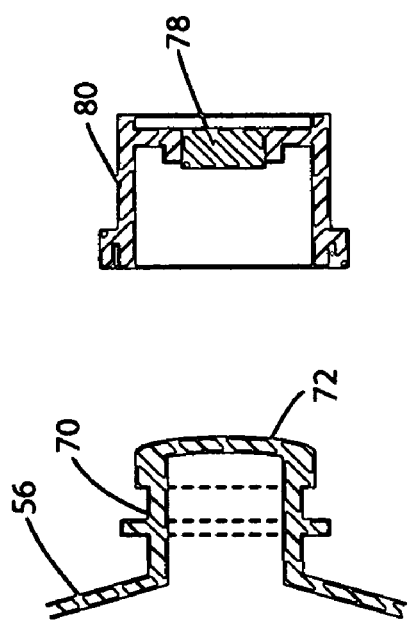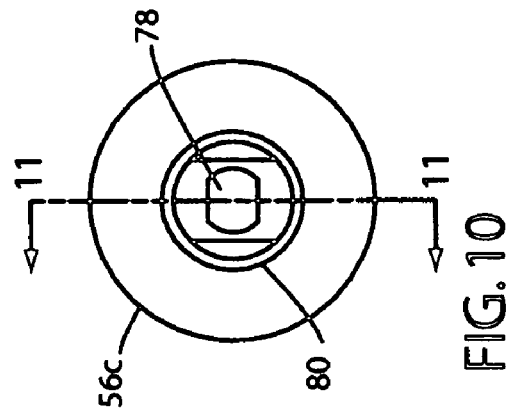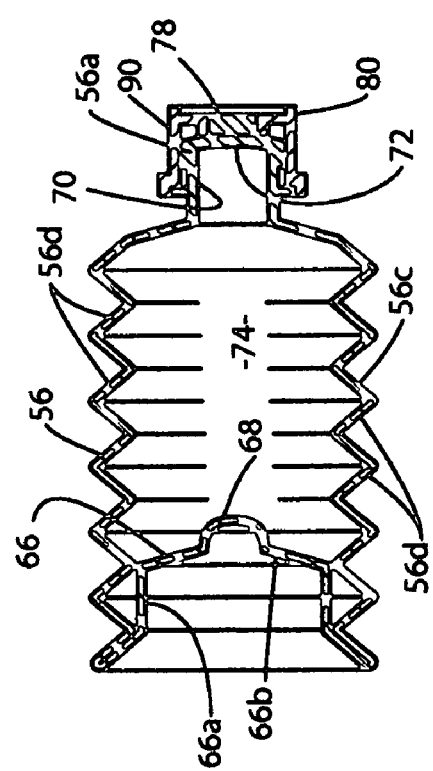
FIG. 10
FIG. 12
FIG. 11

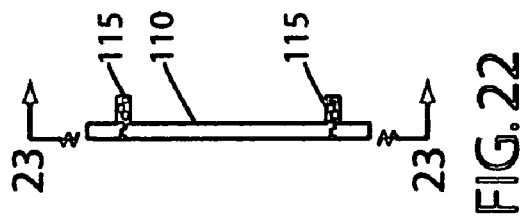
FIG. 22
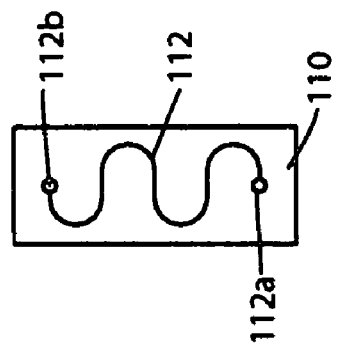
FIG. 23
FIG. 20
FIG. 21
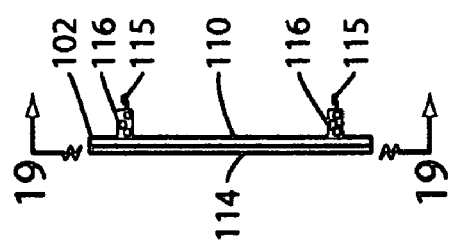
FIG. 18
FIG. 19

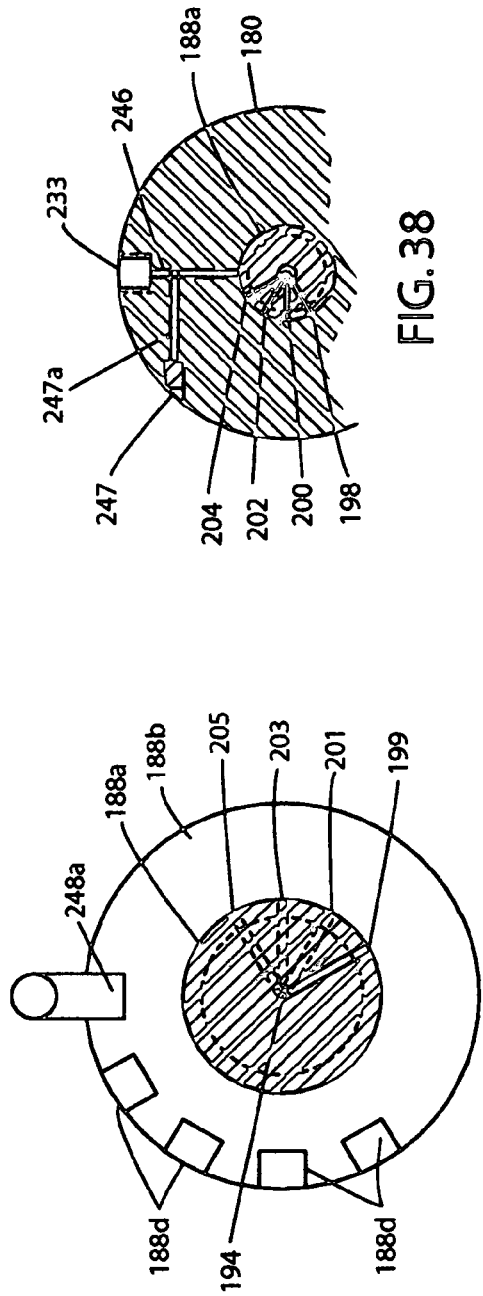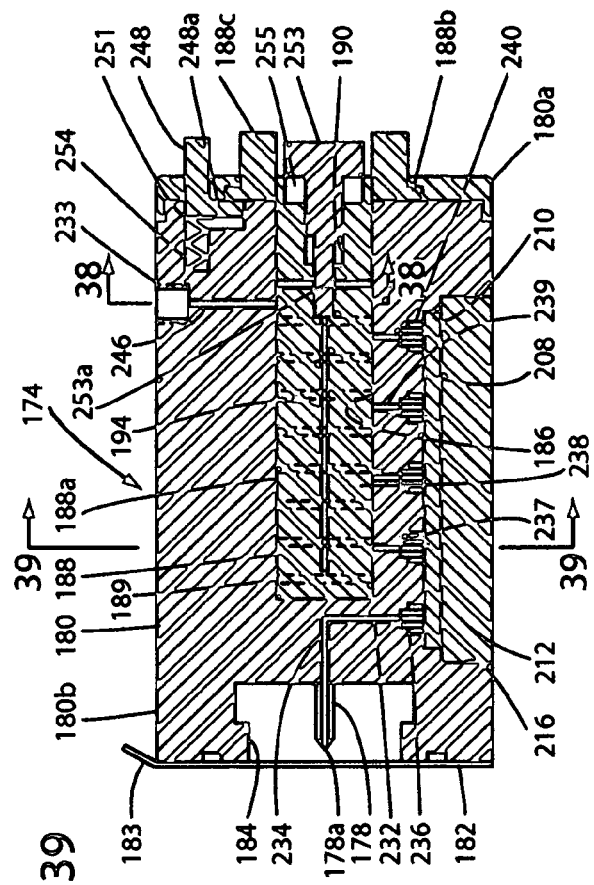

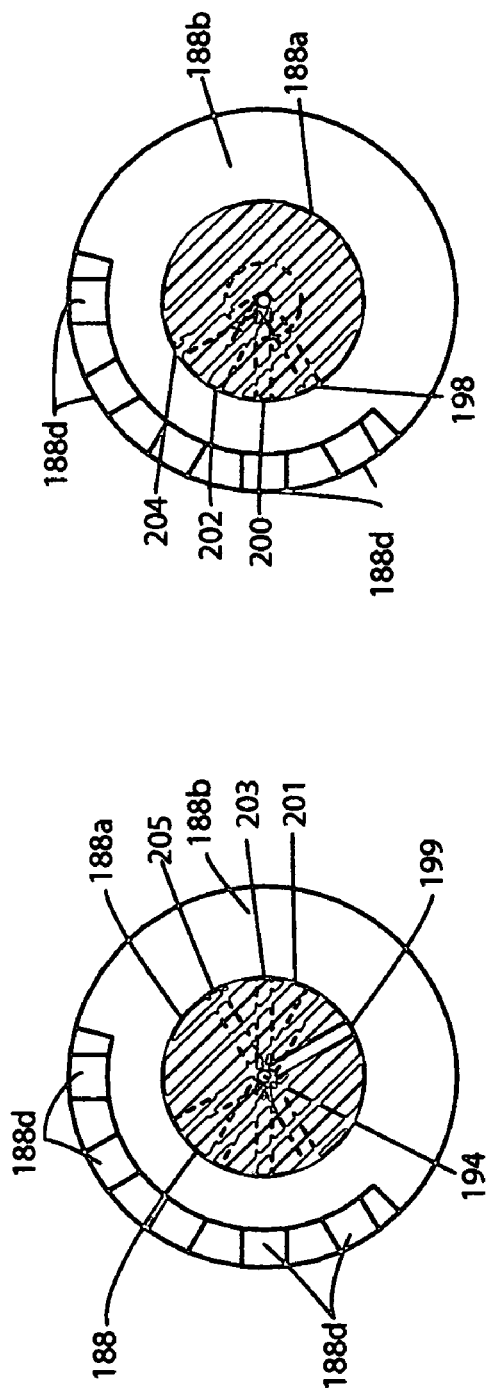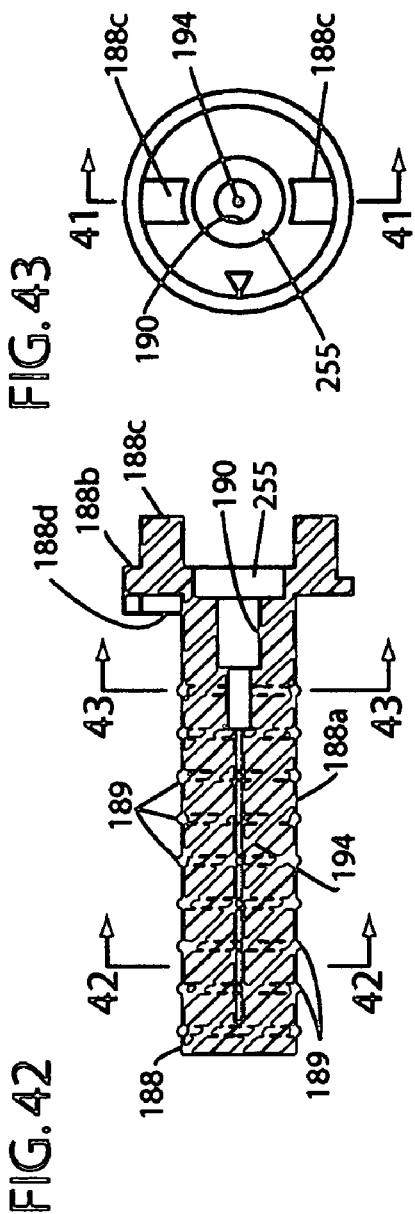

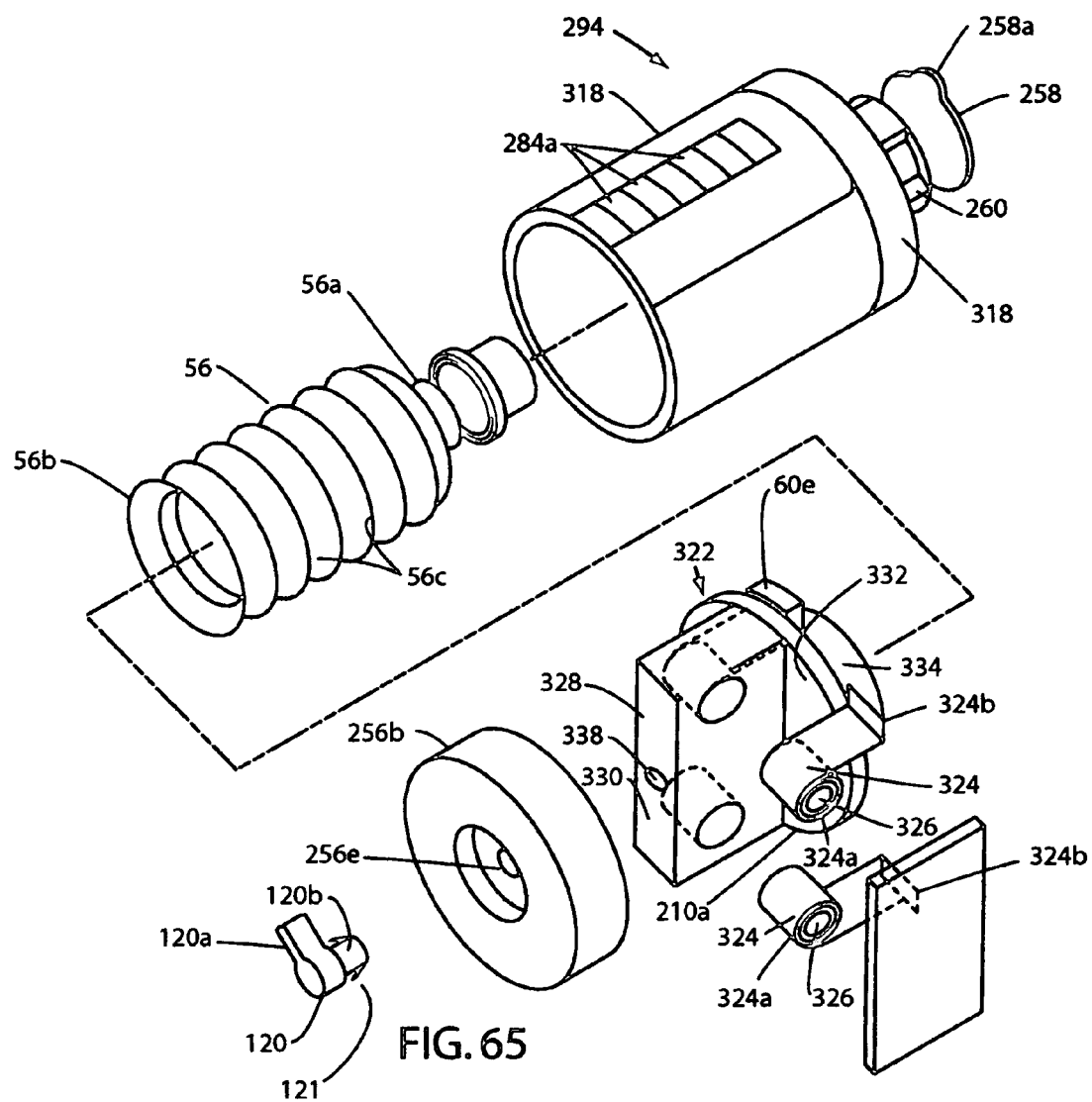

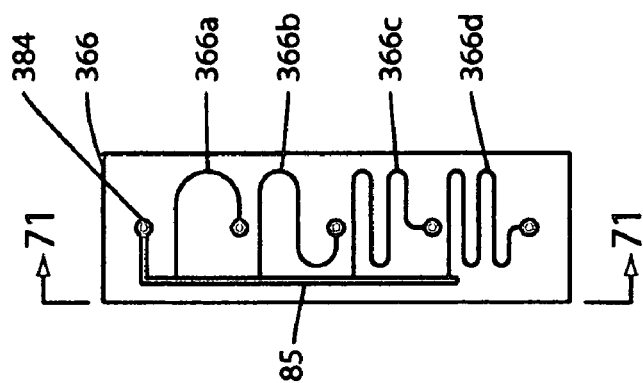
FIG. 70
FIG. 71
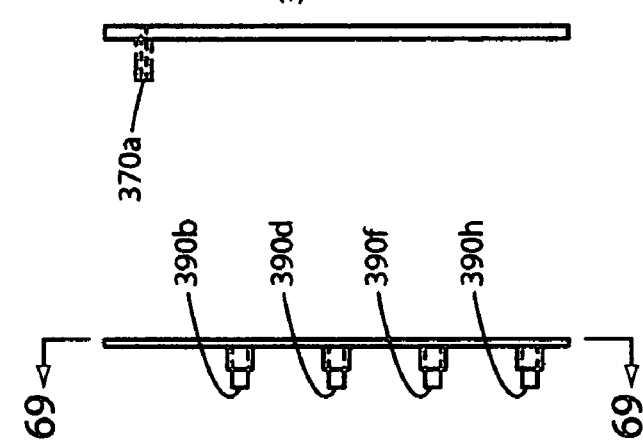
FIG. 69
FIG. 68
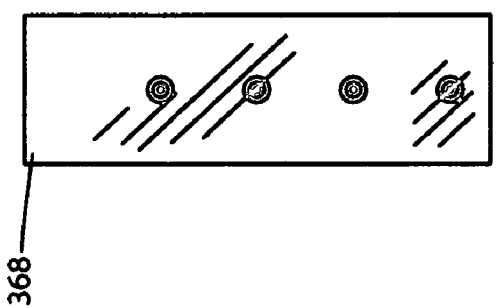
FIG. 67
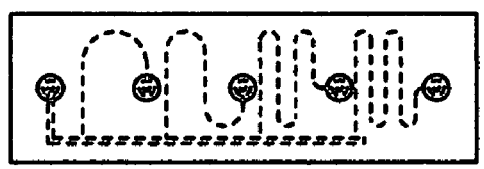
FIG. 66

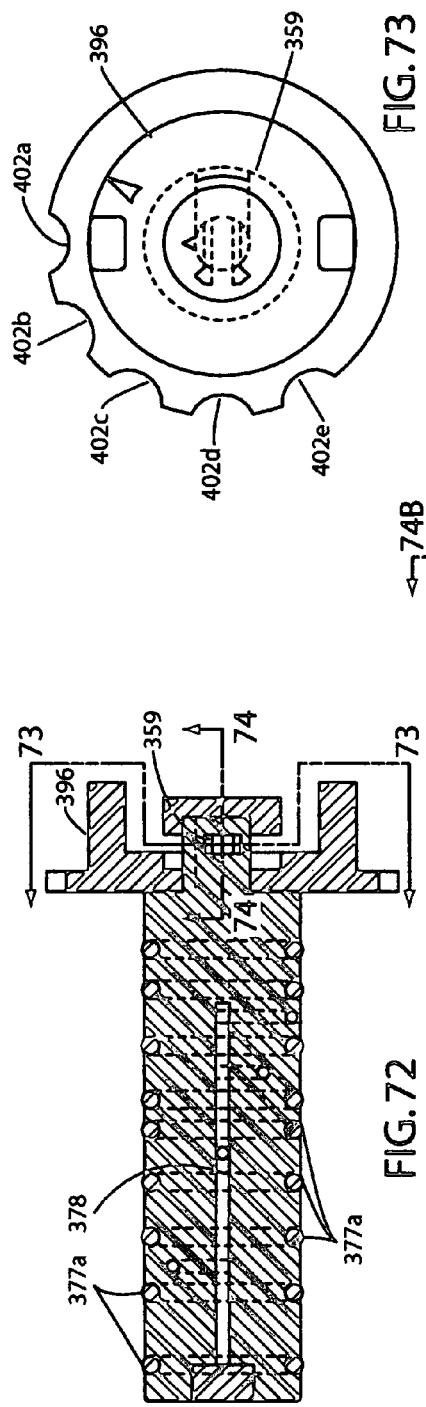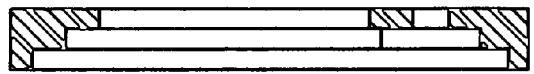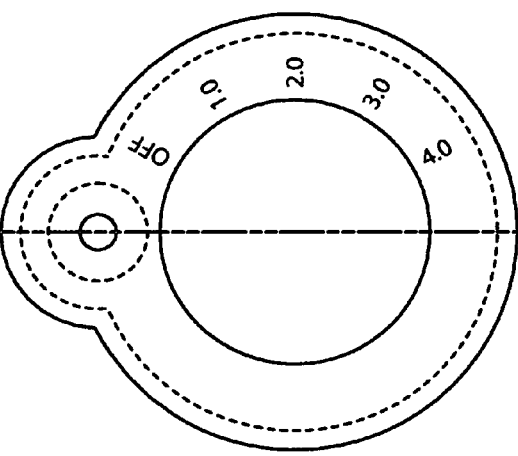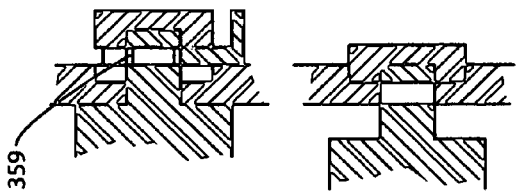

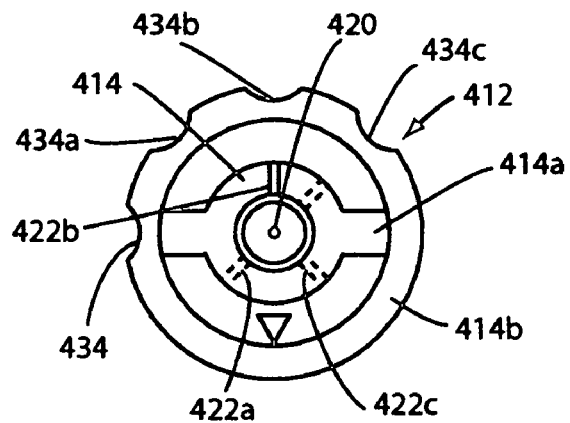
FIG. 88
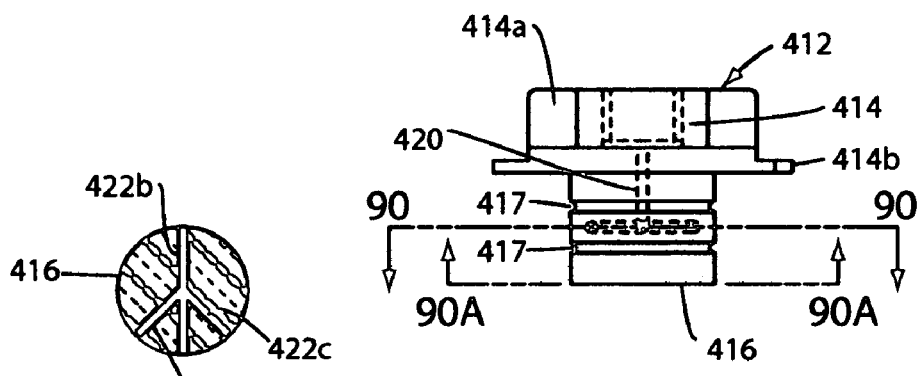
FIG. 90
FIG. 89
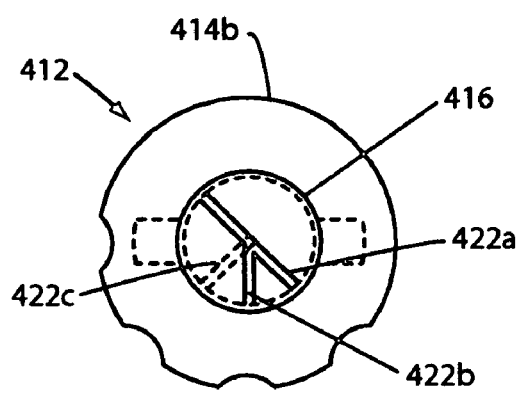
FIG. 90A

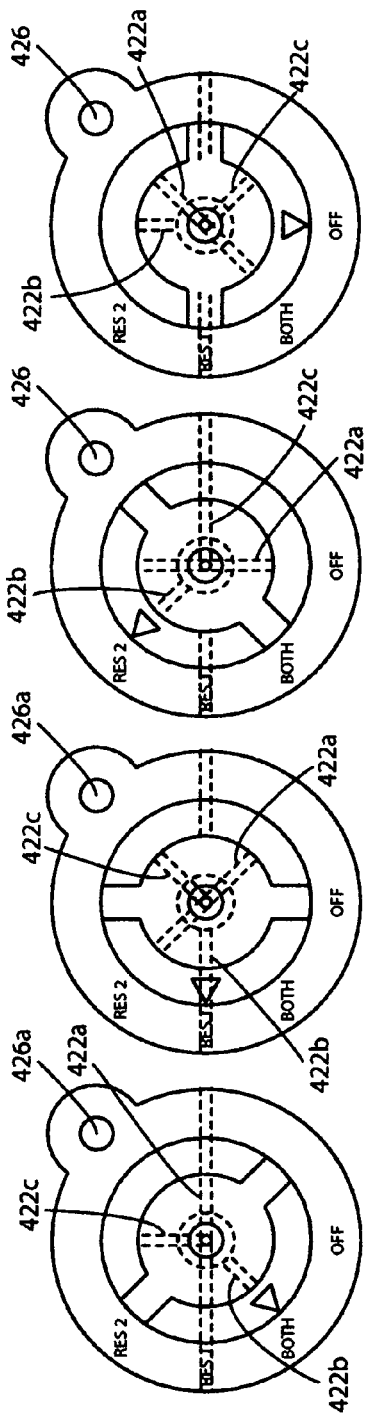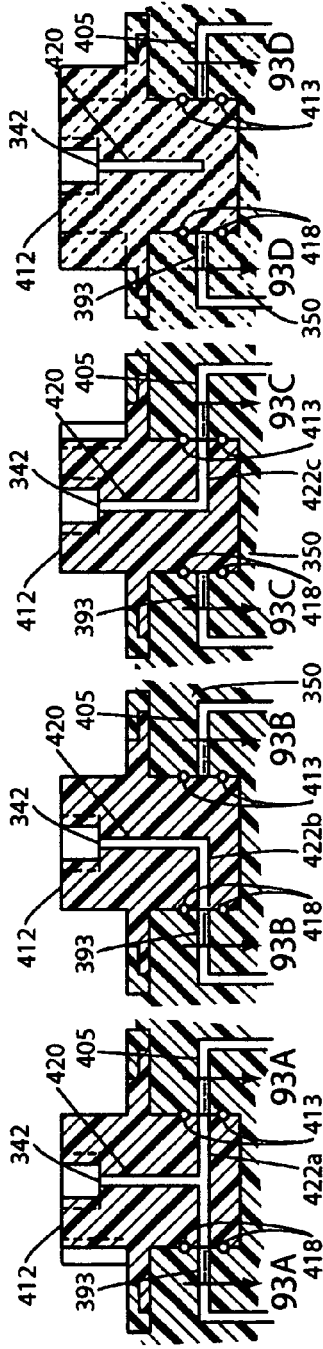

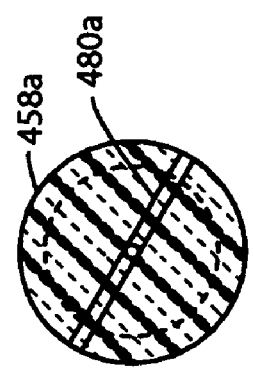
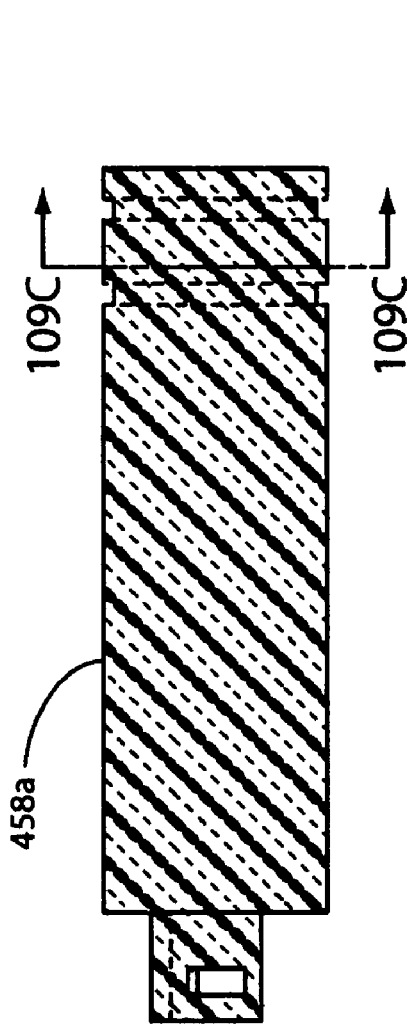
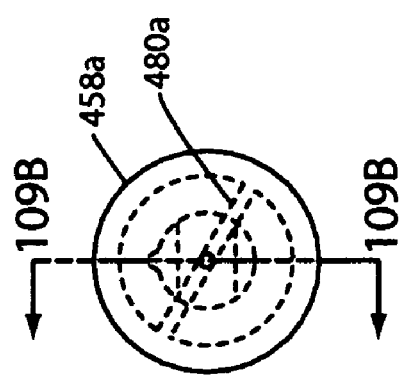
FIG. 109C
FIG. 109B
FIG. 109A

US 8,083,717 B2

TWO PART FLUID DISPENSER WITH TWIN RESERVOIR

This is a Continuation-In-Part Application of co-pending U.S. application Ser. No. 12/231,556 filed Sep. 3, 2008.

BACKGROUND OF THE INVENTION

1. Field of the Invention

The present invention relates generally to fluid dispensing devices. More particularly, the invention concerns a two part medicament dispenser for dispensing medicinal fluids to ambulatory patients that uniquely enables sterilization of the fluid flow channels without adversely affecting the medicament contained within the reservoir of the apparatus.

2. Discussion of the Prior Art

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, bio-pharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

A more recent fluid dispensing apparatus invented by one of the named inventors of the present application is disclosed in U.S. Pat. No. 7,220,245. This apparatus comprises a compact fluid dispenser for use in controllably dispensing fluid medicaments, such as antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

SUMMARY OF THE INVENTION

By way of brief summary, one form of the dispensing device of the present invention for dispensing medicaments to a patient comprises first and second stand-alone, inter-connectable assemblies. The first of these assemblies comprises a fluid reservoir assembly that houses a fluid reservoir defining component while the second assembly comprises a fluid delivery and control assembly that includes a novel flow control means that functions to control the flow of medicinal fluid from the fluid reservoir of the first assembly toward the patient via a plurality of fluid flow control passageways. A novel and highly important feature of the apparatus of the present invention resides in the fact that, because the stand-alone fluid delivery and control assembly is initially totally separate from the fluid reservoir assembly of the apparatus, the fluid flow passageways of the fluid delivery and control assembly can be effectively sterilized using conventional gamma ray sterilization techniques without adversely affecting the medicament contained within the fluid reservoir of the apparatus.

With the forgoing in mind, it is an object of the present invention to provide a novel, two-part fluid dispensing apparatus for use in controllably dispensing fluid medicaments, such as antibiotics, anesthetics, analgesics, and like medicinal agents; at a uniform rate in which the fluid flow passageways of the apparatus can be effectively sterilized using conventional gamma ray sterilization techniques without adversely affecting the medicament contained within the fluid reservoir of the apparatus.

Another object of the invention is to provide a fluid dispensing apparatus of the aforementioned character dispenser of simple construction and one that can be used in the home care environment with a minimum amount of training.

Another object of the invention is to allow infusion therapy to be initiated quickly at the point of care without the assistance of a medical professional.

Another object of the invention is to provide a dispensing device for dispensing medicaments to a patient that includes first, second and third stand-alone, inter-connectable assemblies. The first of these assemblies comprises a fluid delivery and control assembly that includes a novel flow control assembly that functions to control the flow of medicinal fluid from the fluid reservoirs of the first and second assemblies of the invention toward the patient via a plurality of fluid flow control passageways. The second and third stand-alone reservoir defining components, which are interconnected with the fluid and delivery control component, each include an integrally formed, hermetically sealed collapsible container and a spring for controllably collapsing the container.

BRIEF DESCRIPTION OF THE DRAWINGS

FIG. 1 is a generally perspective rear view of one form of the two-part fluid delivery system of the present invention.

FIG. 1A is a generally perspective front view of the two-part fluid delivery system illustrated in FIG. 1.

FIG. 2 is a generally perspective rear view of one form of the first stand-alone component of the invention that comprises the fluid reservoir assembly that houses a fluid reservoir defining component.

FIG. 3 is a generally perspective front view of the first stand-alone component of the invention shown in FIG. 2.

FIG. 4 is a generally perspective rear view of one form of the second stand-alone component of the invention that comprises a fluid delivery and control assembly that includes a novel flow control means that functions to control the flow of medicinal fluid from the fluid reservoir of the first stand-alone component toward the patient.

FIG. 5 is a generally perspective front view of the second stand-alone component of the invention shown in FIG. 4.

FIG. 6 is a front view of the second stand-alone component of the invention shown in FIG. 5.

FIG. 10 is a front view of one form of the collapsible fluid reservoir of the first stand-alone component of the invention.

FIG. 11 is a cross-sectional view taken along lines 11-11 of FIG. 10.

FIG. 12 is an enlarged, fragmentary cross-sectional view of the forward portion of the fluid reservoir shown in FIG. 11.

FIG. 18 is a side elevational view of one form of the rate control plate assembly of the second stand-alone component that includes a rate control plate and the rate control plate cover.

FIG. 19 is a view taken along lines 19-19 of FIG. 18.

FIG. 20 is a side elevational view of one form of the rate control plate cover of the second stand-alone component.

FIG. 21 is a view taken along lines 21-21 of FIG. 20.

FIG. 22 is a side elevational view of the rate control plate of the rate control plate assembly shown in FIG. 18.

FIG. 23 is a view taken along lines 23-23 of FIG. 22.

FIG. 37 is a longitudinal cross-sectional view of the alternate form of the second stand-alone component shown in FIG. 31.

FIG. 38 is a cross-sectional view taken along lines 38-38 of FIG. 37.

FIG. 39 is a cross-sectional view taken along lines 39-39 of FIG. 37.

FIG. 40 is a front view of the rate control housing of the alternate second stand-alone component.

FIG. 41 is a cross-sectional view of the rate control housing taken along lines 41-41 of FIG. 40.

FIG. 42 is an enlarged cross-sectional view taken along lines 42-42 of FIG. 41.

FIG. 43 is an enlarged cross-sectional view taken along lines 43-43 of FIG. 41.

FIG. 65 is a greatly enlarged, generally perspective, exploded view of a portion of the first stand-alone component of the invention shown in FIG. 59 that embodies a stored energy means in the form of a constant force spring.

FIG. 66 is a side elevational view of one form of the rate control chip assemblies of the invention.

FIG. 67 is a view taken along lines 67-67 of FIG. 66.

FIG. 68 is a top plan view of one form of the rate control chip cover of one of the rate control chip assemblies of the invention.

FIG. 69 is a view taken along lines 69-69 of FIG. 68.

FIG. 70 is a front view of one form of the rate control chip of one of the rate control chip assemblies of the invention.

FIG. 71 is a view taken along lines 71-71 of FIG. 70.

FIG. 72 is a greatly enlarged cross-sectional view of the rate control shaft assemblies of one of the stand-alone unitary fluid reservoir assemblies of the invention.

FIG. 73 is a view taken along lines 73-73 of FIG. 72.

FIG. 74 is a cross-sectional view taken along lines 74-74 of FIG. 72.

FIG. 74A is a front view of the selector knob retaining cover of the alternate form of the apparatus shown in FIG. 49.

FIG. 74B is a cross-sectional view taken along lines 74B-74B of FIG. 74A.

FIG. 88 is a top plan view of the reservoir selector knob of the invention.

FIG. 89 is a cross-sectional view taken along lines 89-89 of FIG. 88.

FIG. 90 is a cross-sectional view taken along lines 90-90 of FIG. 89.

FIG. 90A is a view taken along lines 90A-90A of FIG. 89.

FIG. 91A is a view illustrating the position of the reservoir selector knob when fluid can flow from both of the reservoirs of the unitary fluid reservoir assemblies toward the administration set.

FIG. 91B is a view illustrating the position of the reservoir selector knob when fluid can flow from the reservoir of one of the unitary fluid reservoir assemblies toward the administration set.

FIG. 91C is a view illustrating the position of the reservoir selector knob when fluid can flow from the reservoir of the other of the unitary fluid reservoir assemblies toward the administration set.

FIG. 91D is a view illustrating the position of the reservoir selector knob when fluid can flow from neither of the reservoirs of the unitary fluid reservoir assemblies toward the administration set.

FIG. 92A is a cross-sectional view of the assembly shown in FIG. 91A.

FIG. 92B is a cross-sectional view of the assembly shown in FIG. 91B.

FIG. 92C is a cross-sectional view of the assembly shown in FIG. 91C.

FIG. 92D is a cross-sectional view of the assembly shown in FIG. 91D.

FIG. 93A is a cross-sectional view taken along lines 93A-93A of FIG. 92A.

FIG. 93B is a cross-sectional view taken along lines 93B-93B of FIG. 92B.

FIG. 93C is a cross-sectional view taken along lines 93C-93C in 92C.

FIG. 93D is a cross-sectional view taken along lines 93D-93D in 92D.

FIG. 99 is a view taken along lines 99-99 of FIG. 98.

FIG. 100 is a top plan view of the stand-alone fluid delivery and control assembly of the alternate form of the fluid delivery system shown in FIG. 94.

FIG. 101 is a view taken along lines 101-101 of FIG. 100.

FIG. 102 is a cross-sectional view taken along lines 102-102 of FIG. 101.

FIG. 103 is a view taken along lines 103-103 of FIG. 102.

FIG. 104 is a side elevational view of one form of the fixed rate control chip assemblies of the invention.

FIG. 105 is a view taken along lines 105-105 of FIG. 104.

FIG. 106 is a front view of the form of the rate control chip cover of the rate control chip assembly shown in FIG. 104.

FIG. 107 is a view taken along lines 107-107 of FIG. 106.

FIG. 108 is a top plan view of the rate control chip of the assembly shown in FIG. 104.

FIG. 109 is a view taken along lines 109-109 of FIG. 108.

FIG. 109A is a greatly enlarged end view of one of the rate control shafts of one of the stand-alone unitary fluid reservoir assemblies of the invention.

Figure 109:
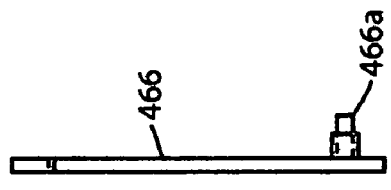
Figure 108:
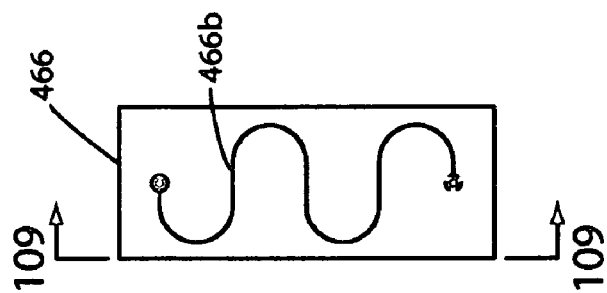
Figure 107:
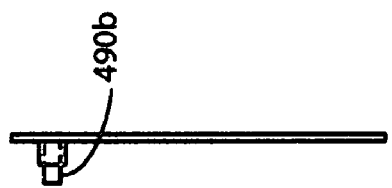
Figure 106:
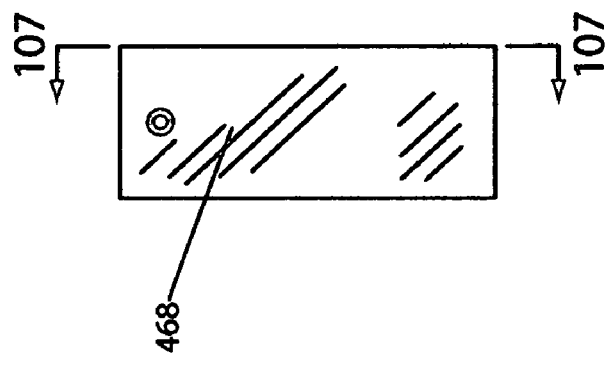

FIG. 109B is a cross-sectional view taken along lines 109B-109B of FIG. 109A.

FIG. 109C is a cross-sectional view taken along lines 109C-109C of FIG. 109B.

Figure 110:
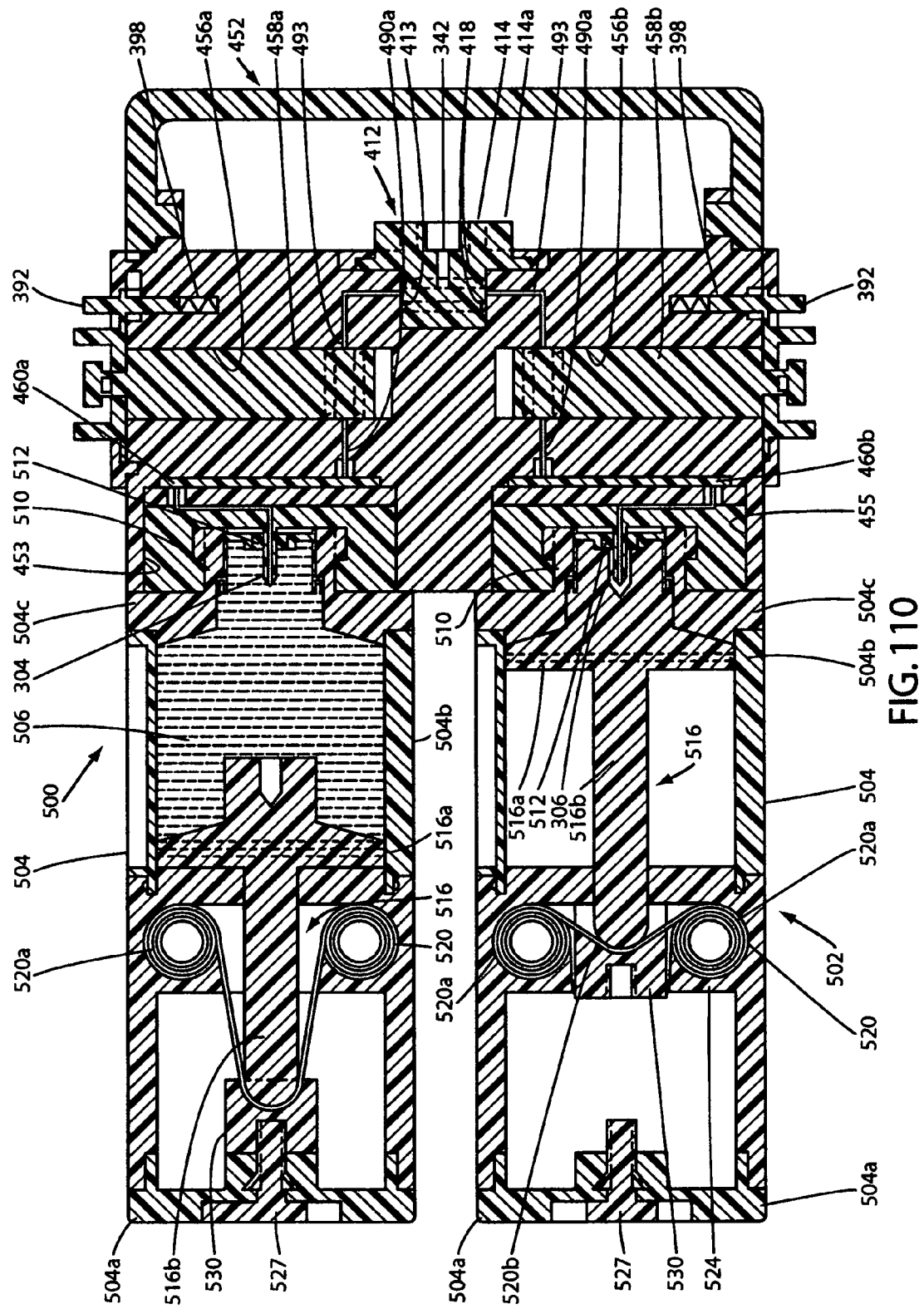

FIG. 110 is a longitudinal cross-sectional view of yet another form of the fluid delivery system of the present invention, wherein the first and second stand-alone unitary fluid reservoir assembly components of the invention have been operably interconnected with the fluid delivery and control assembly.

Figure 111:
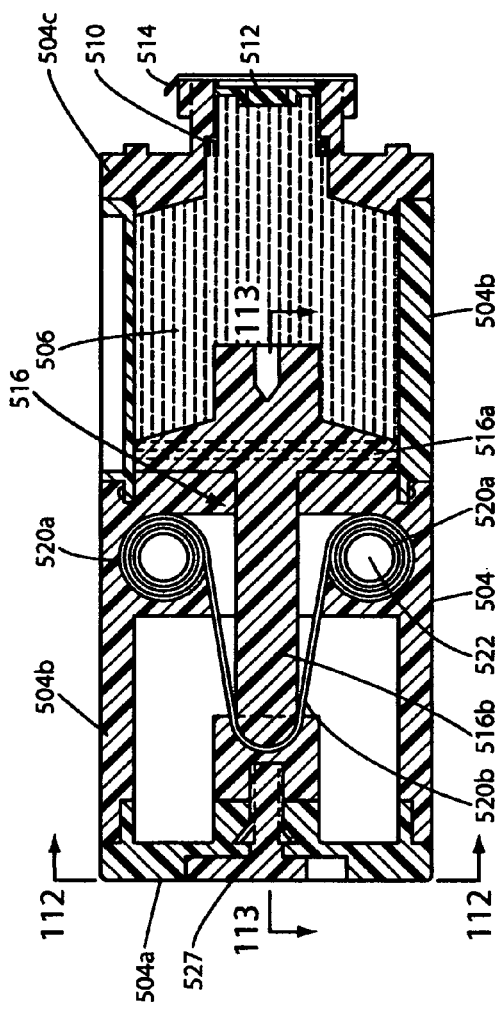

FIG. 111 is a longitudinal cross-sectional view of one of the stand-alone unitary fluid reservoir assembly components of the form of the invention shown in FIG. 110.

Figure 112:
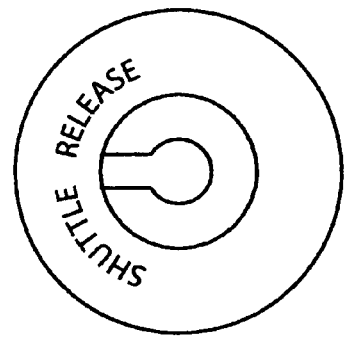

FIG. 112 is a view taken along lines 112-112 of FIG. 111.

Figure 113:
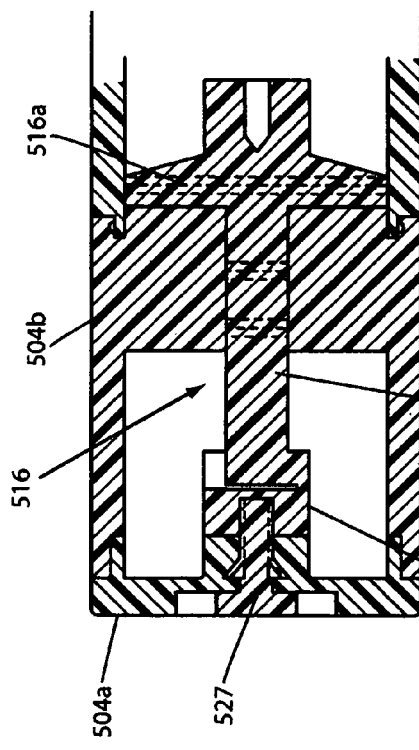

FIG. 113 is a cross-sectional view taken along lines 113-113 of FIG. 111.

Figure 114:

FIG. 114 is a cross-sectional view taken of one form of the dispenser cap of the invention for removably covering the neck of the unitary fluid reservoir assembly components.

DESCRIPTION OF THE INVENTION

Definitions

As Used Herein the Following Terms Mean

Unitary Container
A closed container formed from a single component.
Continuous/Uninterrupted Wall.
A wall having no break in uniformity or continuity.
Hermetically Sealed Container
A container that is designed and intended to be secure against the entry of microorganisms and to maintain the safety and quality of its contents after pressurizing.
Aseptic Processing
The term 'aseptic processing' as it is applied in the pharmaceutical industry refers to the assembly of sterilized components and product in a specialized clean environment.
Sterile Product
A sterile product is one that is free from all living organisms, whether in a vegetative or spore state.

Blow-Fill-Seal Process
The concept of aseptic blow-fill-seal (BFS) is that a container is formed, filled, and sealed as a unitary container in a continuous manner without human intervention in a sterile enclosed area inside a machine. The process is multi-stepped; pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.
Integrally Formed
An article of one-piece construction, or several parts that are rigidly secured together, and smoothly continuous in form and that any such components making up the part have been then rendered inseparable.
Frangible
An article, item or object that is capable of being ruptured or broken, but does not necessarily imply any inherent materials weakness. A material object under load that demonstrates a mechanical strain rate deformation behavior leading to disintegration.
Spring
A mechanical element that can be deformed by a mechanical force such that the deformation is directly proportional to the force or torque applied to it. An elastic machine component able to deflect under load in a prescribed manner and able to recover its initial shape when unloaded. The combination of force and displacement in a deflected spring is energy which may be stored when moving loads are being arrested.
Variable Force Spring
The general class of variable force springs are those that provide a varying force at varying lengths of distention. Contrary to standard coil springs that display stress-strain properties in accordance with Hook's Law, variable force springs may have a variety of linear or non-linear relationships between spring displacement and the force provided.

As used herein, variable force spring includes an elongated, pre-stressed strip of spring material that may be metal, a polymer, a plastic, or a composite material with built-in curvature so that, like the conventional constant force spring, each turn of the strip wraps tightly on its inner neighbor. Uniquely, in a variable force spring the elongated pre-stressed strip of spring material exhibits a cross-sectional mass that varies along said length. This variation in cross-sectional mass along the length of the spring can be achieved in various ways, as for example, by varying the width of the pre-stressed strip along its length, by providing spaced-apart apertures in the pre-stressed strip along its length, or by otherwise changing the amount of material in a pre-determined way so as to generate the desired stress-strain properties. Alternatively, the term "variable force spring" also refers to extension type springs where the wound bands can be coiled to predetermined varying degrees of tightness. Accordingly, similar to a variable force spring with varying amounts of material, variable force springs with a variation of coil tightness can produce highly specific and desirable linear and non-linear force-distention curves to meet the requirements of the invention described herein.
Collapsible
To cause to fold, break down, or fall down or inward or as in bent-over or doubled-up so that one part lies on another.
Collapsible Container
A dispensing apparatus in which one or more walls of the container are made of a material which will deform (collapse) when pressure is applied thereto; or a dispensing apparatus having a collapsible or telescoping wall structure.

Constant Force Spring

Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force, the same as a common extension spring but at a nearly constant (zero) rate. The constant-force spring is well suited to long extensions with no load build-up. In use, the spring is usually mounted with the inner diameter tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.

Figure 8:
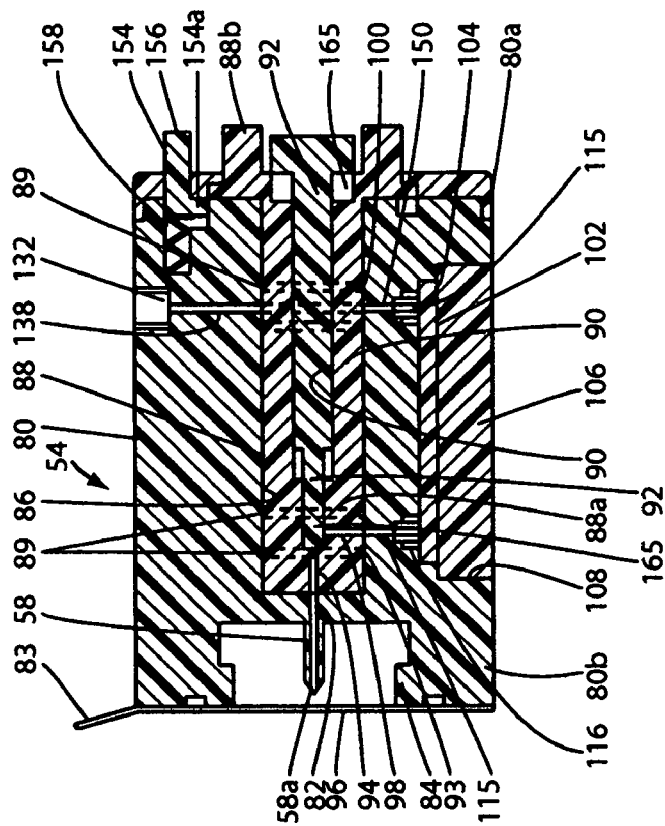
FIG. 8 is a longitudinal cross-sectional view of the second stand-alone component shown in FIGS. 4, 5 and 6 of the drawings.
Figure 7:
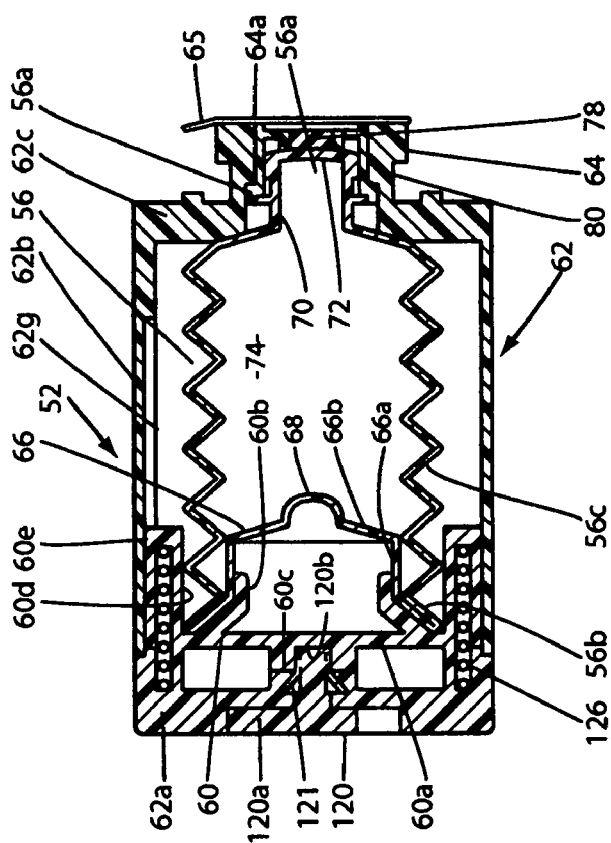
FIG. 7 is a longitudinal cross-sectional view of the first stand-alone component of the invention shown in FIGS. 2 and 3 of the drawings.

Referring to the drawings and particularly to FIGS. 1 through 8, one form of the two part fluid dispensing apparatus of the present invention for dispensing medicaments is there shown. The dispensing apparatus, which is generally designated in FIGS. 1, 1A and 8A by the numeral 50, comprises two stand-alone, interconnectable assemblies 52 and 54. As best seen in FIG. 7 of the drawings, assembly 52 comprises a fluid reservoir assembly that houses a fluid reservoir defining component 56 having an outlet 56a. As illustrated in FIG. 8 of the drawings, assembly 54 comprises a fluid delivery and control assembly that includes a penetrating member 58 and a novel fluid flow control means that functions to control the flow of medicinal fluid toward the patient.

Figure 16:
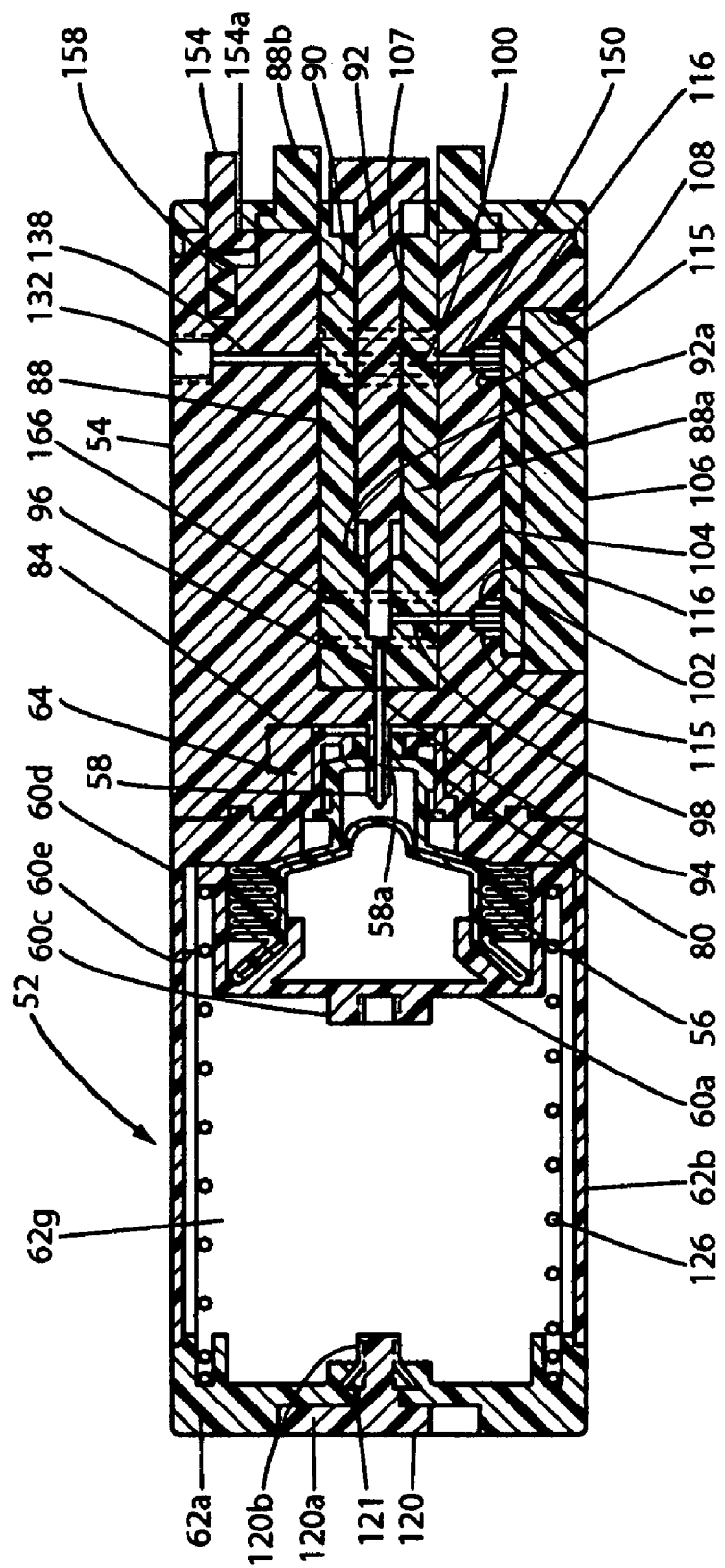
FIG. 16 is a longitudinal cross-sectional view of the fluid dispensing apparatus of the invention shown in FIG. 1, wherein the first and second stand-alone components of the invention have been operably interconnected.

Considering first the unitary fluid reservoir assembly 52, in addition to the reservoir defining component 56, this assembly includes a carriage 60 and a stored energy means that is operably associated with the carriage for moving the carriage between a first retracted position shown in FIG. 7 and a second advanced position shown in FIG. 16. As best seen by referring to FIG. 7, carriage 60 includes a base 60a, a reservoir receiving flange 60b, a carriage locking member receiving protuberance 60c and a stored energy means receiving skirt 60d which receives the novel stored energy means of the invention. Carriage 60 is releasably locked in its first position by a novel carriage locking means, the character of which will be described in the paragraphs which follow.

The reservoir defining component 56, the carriage 60 and a stored energy means are all housed within a generally cylindrically shaped housing 62 that includes a base 62a, an outer wall 62b and a front wall 62c. Connected to front wall 62c is an externally threaded connector neck 64. Connector neck 64 is closed by a first cover shown here as a first sterile barrier 64a that is removably connected to the connector neck in the manner shown in FIG. 7 of the drawings. Sterile barrier 64a, which includes a pull tab 65, here comprises a thin membrane constructed from any suitable polymer.

As best seen in FIG. 11, reservoir defining component 56 here comprises an integrally formed, hermetically sealed container that includes a front portion 56a, a rear portion 56b and a collapsible accordion-like, continuous, uninterrupted side wall 56c that interconnects the front and rear portion of the container. As illustrated in the drawings, the accordion like side wall 56c comprises a multiplicity of adjacent generally "V" shaped interconnected folds, 56d. Rear portion 56b of the container includes an inwardly extending ullage segment 66 having a side wall 66a and an end wall 66b. As illustrated in FIGS. 7 and 11, end wall 66b includes a generally hemispherical shaped protuberance 68. Front portion 56a of the container includes an integrally formed neck 70 having a closure wall 72. Front portion 56a, rear portion 56b and side wall 56c cooperate to define the fluid reservoir 74 of the fluid reservoir assembly 52.

Reservoir defining component 56 is constructed in accordance with aseptic blow-fill seal manufacturing techniques, the character of which is well understood by those skilled in the art. Basically, this technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding and then filling the molded container in a sterile fashion. Following the molding, filling and sealing of the container, it is sterilized at high temperature in a manner well understood by those skilled in the art. Unlike chemical or gamma ray sterilization, this temperature sterilization step has no adverse effect on the medicament contained within the container reservoir.

Containers for use in dispensing beneficial agents in specific dosages, such as the unidose reservoir assembly of the present invention, present unique requirements. More particularly, it is important that as much of the beneficial agents contained within the reservoir assembly be dispensed from a container to avoid improper dosage, waste and undue expense. Accordingly, the previously identified ullage segment functions to fill the interior space of the collapsible container when it is collapsed in the manner shown in FIG. 16 of the drawings.

In a manner presently to be described, fluid medicament reservoir 74 of the fluid reservoir assembly 52 is accessible via a penetrating member 58 which forms the inlet to the fluid delivery and control assembly 54. More particularly, penetrating member 58 is adapted to pierce closure wall 72 as well as a pierceable membrane 78 (FIGS. 7, 11 and 12) which is secured in position over closure wall 72 by means of a closure cap 80 which is affixed to the neck portion 70 of reservoir defining assembly 56 (FIG. 11). As previously described, the reservoir defining assembly 56 is formed using the earlier described aseptic blow fill technique and the reservoir portion of the container is sealed by the thin closure wall 72. Prior to heat sterilization of the container, the piercable membrane 78 is positioned over the closure wall and the closure cap 80 is positioned over the piercable membrane and is secured to the neck portion 70 by any suitable means such as adhesive bonding, sonic welding or heat welding.

Considering now the second assembly 54 of the fluid dispensing apparatus, which is illustrated in FIGS. 4, 5, 6 and 8, this assembly comprises a generally cylindrically shaped housing 80 having a forward portion 80a and a rearward portion 80b. Rearward portion 80b which is covered by a cover, here shown as a second sterile barrier 82 having a pull tab 83, includes an internally threaded cavity 84. Second sterile barrier 82, which is removably connected as by bonding to rearward portion 80b in the manner shown in FIG. 8 of the drawings, here comprises a thin membrane constructed from any suitable polymer.

As illustrated in FIG. 8 of the drawings, housing 80 includes a longitudinally extending bore 86 that rotatably receives the rate control housing 88 of the second assembly 54. Rate control housing 88, which forms a part of the flow control means of the invention, includes an elongated body portion 88a and a forwardly extending finger engaging portion 88b. A plurality of longitudinally spaced apart O-rings 89, which circumscribe body portion 88a, function to prevent fluid leakage between housing 80 and the body portion 88a of the rate control housing. Elongated body portion 88a is also provided with a longitudinally extending bore 90 that slidably receives a disabling shaft 92, the construction and operation of which will presently be described.

Figure 17:
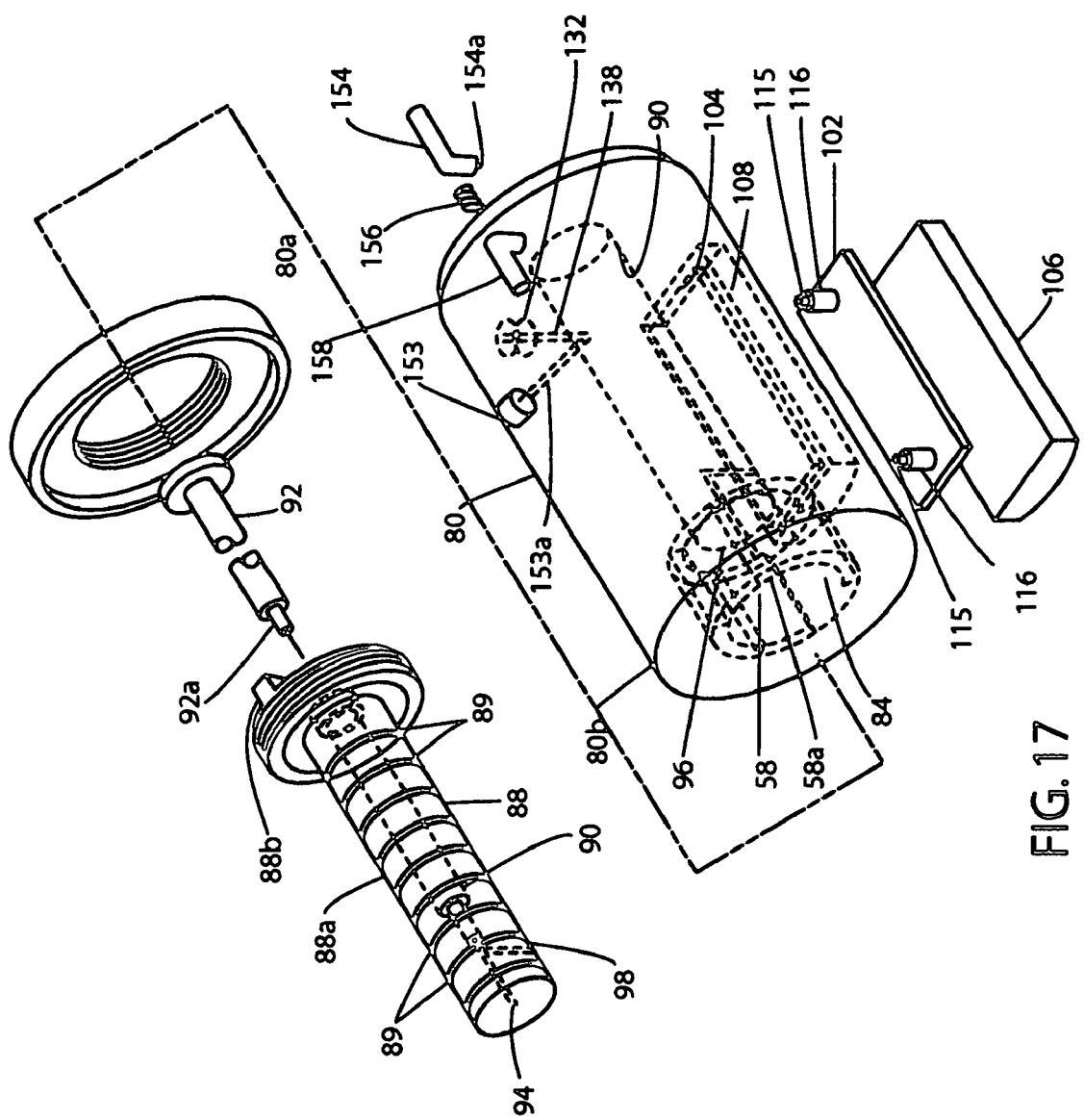
FIG. 17 is a generally perspective, exploded view of the second stand-alone component shown in FIGS. 4, 5 and 6.
Figure 29:
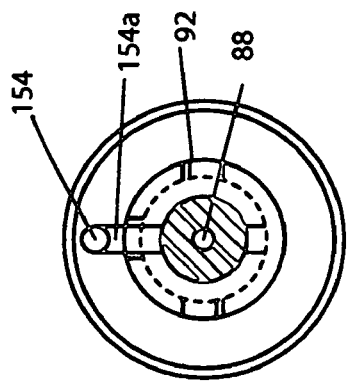
FIG. 29 is a rear view of the second stand-alone component of the invention.

As illustrated in FIGS. 8 and 17, body portion 88a is also provided with a longitudinally extending fluid passageway 94 that communicates with the flow passageway 58a of the previously identified piercing member 58 via a passageway 96 provided in housing 80. For a purpose presently to be described, body portion 88a is also provided with a pair of longitudinally spaced fluid flow passageways 98 and 100.

Fluid flow passageway 98 comprises an inlet passageway that communicates with a rate control assembly 102 that is mounted within a cavity 104 provided in a housing 80. Rate control assembly 102, which also forms a part of the flow control means of the invention, is maintained within cavity 104 by a rate control cover 106, which also forms a part of the flow control means of the invention. As best seen in FIG. 8 of the drawings, rate control cover 106 is disposed within a cavity 108 formed in housing 80.

As previously mentioned, since assembly 54 comprises a stand alone, unitary assembly containing no medicinal fluids, it can be sterilized in the preferred manner by irradiating it with gamma-rays.

As best seen in FIGS. 18 through 22, rate control assembly 102 comprises a rate control plate 110, which as shown in FIG. 23 is provided with a serpentine micro-channel 112 having an inlet 112A and an outlet 112b which communicates with passageway 100 that comprises an outlet passageway. The length, width and depth of the micro-channel determine the rate at which the fluid will flow toward outlet 112b. A thin cover 114 covers the channel in the manner shown in FIG. 18. When assemblies 52 and 54 are interconnected in the manner shown in FIG. 16, inlet 112A is in communication with penetrating member 58 via an outlet tube 115 that is received within and positioned by an upstanding collar 116 provided on rate control plate 110, via passageway 98, via passageway 94 and via passageway 96 (FIG. 8). Because the second assembly has been sterilized in the manner previously described, these passageways are completely sterile at the time assembly 54 is connected to assembly 52.

In using the apparatus of the invention, the first step is to remove the sterile covers 64a and 82 from assemblies 52 and 54. This done, the assemblies can be irreversibly interconnected in the manner illustrated in FIG. 8A by inserting the externally threaded neck 64 of assembly 52 into internally threaded cavity 84 of assembly 54 and rotating assembly 52 relative to assembly 54. As the assemblies mate, penetrating member 58 will penetrate elastomeric member 78 and closure wall 72 of the container.

Figure 9:
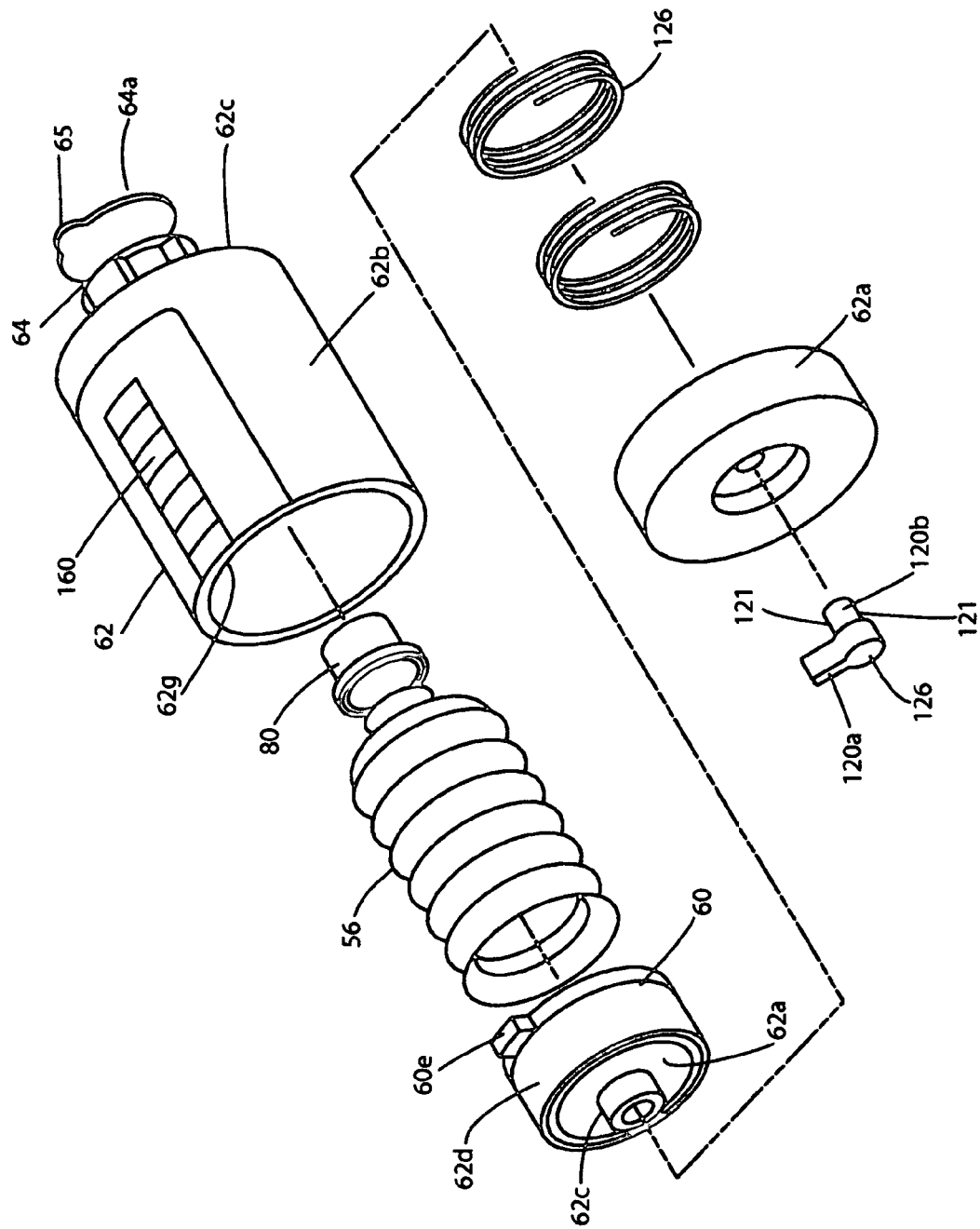
FIG. 9 is a generally perspective, exploded view of the first stand-alone component shown in FIGS. 2 and 3.
Figure 13:
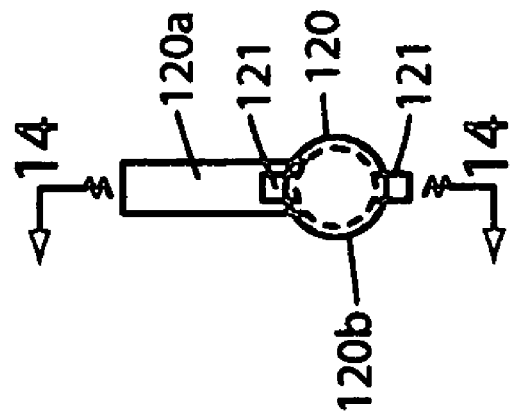
FIG. 13 is a front view of one form of the carriage locking member of the first stand-alone component of the invention.
Figure 14:
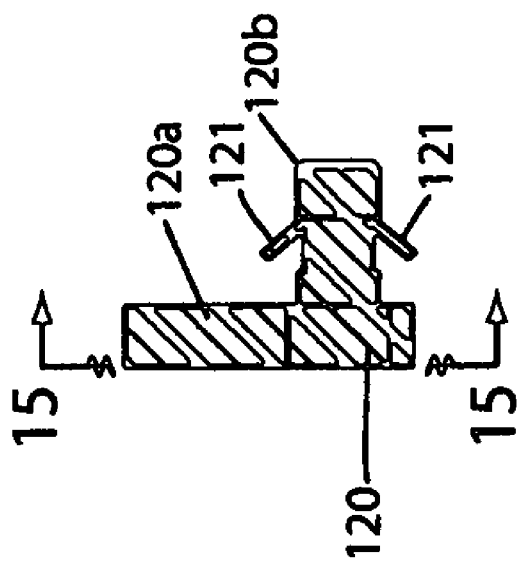
FIG. 14 is a cross-sectional view taken along lines 14-14 of FIG. 13.
Figure 15:
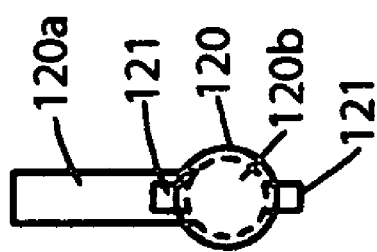
FIG. 15 is a view taken along lines 15-15 of FIG. 14.

With communication between the fluid reservoir 74 and the internal fluid passageway 58a of the penetrating member 58 having thusly been established, the fluid contained within the fluid reservoir can be expelled from the reservoir 74 by rotating the carriage release member 120 which comprises a part of the previously identified carriage locking means. This is accomplished by grasping the finger engaging arm 120A of the release member (FIG. 14) and rotating the member in the manner indicated in FIG. 2 until the threaded shank 120b of the knob threadably disengages from the locking member receiving protuberance 60c. Release member 120 is held in position within housing base 62a by means of circumferentially spaced locking tabs 121 provided on shank 120b. Once the carriage release member is free from the locking member receiving protuberance, the stored energy means, here shown as a coil spring 126 that is movable from the first compressed position shown in FIG. 7 to a second extended position shown in FIG. 16, will urge the carriage forwardly in the manner illustrated in FIG. 16 of the drawings. As the carriage moves forwardly, the circumferentially spaced guide tabs 60e formed on the carriage (FIG. 9) will slide within and be guided by guide channel 62g formed in housing 62 (FIG. 7). As the accordion side walls collapse, the fluid will be forced outwardly of the reservoir into internal passageway 58a of the penetrating member. In the manner previously described, the fluid will then flow toward the fluid flow control means of the invention, which functions to control the flow of fluid from the fluid reservoir of the fluid delivery portion of the device toward the patient.

To enable the fluid to flow from the reservoir 74 to the patient via the administration set 130 (FIG. 8A), the fluid control locking means must be operated in the manner presently to be described.

Figure 8A:
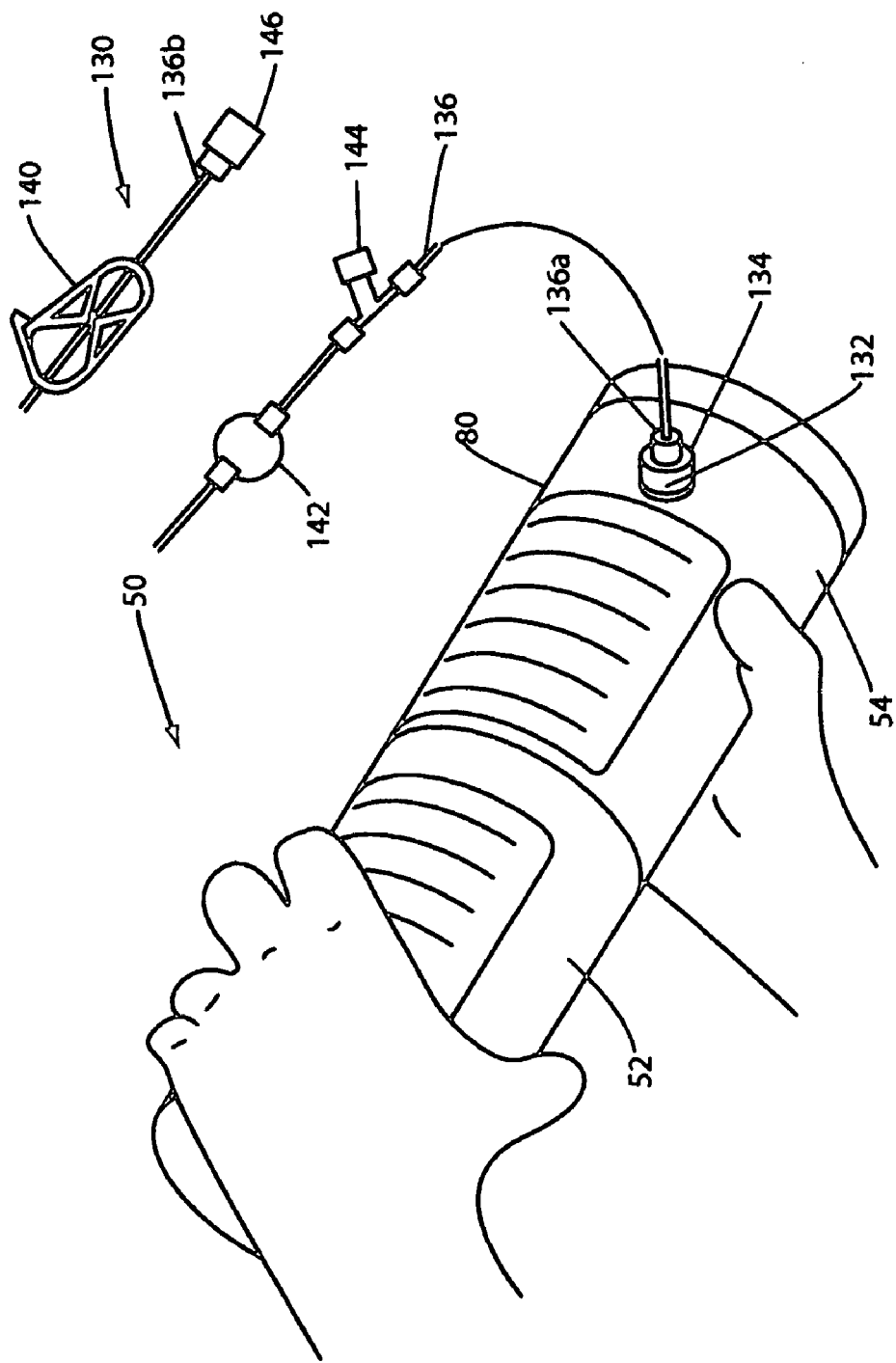
FIG. 8A is a generally perspective, diagrammatic view illustrating the assembly of the two parts of the two-part fluid delivery system of the invention.

As shown in FIG. 8A of the drawings, the administration set 130 is sealably interconnected with an outlet port 132 formed in housing 80. More particularly, the administration set 130 is connected to housing 80 by means of a connector 134 so that the proximal end 136a of the administration line 136 is in communication with an outlet fluid passageway 138 formed in housing 80 (see FIG. 8). Disposed between the proximal end 136a and the distal end 136b of the administration line are a conventional clamp 140, a conventional gas vent and filter 142, and a generally Y-shaped injector site, generally designated by the numeral 144. A luer connector 146 of conventional construction is provided at the distal end 136b of the administration line.

To permit fluid flow from the outlet 112b of the rate control micro-channel 112 toward passageway 138, the rate control housing 88 must be rotated to a position wherein flow passageway 100 aligns with a flow passageway 150 formed in housing 80 (FIG. 8) and also with outlet passageway 138. Since passageway 150 is in communication with outlet 112b of the rate control channel, fluid can flow through the micro-channel at a controlled, fixed rate depending upon the configuration of the channel, into passageway 150, then into passageway 100, then through the rate control housing and finally into passageway 138. From passageway 138 the fluid will flow into the inlet of the administration set for delivery to the patient at a predetermined fixed rate. During the fluid delivery step any gases contained within the device reservoir and the various fluid passageways are vented to atmosphere via vent port 153 and passageway 153a (FIG. 17).

Figure 26:
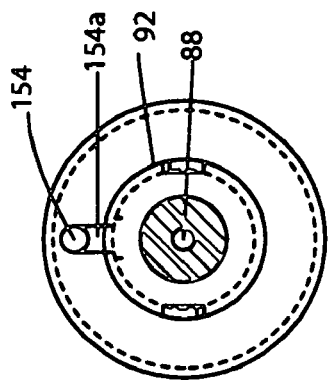
FIG. 26 is a rear view of the second stand-alone component of the invention.
Figure 27:
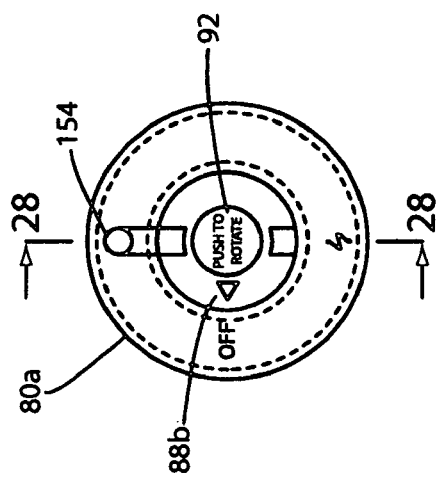
FIG. 27 is a front view of the second stand-alone component of the invention illustrating the operation of the disabling mechanism.
Figure 24:
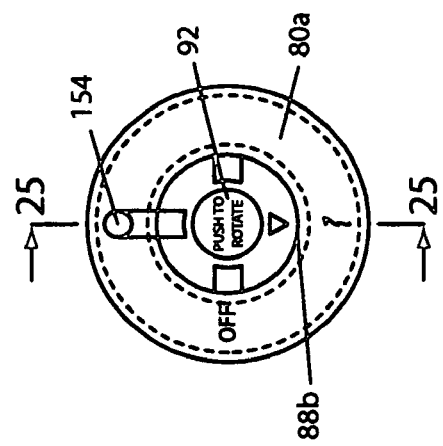
FIG. 24 is a front view of the second stand-alone component of the invention illustrating the operation of the locking plunger of the device to accomplish the fluid dispensing step.
Figure 28:
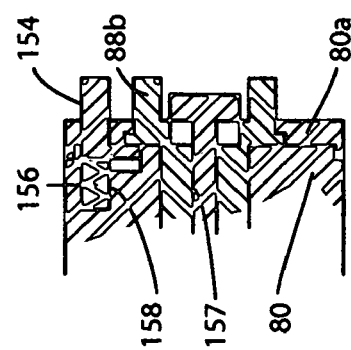
FIG. 28 is a fragmentary cross-sectional view taken along lines 28-28 of FIG. 27.
Figure 25:
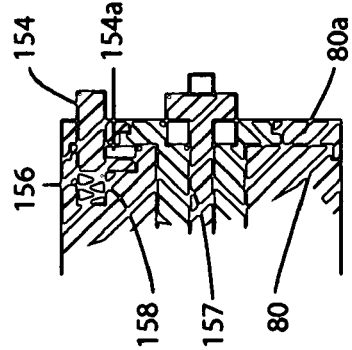
FIG. 25 is a fragmentary cross-sectional view taken along lines 25-25 of FIG. 24.

As previously mentioned, rotation of the rate control housing 88 cannot be accomplished until the rate control locking means is operated by the caregiver. In the present form of the invention this rate control locking means comprises a plunger 154 that includes a locking finger 154a (FIG. 17) that prevents rotation of the rate control housing, unless and until the plunger is moved inwardly of the housing against the urging of a biasing means shown here as coil spring 156 that is housed within a chamber 158 formed in housing 80. Once the plunger is appropriately urged inwardly, rate control housing 88 can be rotated into the correct fluid flow position by grasping rotation fingers 88b and imparting a rotational force to the rotating fingers (see also FIGS. 24, 25 and 26).

Referring to FIGS. 2 and 3, it is to be noted that a reservoir viewing window 160 is provided in housing 62 so that the remaining amount of fluid contained within reservoir 74 can be viewed. Additionally, fluid level indicating indicia 162 are provided on housing 62, proximate window 160 so that the fluid remaining within the reservoir can be accurately monitored by the caregiver.

Fluid flow from the reservoir 74 toward the rate control assembly via passageway 98 can be prevented through operation of the disabling means of the invention. This important disabling means, which is illustrated in FIGS. 8 and 27 through 29, comprises the previously identified disabling shaft 92. As indicated in the drawings, when the disabling shaft 92 is pushed inwardly from the position shown in FIG. 8 into an inward position, wherein it resides within a cavity 157 provided in housing 88, the forward portion 92a of the disabling shaft will move into a cavity 165 formed in rate control housing 88, thereby blocking fluid flow from the internal passageway 58a of the penetrating member into passageway 98. By stopping fluid flow in this manner, the apparatus is substantially safely disabled until the disabling shaft 92 is once again returned to the starting position shown in FIG. 8 of the drawings.

Figures 30, 31:
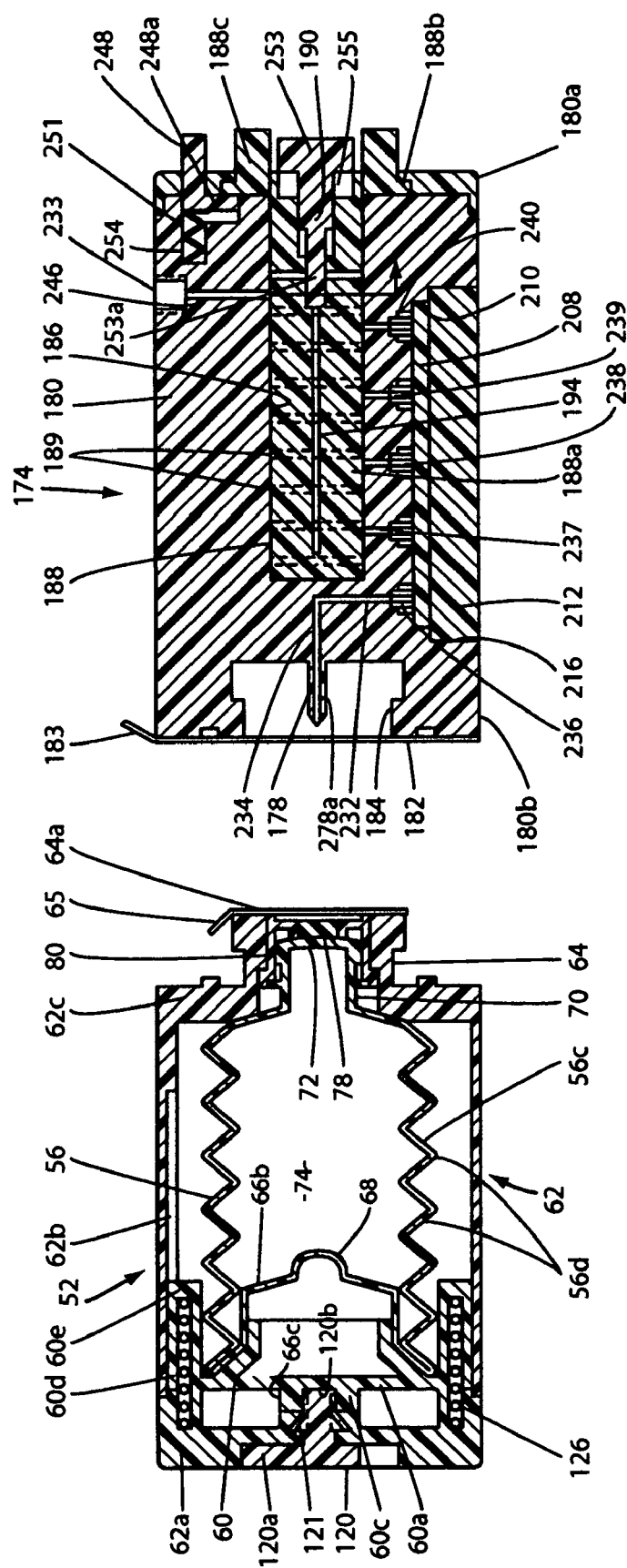
FIG. 30 is a longitudinal cross-sectional view of an alternate form of the first stand-alone component of the invention.
FIG. 31 is a longitudinal cross-sectional view of an alternate form of the second stand-alone component.
Figure 32:
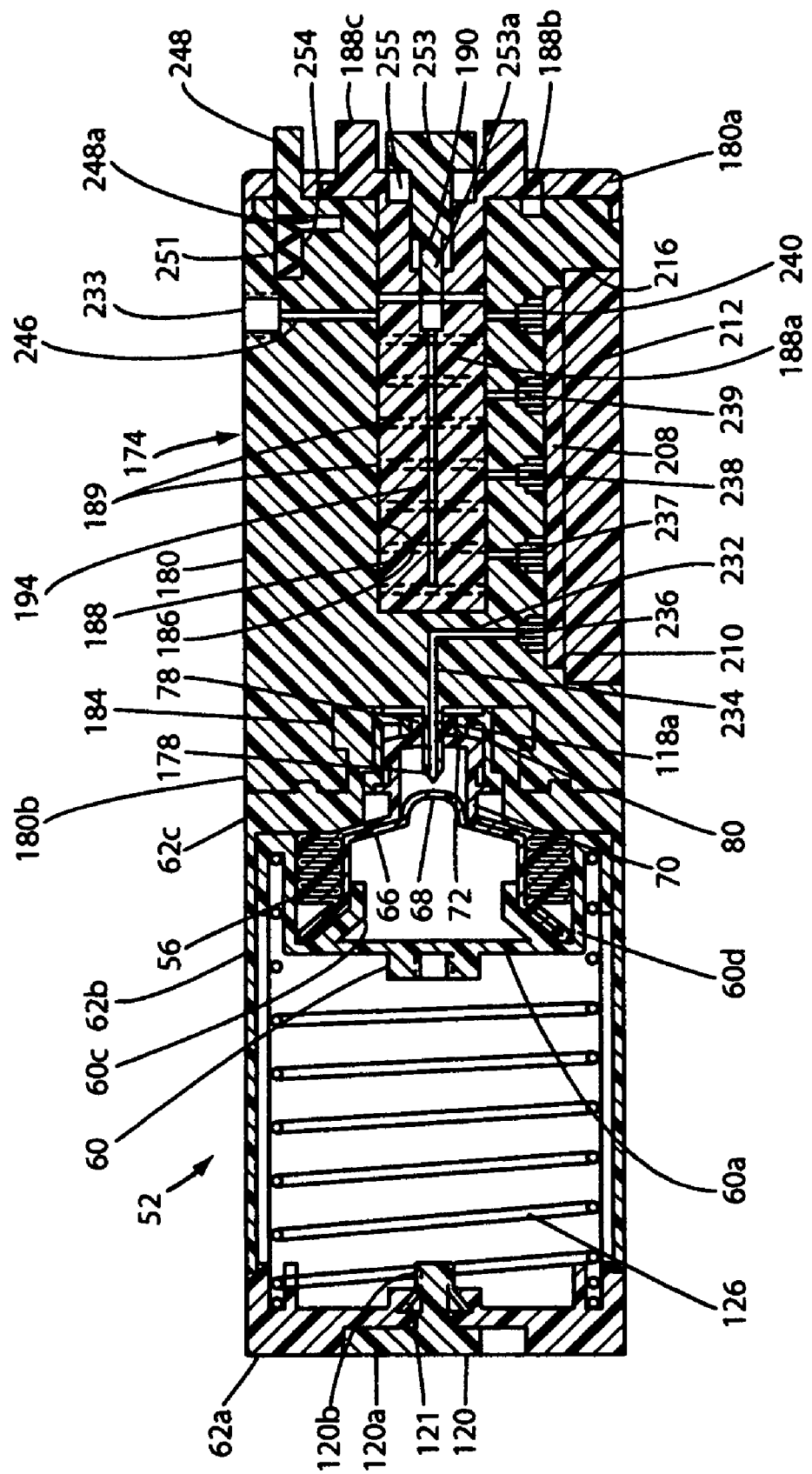
FIG. 32 is a longitudinal cross-sectional view of the fluid dispensing apparatus of the invention shown in FIG. 1 wherein the first and second stand-alone components of the invention have been operably interconnected.

Referring now to FIGS. 30, 31 and 32, an alternate form of the two part fluid dispensing apparatus of the present invention for dispensing medicaments is there shown. This alternate form of dispensing apparatus, which is generally designated in FIG. 32 by the numeral 174, is similar in many respects to the embodiment of the invention illustrated in FIGS. 1 through 29 and like numerals are used in FIGS. 30, 31 and 32 to identify like components. As before, the dispensing apparatus here comprises two stand-alone, inter-connectable assemblies 52 and 174. As indicated in FIG. 30, first assembly 52 is substantially identical in construction and operation to the previously described first assembly and comprises a fluid reservoir assembly that houses a fluid reservoir defining component 56. Assembly 174 is also somewhat similar to the previously described assembly 54 and comprises a fluid delivery and control assembly that includes a penetrating member 178 and a novel fluid flow control means that functions to control the flow of medicinal fluid toward the patient. The primary difference between second assembly 174 and the previously described assembly 54 resides in the provision of a differently constructed rate control assembly that permits the delivery of fluid to the patient at a plurality of selected rates of flow As in the earlier described embodiment of the invention, reservoir defining component 56 is constructed in accordance with aseptic blow-fill seal manufacturing techniques. Following molding, filling in the sealing, the reservoir defining component is sterilized at a relatively high temperature.

In a manner presently to be described, fluid medicament reservoir 74 of the fluid reservoir assembly 52 is accessible via the previously identified penetrating member 178 which forms to inlet to the fluid delivery and control assembly 174. More particularly, penetrating member 178 is adapted to pierce closure wall 72 as well as a pierceable membrane 78 (FIG. 32) which is positioned over closure wall 72 of by means of a closure cap 80 that is affixed to the neck portion 70 of reservoir defining assembly 56 (FIG. 11).

Figure 33:
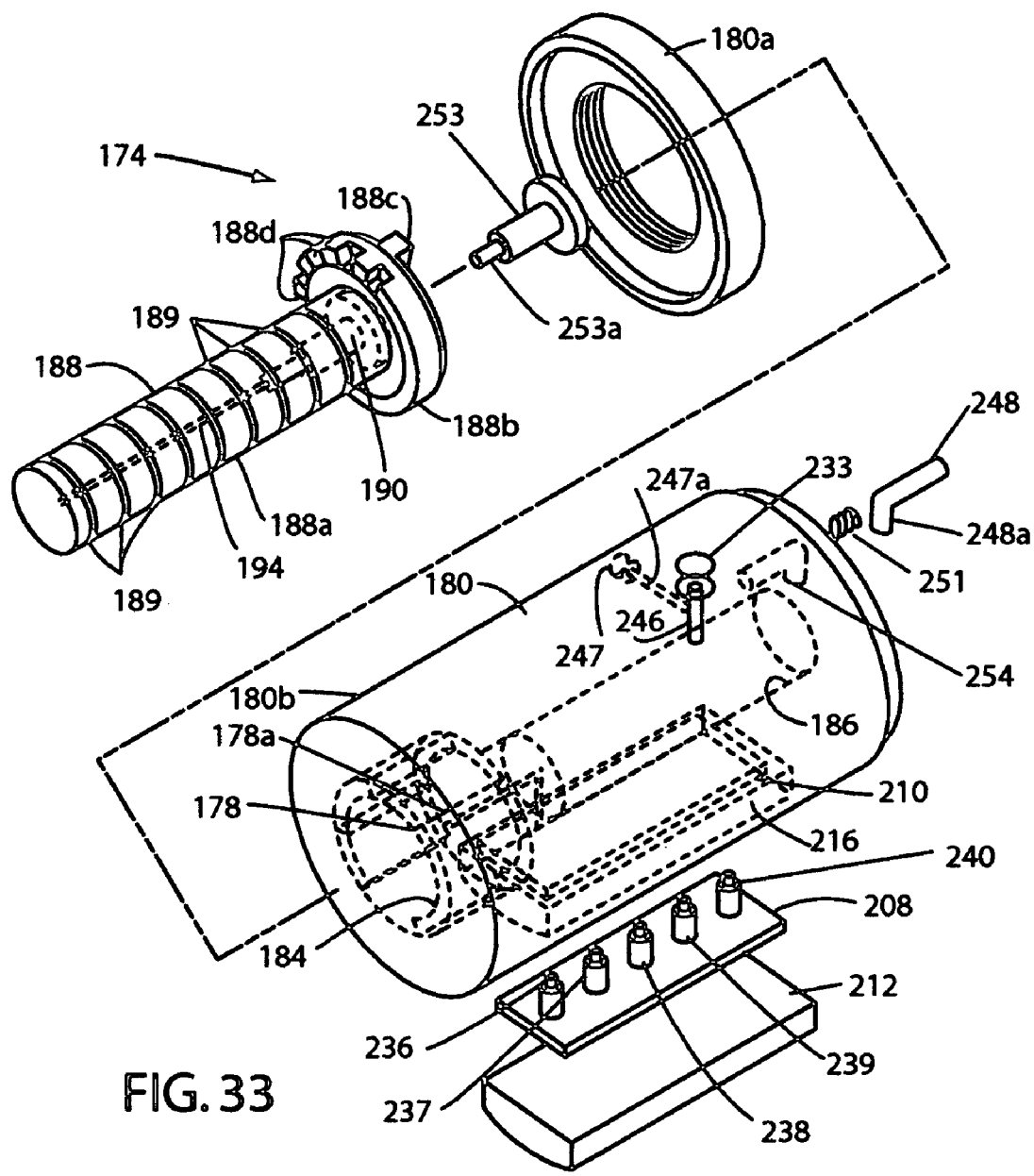
FIG. 33 is a generally perspective, exploded view of the alternate second stand-alone component shown in FIGS. 4, 5 and 6.

Considering now the second assembly 174 of this latest form of the fluid dispensing apparatus which is illustrated in FIGS. 31, 33 and 37, this assembly comprises a generally cylindrically shaped housing 180 having a forward portion 180a and a rearward portion 180b. Rearward portion 180b, which is sealed by a second hermetically affixed sterile barrier 182 having a pull tab 183, includes an internally threaded cavity 184. Second sterile barrier 182, which is removably connected to rearward portion 180b in the manner shown in FIGS. 31 and 37 of the drawings, here comprises a thin membrane constructed from any suitable polymer.

As illustrated in FIGS. 31, 33 and 37 of the drawings, housing 180 includes a longitudinally extending bore 186 that rotatably receives the rate control housing 188 of the second assembly 174. Rate control housing 188, which forms a part of the flow control means of this latest embodiment of the invention, includes an elongated body portion 188a, forward flange 188b and a forwardly extending finger engaging portion 188c that is connected to and extends forwardly of flange 188b. For a purpose presently to be described, a plurality of circumferentially spaced apart channels, or cavities, 188d are formed on the rear face of flange 188b. Additionally, a plurality of longitudinally spaced apart O-rings 189, which circumscribe body portion 188a, function to prevent fluid leakage between housing 180 and the body portion 188a of the rate control housing as the rate control housing is rotated. Elongated body portion 188a is also provided with a longitudinally extending bore 190 that slidably receives the rearward portion of a disabling shaft 253, the construction and operation of which will presently be described.

As illustrated in FIGS. 31, 37 and 38, body portion 188a is also provided with a longitudinally extending fluid passageway 194 that communicates with the flow passageway 178a of the previously identified piercing member 178 via the flow rate control means. For a purpose presently to be described, body portion 188a is also provided with a plurality of forwardly positioned, circumferentially spaced apart, radially extending outlet fluid flow passageways 198, 200, 202 and 204 that communicate with longitudinally extending, central passageway 194 (FIGS. 41, 42 and 43).

In a manner presently to be described, a plurality of longitudinally spaced apart, radially extending inlet fluid flow passageways 199, 201, 203 and 205 (FIG. 42) also communicate with fluid passageway 194 and as the rate control housing 188 is rotated, selectively communicate with a rate control assembly 208 (FIG. 34) that is mounted within a cavity 210 provided in a housing 180 (FIG. 37). Rate control assembly 208, which also forms a part of the flow control means of this latest form of the invention, is maintained within cavity 210 by a rate control cover 212, which also forms a part of the flow control means of the invention. As best seen in FIG. 33 of the drawings rate control cover 212 is disposed within a cavity 216 formed in housing 180.

Figures 34, 35:
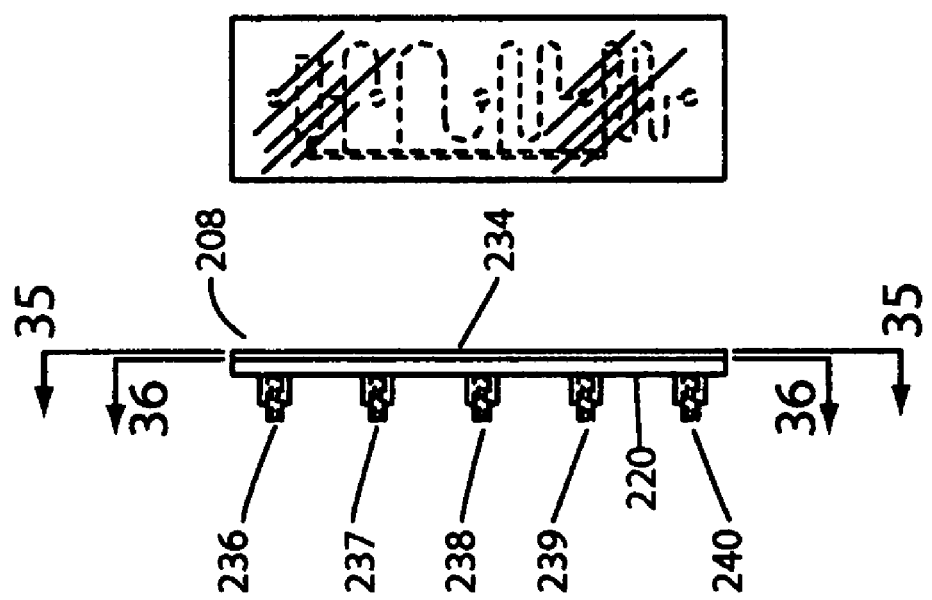
FIG. 34 is a side elevational view of one form of the rate control plate assembly of the alternate second stand-alone component of the invention that includes a rate control plate and control plate cover.
FIG. 35 is a view taken along lines 35-35 of FIG. 34.
Figure 36:
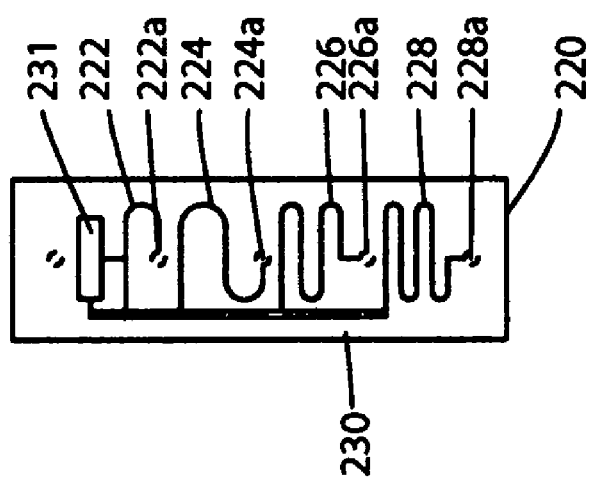
FIG. 36 is a view taken along lines 36-36 of FIG. 34.
Figure 45:
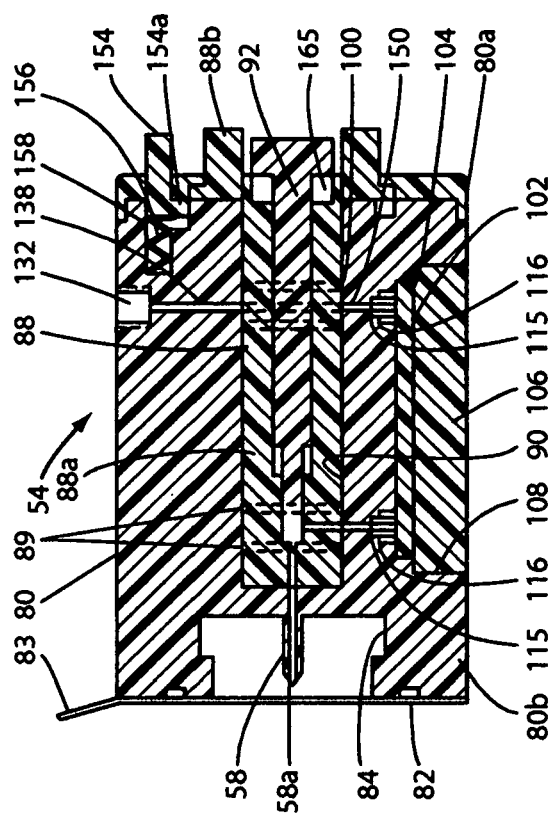
FIG. 45 is a longitudinal cross-sectional view similar to the second stand-alone component shown in FIGS. 4, 5 and 6.
Figure 46:
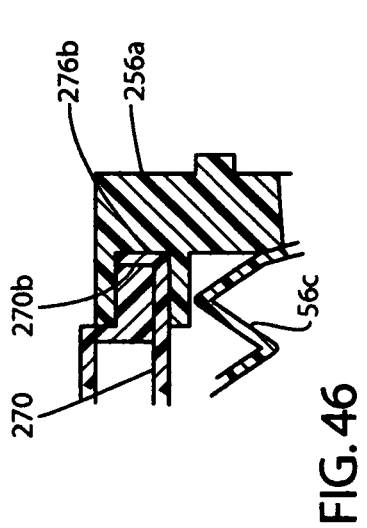
FIG. 46 is an enlarged fragmentary cross-sectional view of the portion identified as 46 in FIG. 44.

Turning to FIGS. 34 through 36, it can be seen that rate control assembly 208 comprises a rate control plate 220, which as shown in FIG. 36 is provided with a plurality of spaced apart, serpentine micro-channels 222, 224, 226 and 228. Each of the micro-channels is of a different width, depth and length and each has an inlet in communication with an elongated passageway 230, which, in turn is in communication with the internal passageway 178a of the penetrating member 178 via a pressure regulator 231, and via passageways 232 and 234 formed in housing 180 (see FIG. 37). A thin cover 234 covers the channels in the manner shown in FIG. 34.

When assemblies 52 and 174 are interconnected in the manner shown in FIG. 32, elongated passageway 234 is in communication with penetrating member 178 via a connector collar 236 provided on rate control plate 220, via passageway 232 and via passageway 234 (FIG. 37).

In using the apparatus of the invention, the first step is to remove the sterile covers 64a and 182 from assemblies 52 and 174. This done, the assemblies can be interconnected by inserting the externally threaded neck 64 of assembly 52 into internally threaded cavity 184 of assembly 174 and rotating assembly 52 relative to assembly 174. As the assemblies are mated, penetrating member 178 will penetrate elastomeric member 78 and closure wall 72 of the container.

With communication between the fluid reservoir 74 and the internal passageway 178a of the penetrating member 178 having thusly been established, the fluid contained within the fluid reservoir can be expelled from the reservoir 74 by rotating the carriage release member 120 in the manner previously described. Once the carriage release member is free from the locking member receiving protuberance, the stored energy means, here shown as a coil spring 126 that is movable from the first compressed position to the second extended position, will urge the carriage forwardly. As the carriage moves forwardly, the accordion side walls of the container collapse causing the fluid to be forced outwardly of the reservoir into internal passageway 178a of the penetrating member. The fluid will then flow toward passageway 230 of the rate control plate 220 via the pressure regulator 231. From the pressure regulator, which controllably adjusts the pressure of the fluid flowing therefrom, the fluid will flow into and fill each of the micro-channels to 222, 224, 226 and 228 that are interconnected with passageway 230 in the manner shown in FIG. 36.

To enable the fluid to flow from the reservoir 74 to the patient via the administration set 130 (FIG. 8A) that can be connected to the outlet port 233 of housing 180 (FIG. 33), the fluid control locking means of this latest form of the invention must be operated. More particularly to permit fluid flow selectively from the outlets 222a, 224a, 226a, and 228a, respectively, of the differently configured micro-channels (FIG. 36), the rate control housing 188 must be controllably rotated in a manner to selectively align the radially extending passageways 199, 201, 203 and 205 (FIG. 39) with the longitudinally spaced apart flow passageways 237, 238, 239 and 240 formed in housing 180 (FIG. 37). Since passageways 237, 238, 239 and 240 are in communication with microchannel outlets 222a, 224a, 226a, and 228a, respectively, of the differently configured micro-channels, fluid can flow from the selected micro-channel toward the selected flow passageway 237, 238, 239 or 240 at a controlled rate that depends upon the configuration of the particular channel selected. From the selected flow passageways 237, 238, 239 and 240, fluid will flow through one of the selected longitudinally spaced apart radially extending passageways formed in the rate control housing. From this selected passageway (shown in FIG. 39 as passageway 199) the fluid will flow into passageway 194 and then into passageway 246 formed in housing 180. From passageway 237 the fluid flows at the selected flow rate into the inlet of the administration set for delivery to the patient at the selected rate. As in the earlier described embodiment, any gases trapped in the device reservoir and in the various fluid passageways will be vented to atmosphere via a vent port 247 and passageway 247a (FIG. 33).

As in the earlier described embodiment of the invention, rotation of the rate control housing 188 cannot be accomplished until the rate control locking means is operated by the caregiver. In this latest form of the invention the rate control locking means comprises a plunger 248 that includes a locking finger 248a (FIG. 37) that prevents rotation of the rate control housing, unless and until the plunger is moved inwardly of the housing against the urging of a biasing means shown here as coil spring 251 that is housed within a chamber 254 formed in housing 180. Once the plunger is appropriately urged inwardly and removed from the channels 188d formed in flange 188b, rate control housing 188 can be rotated into the desired fluid flow position by grasping rotation fingers 188c and imparting a rotational force thereto. Referring particularly to FIGS. 37 and 42, it is to be noted that as the rate control housing is rotated, spring 251 continuously urges locking finger 248a into a selected locking channel 188d formed in flange 188b. When the locking finger is seated within a particular locking channel, one of the radially extending passageways formed in the rate control housing (here shown as passageway 199) will be locked in communication with one of the outlets of one of the plurality of micro channels formed in the rate control plate and the fluid will flow through the selected micro channel toward the patient at a selected fixed-rate. When it is desired to once again create a fluid flow toward the patient, the plunger 248 must once again be depressed and the rate control housing rotated into another position.

As in the earlier described embodiment of the invention, a reservoir viewing window 160 is provided in housing 62 so that the amount of fluid contained within reservoir 74 can be viewed. Additionally, fluid level indicia 162 are provided on housing 62, proximate window 160, so that the fluid remaining within the reservoir can be accurately monitored by the caregiver.

Fluid flow from the reservoir 74 toward the rate control assembly of the second assembly 174 via passageway 236 can be prevented through operation of the disabling means of the invention. This important disabling means, which is of a similar construction and operation to that earlier described, comprises a disabling shaft 253. As indicated in FIG. 37 of the drawings, when the disabling shaft 253 is pushed inwardly from the position shown in FIG. 37 into an inward position, wherein it resides within a cavity 255 provided in housing 188, the forward portion 253a of the disabling shaft will move into a position where it blocks fluid flow from passageway 194 toward passageway 246 so as to stop fluid flow toward the administration set. By stopping fluid flow in this manner, the apparatus is substantially disabled until the disabling shaft 253 is once again returned to the starting position shown in FIG. 37 of the drawings.

Figure 44:
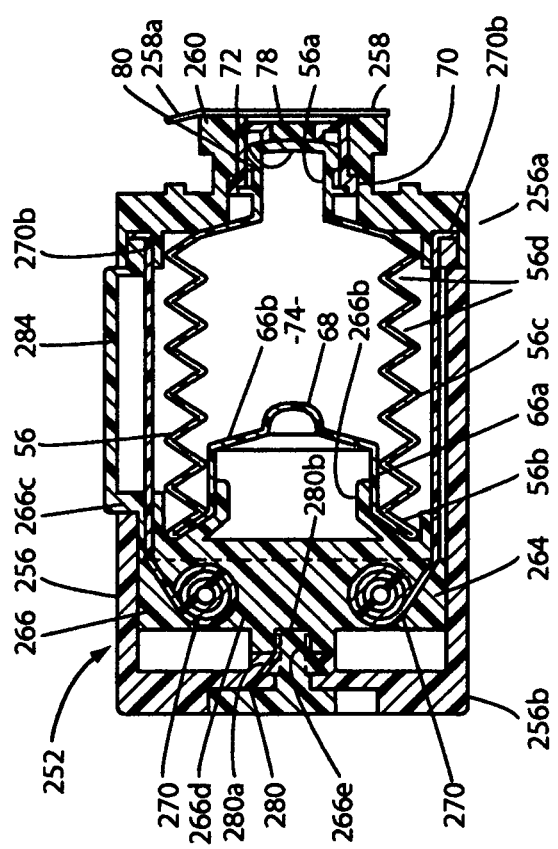
FIG. 44 is a longitudinal cross-sectional view of an alternate form of the first stand-alone component of the invention shown in FIGS. 1 and 2.

Turning next to FIGS. 41 through 43, still another form of the two part fluid dispensing apparatus of the present invention for dispensing medicaments is there shown. This second, alternate, form of dispensing apparatus is similar in many respects to the earlier described embodiments of the invention and like numerals are used in FIGS. 44 through 47 to identify like components. As before, dispensing apparatus 174 comprises two stand-alone, inter-connectable assemblies of the character shown in FIGS. 44 and 47. As indicated in FIG. 44, first assembly 252 is of a somewhat different construction, while second assembly 54 is substantially identical in construction and operation to the previously described second assembly 54. The primary difference between first assembly 252 and the previously described assembly 52 resides in the provision of a totally different stored energy means for moving a somewhat differently configured carriage 264 from a first retracted position to a second advanced position. Second assembly 54 includes a rate control assembly that permits the delivery of fluid to the patient at a substantially fixed rate The reservoir defining component 56 of this latest form of the invention is quite similar in construction and operation to the previously described and is constructed in accordance with aseptic blow-fill seal manufacturing techniques, the character previously described. Following molding, filling and sealing, the reservoir defining component is sterilized at a relatively high temperature.

In a manner presently to be described, fluid medicament reservoir 74 of the fluid reservoir assembly 252 is accessible via the penetrating member 58 of the fluid delivery and control assembly 54. More particularly, penetrating member 58 is adapted to pierce closure wall 72 as well as a pierceable membrane 78 (FIG. 44) which is positioned over closure wall 72 by means of a closure cap 80 which is affixed to the neck portion 70 of reservoir defining assembly 56 (see FIG. 11).

Considering now in greater detail the first assembly 252 of this latest form of the fluid dispensing apparatus, this assembly comprises a generally cylindrically shaped housing 256 having a forward portion 256a and a rearward portion 256b. Forward portion 256a, which is sealed by a sterile barrier 258 having a pull tab 258a, includes an externally threaded neck 260 that is receivable within threaded cavity 84 of the second assembly 54.

In addition to the reservoir defining component 56, assembly 252 includes a carriage assembly 264 and a stored energy means that is operably associated with the carriage assembly for moving the carriage assembly between the first retracted position and the second advanced position. Carriage assembly 264 includes a base assembly 266 that includes a forward portion having, a base 266, a reservoir receiving flange 266b and a fluid level indicator boss 266c. Base assembly 266 also includes a rear portion having housing 266d that is provided with a threaded carriage locking member receiving cavity 266e (see also FIG. 47). Mounted within the housing 273 is the important stored energy means of this latest form of the invention which here comprises a pair of constant force springs 270. Carriage assembly 264 is releasably locked in its first position by a novel carriage locking means, the character of which will be described in the paragraphs which follow.

As in the earlier described embodiments of the invention and as illustrated in FIG. 11 of the drawings, reservoir defining component 56 here comprises an integrally formed, hermetically sealed container that includes a front portion 56a, a rear portion 56b and a collapsible accordion-like, continuous, uninterrupted side wall 56c that interconnects the front and rear portion of the container. As illustrated in the drawings, the accordion like side wall 56c comprises a multiplicity of adjacent generally "V" shaped interconnected folds, 56d. Rear portion 56b of the container includes an inwardly extending ullage segment 66 having a side wall 66a and an end wall 66b. As illustrated in FIGS. 7 and 11, end wall 66b includes a generally hemispherical shaped protuberance 68. Front portion 56a of the container includes an integrally formed neck 70 having a closure wall 72. Front portion 56a, rear portion 56b and side wall 56c cooperate to define the fluid reservoir 74 of the fluid reservoir assembly 52.

Figure 47:
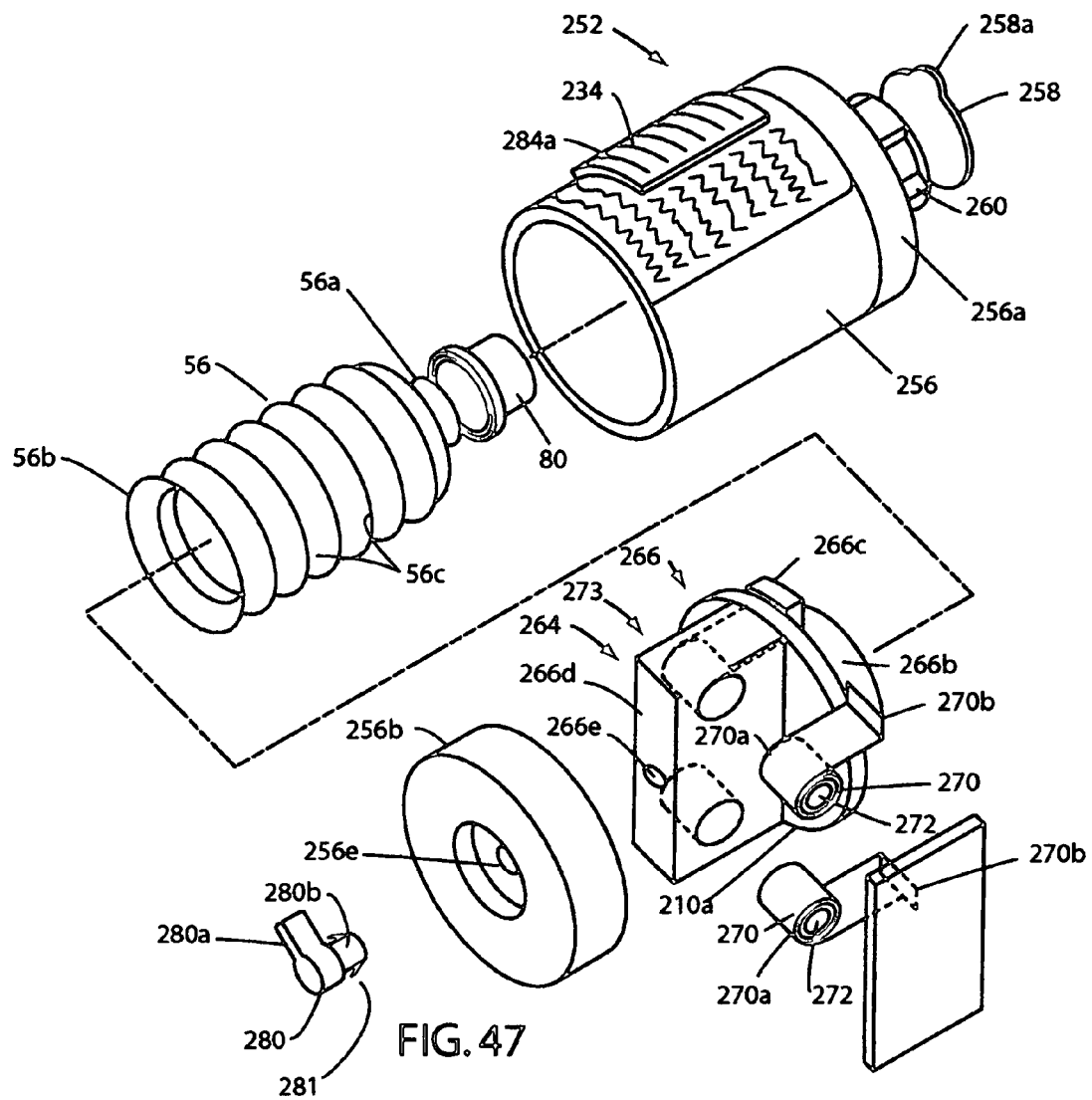
FIG. 47 is a generally perspective exploded view of the second stand-alone component of the invention shown in FIG. 17.

Constant force springs, such as springs 270 are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force, the same as a common extension spring but at a nearly constant (zero) rate. The constant-force spring is well suited to long extensions with no load build-up. As best seen in FIGS. 44 and 47, springs 270 are mounted with one end 270a tightly wrapped on a drum 272 that is housed with a carriage block 273 and the other end 270b attached forward portion 256a of housing 256 in the manner shown in FIG. 47.

In using the apparatus of this latest form of the invention, the first step is to remove the sterile covers 258 and 82 from assemblies 252 and 54. This done, the assemblies can be interconnected by inserting the externally threaded neck 260 of assembly 252 into internally threaded cavity 84 of assembly 54 and rotating assembly 252 relative to assembly 54. As the assemblies mate, penetrating member 58 will penetrate elastomeric member 78 and closure wall 72 of the container.

With communication between the fluid reservoir 74 and the internal passageway 58a of the penetrating member 58 having thusly been established, the fluid contained within the fluid reservoir can be expelled from the reservoir 74 by rotating the carriage release member 280 which comprises a part of the previously identified carriage locking means. This is accomplished by grasping the finger engaging arm 280a of the release member (FIG. 47) and rotating the member until the threaded shank 280b of the knob threadably disengages from the locking member receiving cavity 266e. Release member 280 is held in position within base 266d by means of circumferentially spaced locking tabs 281 provided on shank 280b. Once the carriage release member is free from the locking member receiving cavity, the stored energy means, here shown as constant force springs 270, will urge the carriage assembly 266 forwardly. As the carriage moves the accordion side walls 56c of the collapsible container will collapse and the fluid will be forced outwardly of the reservoir into internal passageway 58a of the penetrating member. In the manner previously described, the fluid will then flow toward the fluid flow control means of assembly 54, which functions to control the flow of fluid from the fluid reservoir of the fluid delivery portion of the device toward the patient.

To enable the fluid to flow from the reservoir 74 to the patient via the administration set 130 (FIG. 8A), the fluid control locking means must be operated in the manner previously described in connection with the first embodiment of the invention.

Referring to FIGS. 44 and 47, it is to be noted that a reservoir viewing window 284 is provided in housing 256 so that the amount of fluid contained within reservoir 74 can be determined by viewing the advance of the fluid indicator boss 266c. Additionally, fluid level indicia 284a are provided on window 284 so that the fluid remaining within the reservoir can be accurately monitored by the caregiver.

As in the earlier described embodiments of the invention, fluid flow from the reservoir 74 toward the rate control assembly of the second assembly 54 can be prevented through operation of the disabling means of the invention in a manner previously described, which disabling means comprises the previously identified disabling shaft 92.

Figure 49:
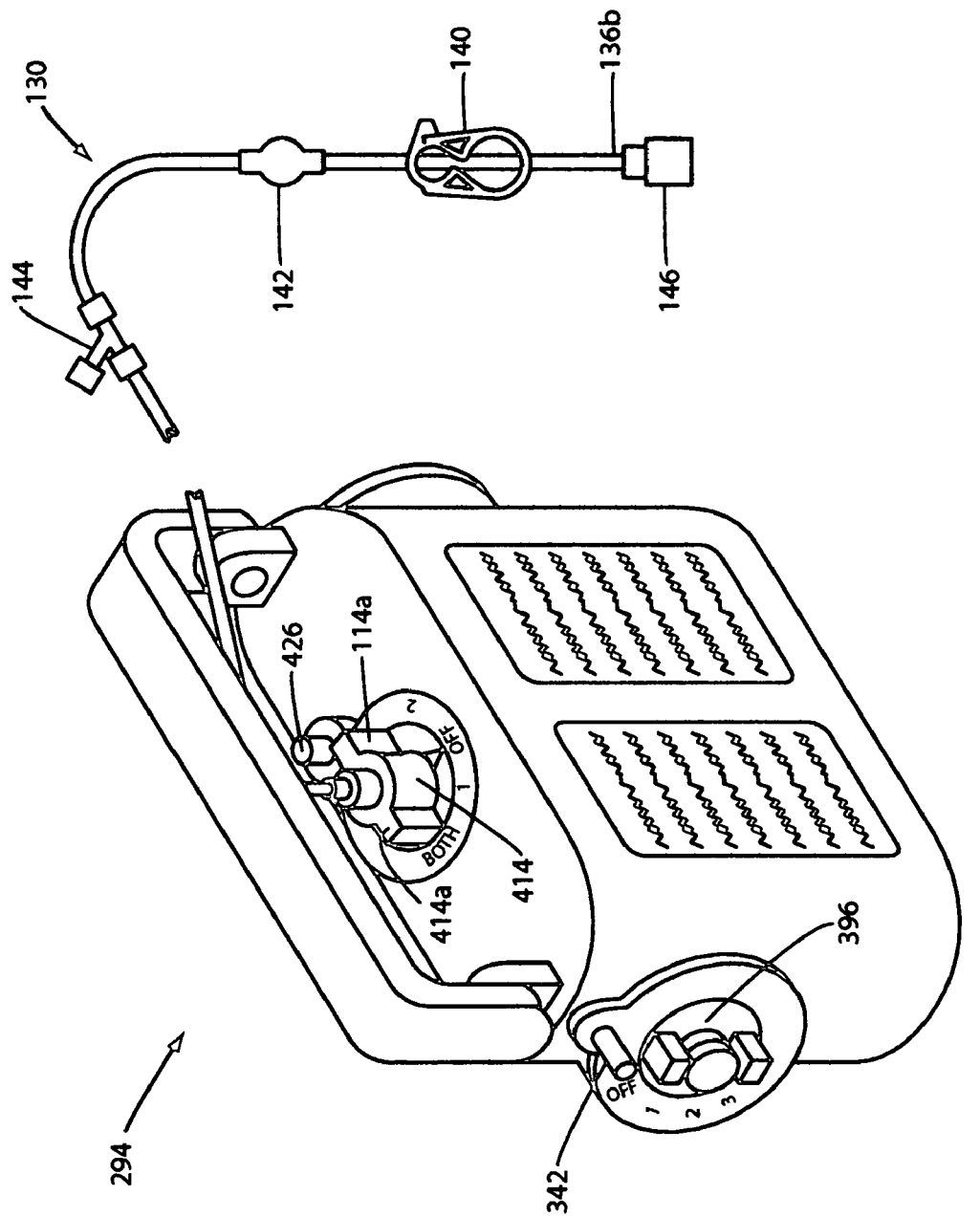
FIG. 49 is a generally perspective view of still another form of the fluid delivery system of the present invention.
Figure 50:
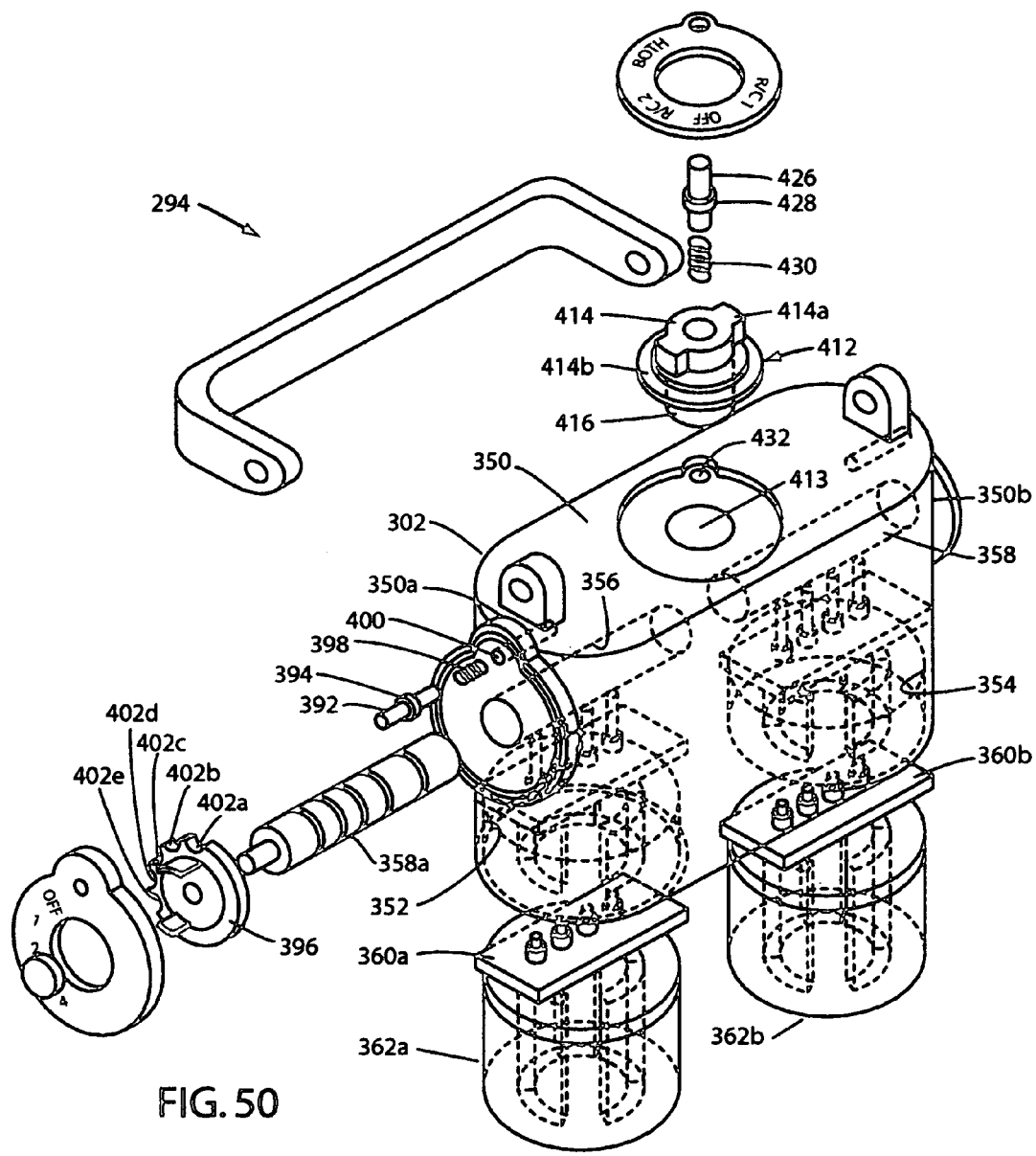
FIG. 50 is an enlarged, generally perspective, exploded view of the alternate form of the fluid delivery system shown in FIG. 49 partly broken away to show internal construction.
Figure 51:
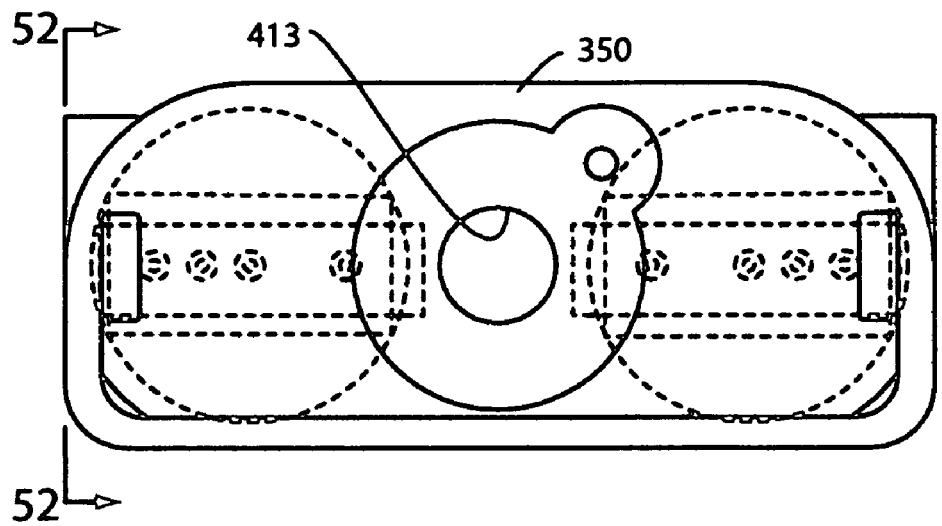
FIG. 51 is a top plan view of the housing of the stand-alone fluid delivery and control component of the alternate form of the two-part fluid delivery system shown in FIG. 49.
Figure 52:
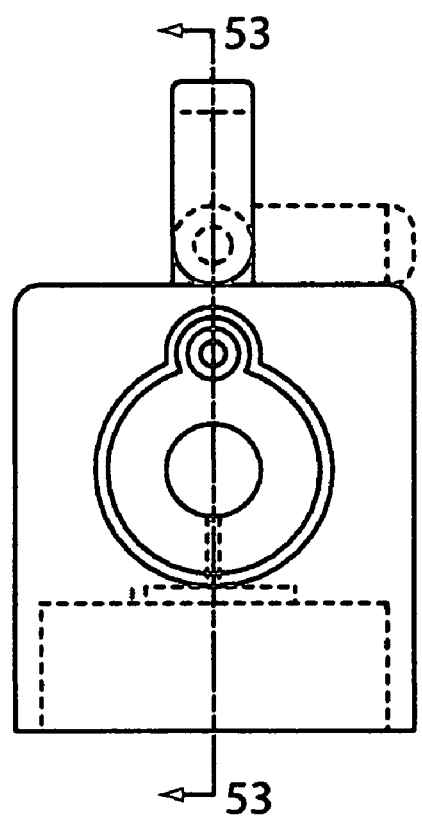
FIG. 52 is a view taken along lines 52-52 of FIG. 51.

Turning to FIG. 49 yet another form of the two part fluid dispensing apparatus of the present invention for dispensing medicaments is there shown and generally identified by the numeral 290. This alternate form of dispensing apparatus is similar in some respects to the earlier described embodiments of the invention and like numerals are used to identify like components in FIGS. 49 through 62. As before, dispensing apparatus 290 comprises two stand-alone, inter-connectable assemblies 252 and 174. As indicated in FIG. 49, first assembly 252 is substantially identical in construction and operation to the previously described first assembly that is illustrated in FIG. 44 of the drawings and comprises a fluid reservoir assembly that houses a fluid reservoir defining component 56 that is acted upon by a pair of constant force springs 270. Assembly 174 is substantially identical in construction and operation to the previously described second assembly that is illustrated in FIGS. 31, 33 and 37 of the drawings.

Assembly 174 comprises a penetrating member 178 and a novel fluid flow control means that includes a rate control assembly that permits the delivery of fluid to the patient at a plurality of selected rates of flow.

As in the earlier described embodiments of the invention, reservoir defining component 56 is constructed in accordance with aseptic blow-fill seal manufacturing techniques. As before, following molding, filling and sealing the reservoir defining component is sterilized at a relatively high temperature.

Figure 48:
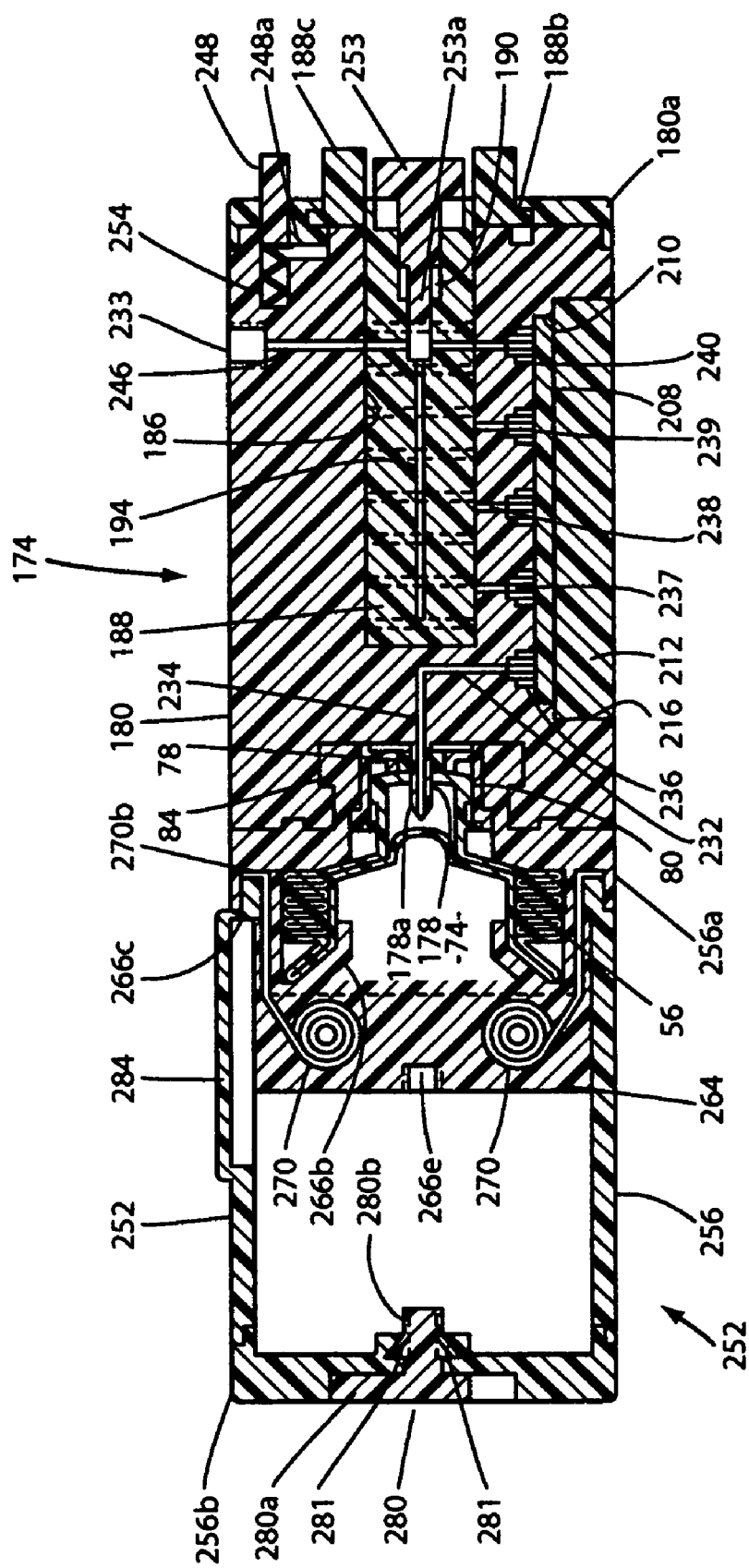
FIG. 48 is a longitudinal cross-sectional view of the fluid dispensing apparatus of the invention shown in FIG. 17 wherein the first and second stand-alone components of the invention have been irreversibly operably interconnected.

As before, second assembly 174 of this latest form of the fluid dispensing apparatus comprises a housing 180 that includes a longitudinally extending bore 186 that rotatably receives the rate control housing 188 of the second assembly, which rate control housing forms a part of the flow control means of the invention. The flow control means includes a rate control assembly 208 that is mounted within a cavity 210 provided in housing 180. Rate control assembly 208 comprises a rate control plate 220 that is provided with a plurality of spaced apart, serpentine micro-channels, each of which is of a different width, depth and length. When assemblies 252 and 174 are interconnected in the manner shown in FIG. 48, elongated passageway 230 of the rate control plate 220 is in communication with penetrating member 178 via a connector collar 236 provided on rate control plate 220, via passageway 232 and passageway 234.

With communication between the fluid reservoir 74 and the internal passageway 178a of the penetrating member 178 established, the fluid contained within the fluid reservoir can be expelled from the reservoir 74 by rotating the carriage release member 280 in the manner previously described. Once the carriage release member is free from the locking member receiving cavity 266e, the stored energy means, here shown as the pair of constant force springs 270 will urge the carriage forwardly. As the carriage moves forwardly, the accordion side walls of the container collapse causing the fluid to be forced outwardly from the reservoir into internal passageway 178a of the penetrating member. The fluid will then flow toward passageway 230 of the rate control plate 220 via the pressure regulator 231 and then into each of the micro-channels to 222, 224, 226 and 228 that are interconnected with passageway 230. To enable the fluid to flow from the reservoir 74 to the patient at a selected rate via the administration set 130, the fluid control locking means of this latest form of the invention must be operated in the manner previously described.

As in the earlier described embodiments of the invention, a reservoir viewing window 284 is provided in housing 252 so that the amount of fluid contained within reservoir 74 can be monitored. Similarly, fluid flow from the reservoir 74 toward the rate control assembly of the second assembly can be prevented through operation of the disabling means that is of the character previously described.

Figure 59:
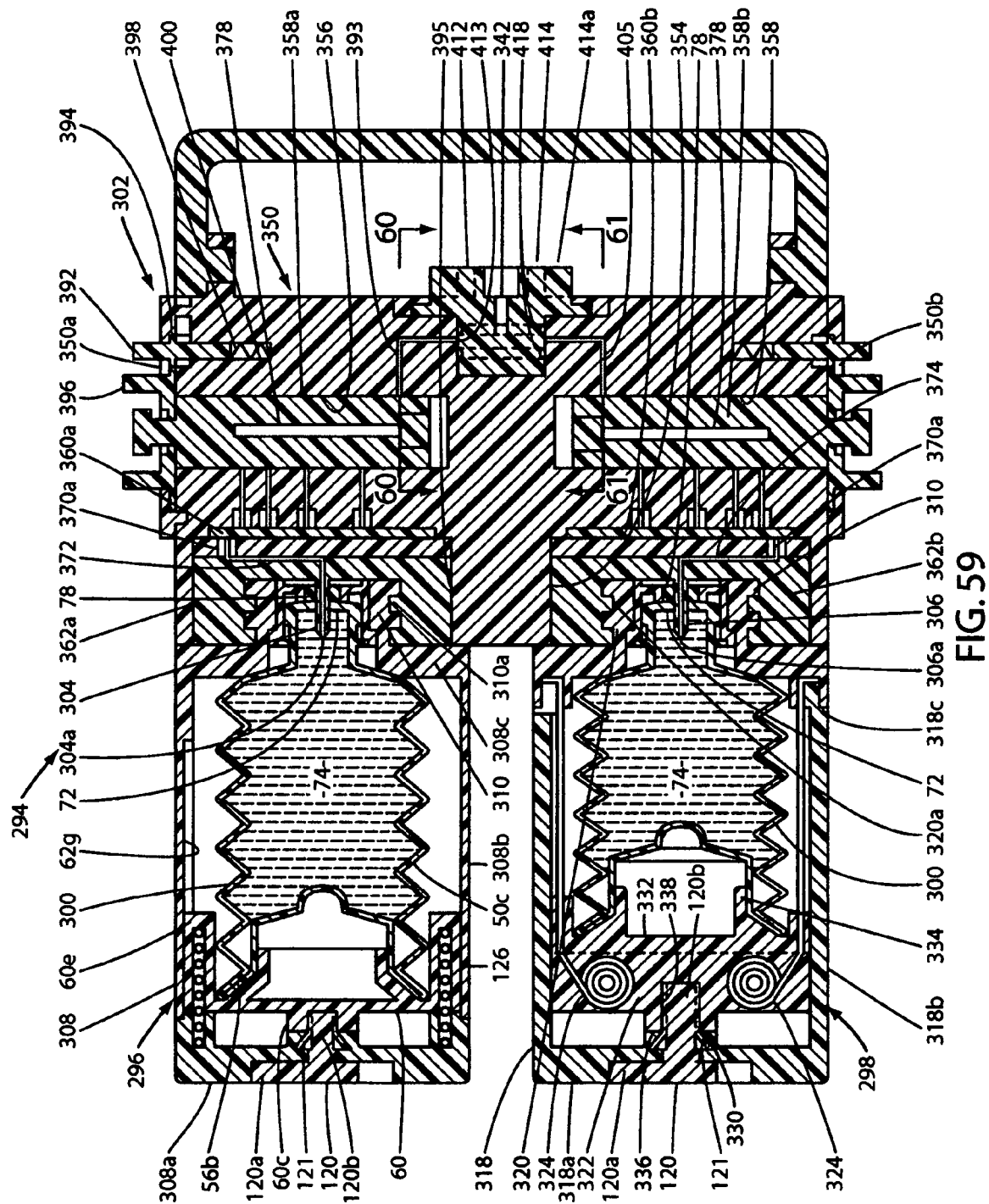
FIG. 59 is a longitudinal cross-sectional view of the fluid dispensing apparatus of the invention shown in FIG. 49, wherein the first and second stand-alone unitary fluid reservoir assembly components of the invention have been operably interconnected with the fluid delivery and control assembly.

Referring now to FIGS. 49 through 62, an alternate form of the fluid dispensing apparatus of the present invention for dispensing medicaments is there shown. This alternate form of dispensing apparatus, which is generally designated in FIG. 49 by the numeral 294, is similar in some respects to the embodiment of the invention illustrated in FIGS. 1 through 29 and like numerals are used in FIGS. 49 through 62 to identify like components. The dispensing apparatus here uniquely comprises two unitary fluid reservoir assemblies 296 and 298, each of which houses a fluid reservoir defining component 300 (FIG. 59) that is of substantially identical construction to the fluid reservoir defining component 56 previously described in connection with the embodiment of FIGS. 1 through 41. As illustrated in FIG. 59 of the drawings, the dispensing apparatus here comprises a fluid delivery and control assembly 302 that includes two spaced apart penetrating members 304 and 306 and a novel fluid flow control means that functions to control the flow of medicinal fluid toward the patient.

Considering first the unitary fluid reservoir assembly 296, the fluid reservoir defining component 300 and the stored energy means are all housed within a generally cylindrically shaped housing 308 that includes a base 308a, an outer wall 308b and a top wall 308c. Connected to top wall 308c is a connector neck 310 having bayonet like connector grooves 310a (FIG. 59). Connector neck 310 is initially closed by a sterile barrier (not shown) that is similar to sterile barrier 64a and is removably connected to the connector neck.

Figure 62:
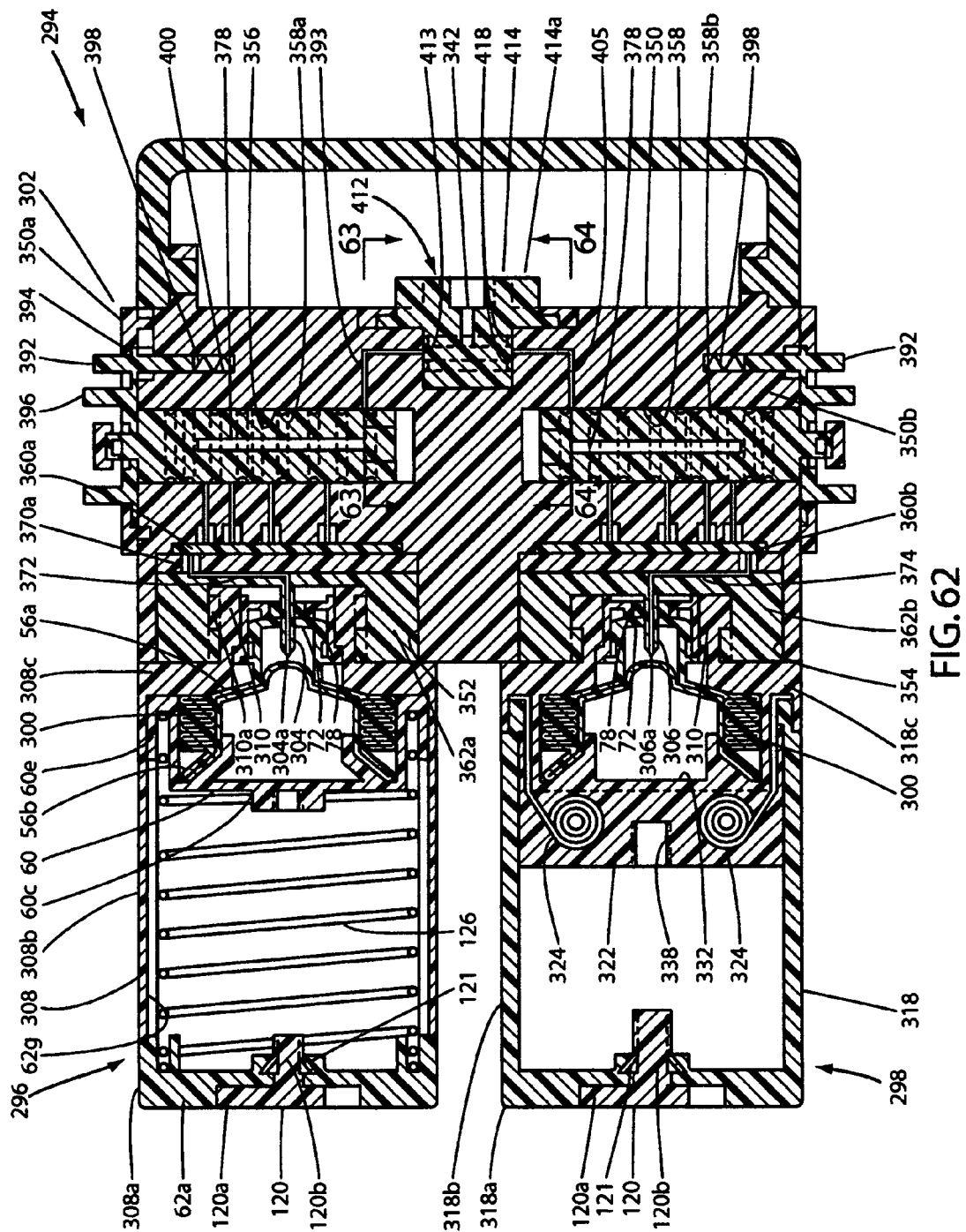
FIG. 62 is a longitudinal cross-sectional view of the fluid dispensing apparatus of the invention, similar to FIG. 59, but showing the appearance of the device following the collapse of the bellows type reservoirs of the apparatus by the stored energy means.
Figure 63:
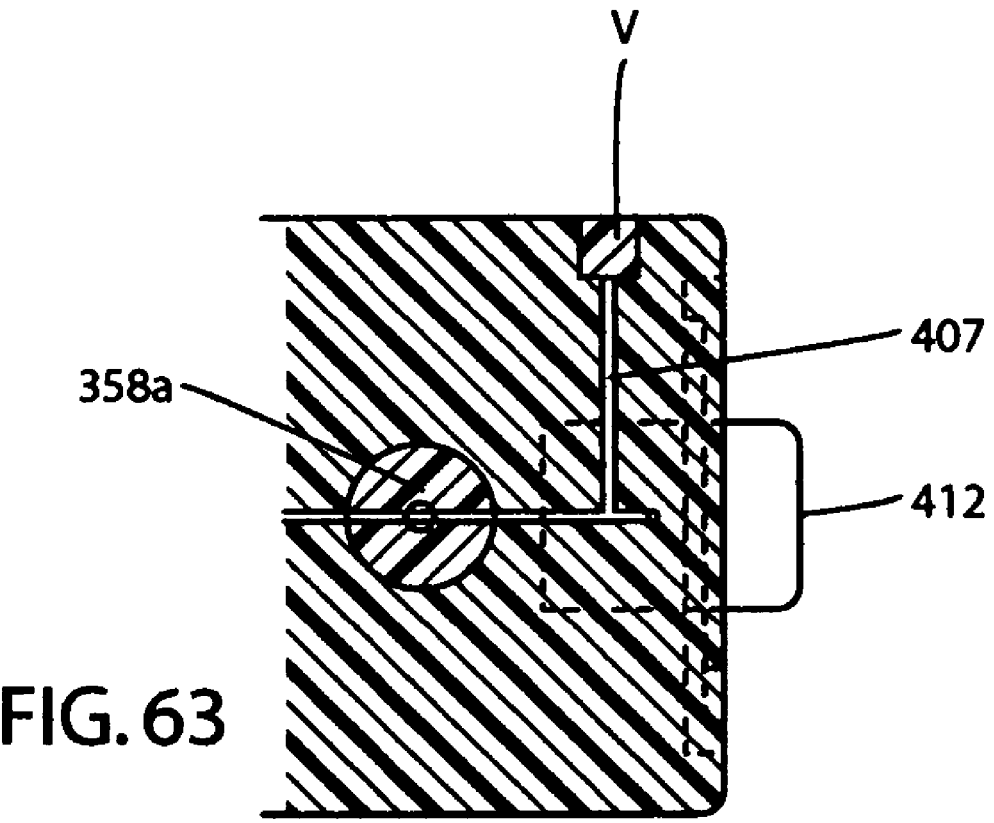
FIG. 63 is a cross-sectional view taken along lines 63-63 of FIG. 62.
Figure 64:
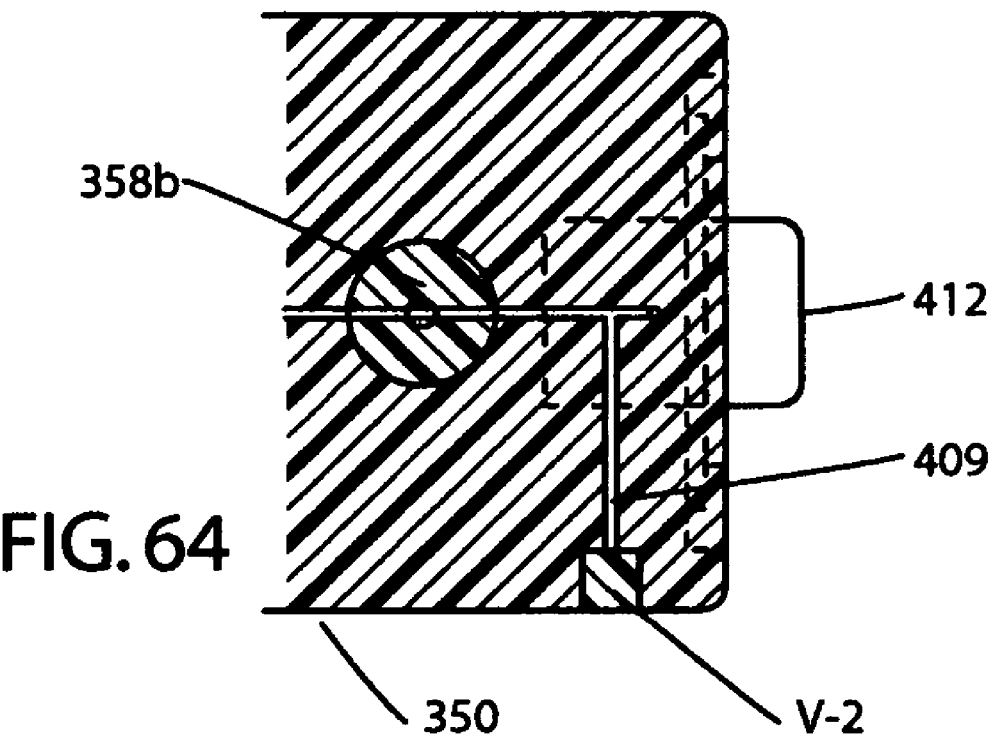
FIG. 64 is a cross-sectional view taken along lines 64-64 of FIG. 62.
Figure 75:
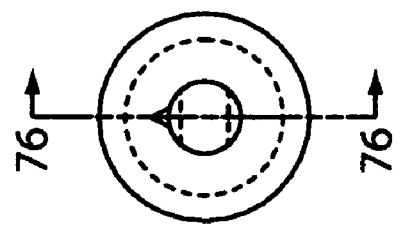
FIG. 75 is a greatly enlarged end view of the rate control shaft of one of the second stand-alone unitary fluid reservoir assemblies of the invention.

In addition to the reservoir defining component 300, assembly 296 includes a carriage 60 and a stored energy means that is operably associated with the carriage for moving the carriage between a first retracted position shown in FIG. 59 and a second advanced position shown in FIG. 62. Both the carriage 60 and a stored energy means of this latest form of the invention are substantially identical in construction and operation to those previously described herein in connection with the embodiment of FIGS. 1 through 43. As before, carriage 60 is releasably locked in its first position by a novel carriage locking means that is also substantially identical in construction and operation to that previously described herein in connection with the embodiment of FIGS. 1 through 43.

As in the earlier described embodiments of the invention, reservoir defining component 300 here comprises an integrally formed, hermetically sealed container that includes a front portion 56a, a rear portion 56b and a collapsible accordion-like, continuous, uninterrupted side wall 56c that interconnects the front and rear portion of the container. Front portion 56a, rear portion 56b and side wall 56c cooperate to define the fluid reservoir 74 of the fluid reservoir assembly.

In this latest form of the invention the fluid medicament reservoir 74 of the fluid reservoir assembly is accessible via the previously identified penetrating member 304 which forms the inlet to one side of the fluid delivery and control assembly 302. More particularly, penetrating member 304 is adapted to pierce closure wall 72 as well as the pierceable membrane 78 of the reservoir assembly that forms a part of the first reservoir component 296

Considering now the second unitary fluid reservoir assembly 298 of the fluid dispensing apparatus which is illustrated in FIG. 59 of the drawings. This assembly, which is similar in construction and operation to the first unitary fluid reservoir assembly 296, here comprises a generally cylindrically shaped housing 318 that houses the fluid reservoir defining component 300 and the stored energy means. Housing 318 includes a base 318a, an outer wall 318b and a top wall 318c. Connected to top wall 318c is a connector neck 320 having bayonet like connector grooves 320a (FIG. 59). Like connector neck 310, connector neck 320 is initially closed by a sterile barrier (not shown) that is similar to sterile barrier 64a and is removably connected to the connector neck.

In addition to the reservoir defining component 300, assembly 298 includes a carriage assembly 322 and a stored energy means that is operably associated with the carriage for moving the carriage between a first retracted position shown in FIG. 59 and a second advanced position shown in FIG. 62. Both the carriage and the stored energy means of assembly 298 of this latest form of the invention are different in construction and operation from those of assembly 296. More particularly, the stored energy means here uniquely comprises a pair of constant force springs 324 that are mounted within housing 318 in the manner shown in FIG. 65. As previously discussed, constant force springs, such as springs 324 are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force, the same as a common extension spring but at a nearly constant (zero) rate. The constant-force spring is well suited to long extensions with no load build-up. As illustrated in FIG. 65, springs 324 are mounted with one end 324a tightly wrapped on a drum 326 that is housed with a carriage block 328 and the other end 324b attached to forward portion of housing 318 in the manner shown in FIG. 59.

In this latest form of the invention, carriage assembly 322 includes a base assembly 330 that includes a forward portion having a base 332 and a reservoir receiving flange 334 (FIG. 59). Base assembly 330 also includes a rear portion having housing 336 that is provided with a threaded carriage locking member receiving cavity 338 (see also FIG. 65). Carriage assembly 322 is releasably locked in its first position by a novel carriage locking means, which is substantially identical in construction and operation to that previously described herein in connection with the embodiment of FIGS. 45 through 47.

In this latest form of the invention the fluid medicament reservoir 74 of the fluid reservoir assembly is accessible via the previously identified penetrating member 306 which forms the inlet to the other side of the fluid delivery and control assembly 302. More particularly, penetrating member 306 is adapted to pierce closure wall 72 as well as the pierceable membrane 78 of the reservoir assembly that forms a part of the second reservoir component 298.

Figure 53:
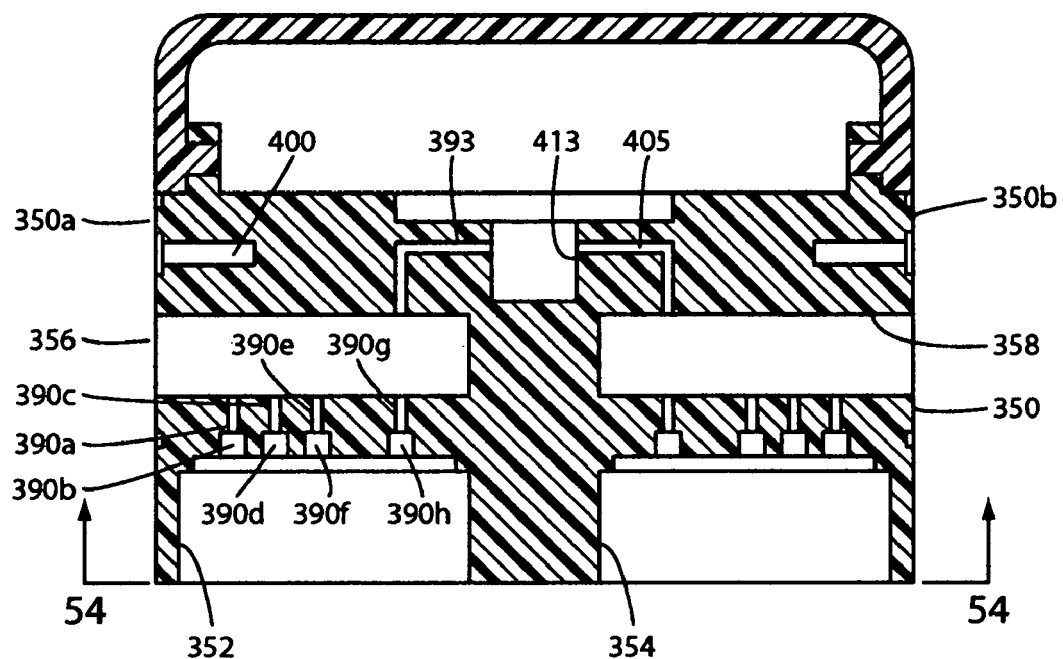
FIG. 53 is a cross-sectional view taken along lines 53-53 of FIG. 52.
Figure 54:
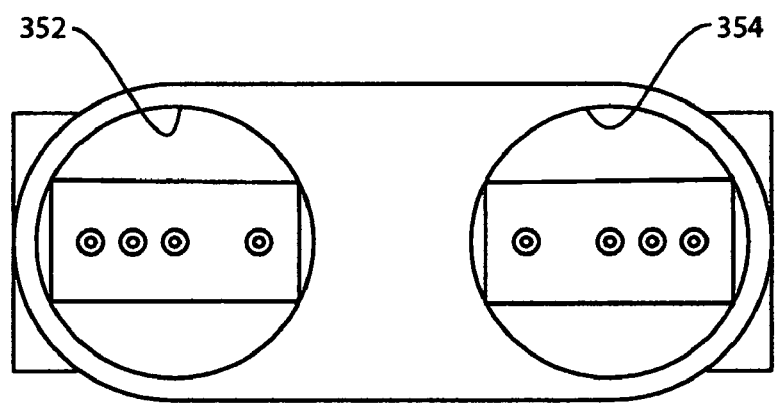
FIG. 54 is a view taken along lines 54-54 of FIG. 53.
Figure 55:
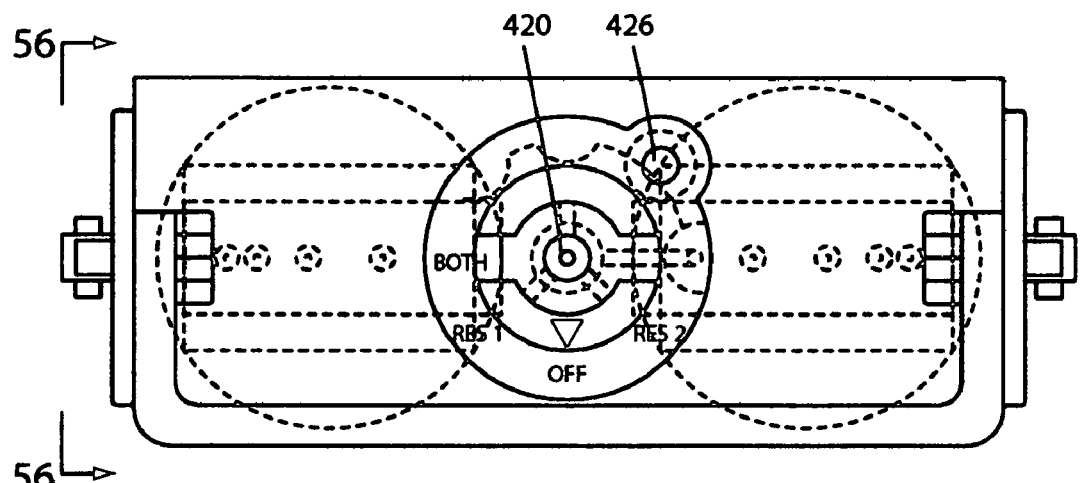
FIG. 55 is a top plan view of the stand-alone fluid delivery and control assembly of the alternate form of the two-part fluid delivery system shown in FIG. 49.
Figure 56:
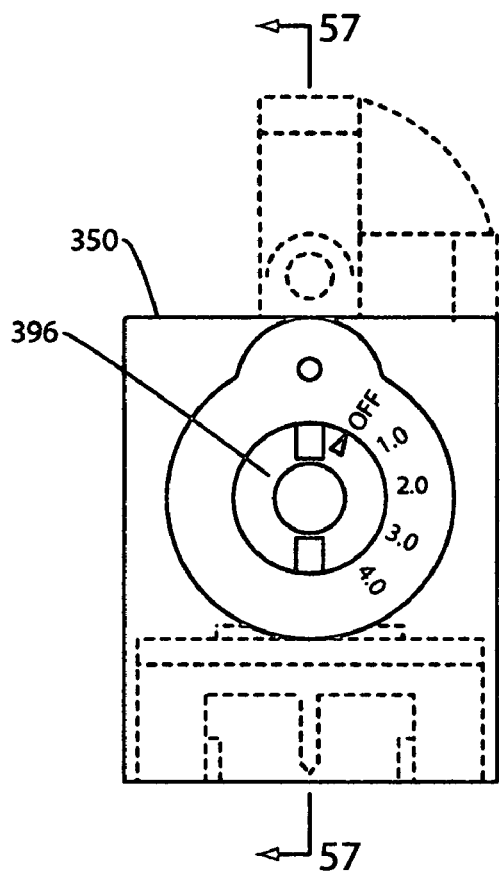
FIG. 56 is a view taken along lines 56-56 of FIG. 55.
Figure 57:
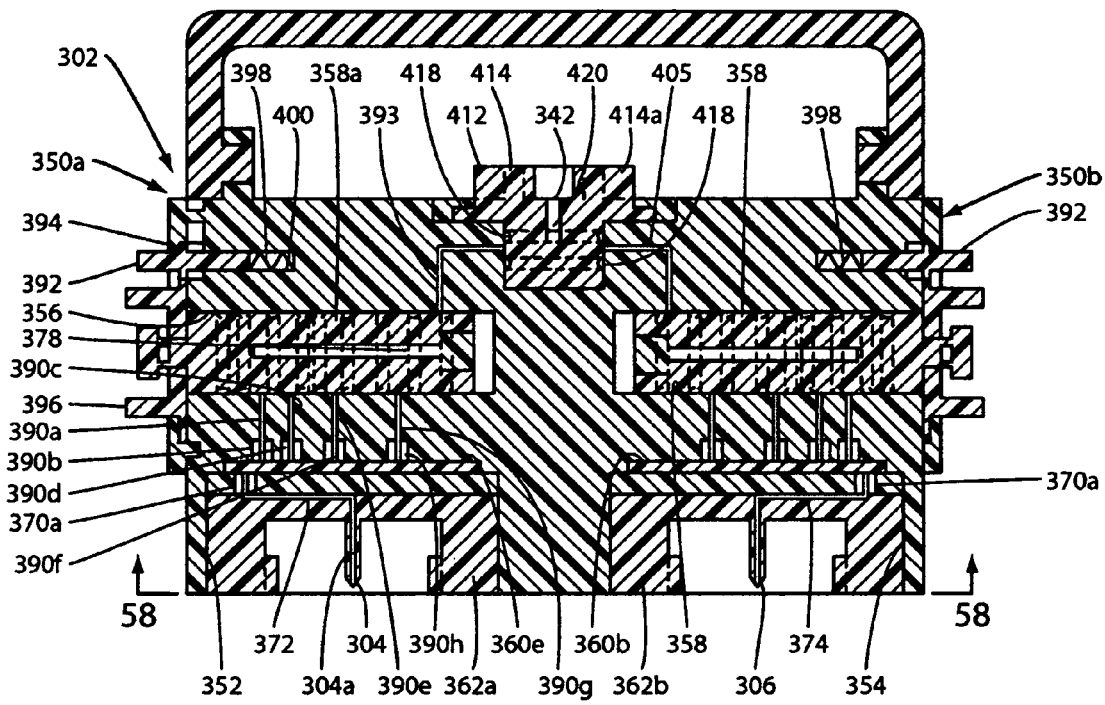
FIG. 57 is a cross-sectional view taken along lines 57-57 of FIG. 56.
Figure 58:
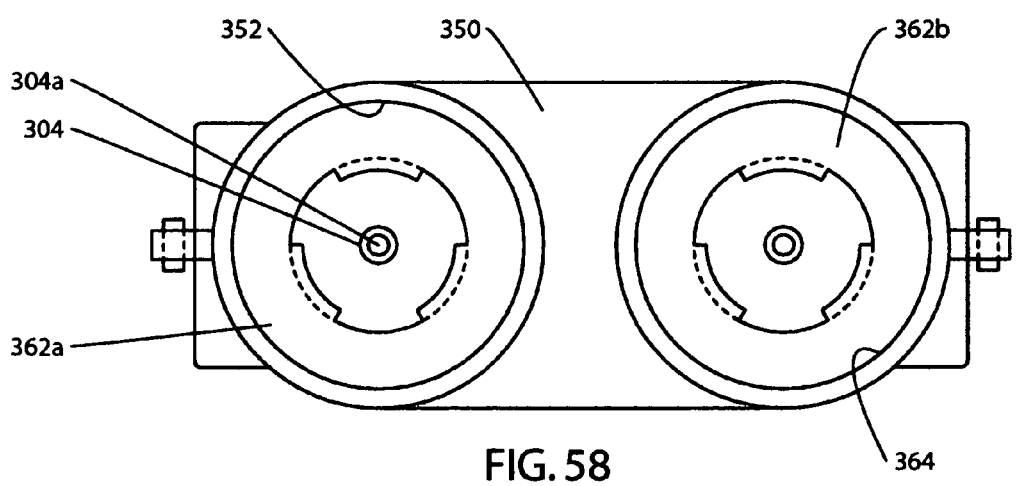
FIG. 58 is a view taken along lines 58-58 of FIG. 57.

As illustrated in FIGS. 53 and 59 of the drawings, fluid delivery and control assembly 302 of this latest form of the invention includes a housing 350 that is provided with first and second chambers 352 and 354 that, in a manner presently to be described, telescopically receive first and second unitary fluid reservoir assemblies 296 and 298 respectively (see FIG. 59). Housing 350 has a first side portion 350a that is provided with a transversely extending bore 356 that rotatably receives the first of the rate control shafts 358a of the control assembly of the invention. Similarly, housing 350 has a second side portion 350b that is provided with a transversely extending bore 358 that rotatably receives the second of the rate control shafts 358b of the control assembly of the invention (FIG. 57).

Also received within first and second chambers 352 and 354, respectively, are first and second rate control assemblies 360a and 360b. First rate control assembly 360a is held in position within first chamber 352 by a bayonet like first connector ring 362a, which carries penetrating member 304, while second rate control assembly 360b, which carries penetrating member 306 is held in position within second chamber 354 by a bayonet like second connector ring 362b. In a manner presently to be described, unitary fluid reservoir assembly 296 is inter-connectable with bayonet like first connector ring 362a, while unitary fluid reservoir assembly 298 is inter-connectable with bayonet like second connector ring 362b.

Rate control assemblies 360a and 360b, which are substantially identical in construction and operation, form a part of the flow control means of the invention and each comprises a rate control plate 366 and a rate control cover 368. As shown in FIGS. 66 through 71, rate control plate 366 is provided with circuitous fluid channels 366a, 366b, 366c and 366d, each of which is of a different geometry including channel length, depth, width and geometry. The length, width and depth of the micro-channel determine the rate at which the fluid will flow through the micro-channel and toward the patient. Rate control cover 368 covers the channels in the manner illustrated in FIGS. 66 and 67.

When reservoir assembly 296 is interconnected with bayonet-like first connector ring 362a, in the manner shown in FIG. 59, the inlet 370a of the rate control plate 366 that is mounted within portion 350a of housing 350 is in communication with penetrating member 304 via a passageway 372 formed in first connector ring 362a. Similarly, when reservoir assembly 298 is interconnected with bayonet-like first connector ring 362b, in the manner shown in FIG. 59, the inlet 370a of the rate control plate 366 that is mounted within portion 350b of housing 350 is in communication with penetrating member 306 via a passageway 374 formed in second connector ring 362b.

Because the second assembly has been sterilized in the manner previously described, passageways 372 and 374 are completely sterile at the time reservoir assemblies 296 and 298 are connected to the second assembly.

Figure 76:
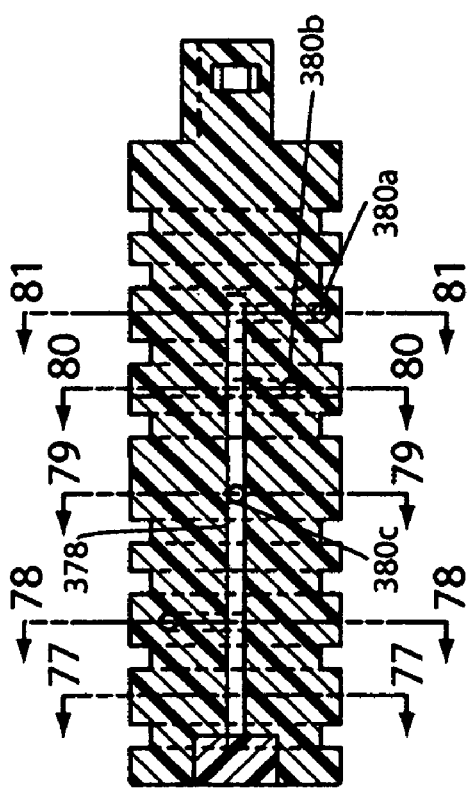
FIG. 76 is a cross-sectional view taken along lines 76-76 of FIG. 75.
Figure 81:
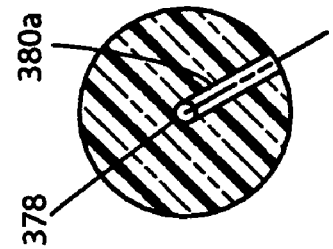
FIG. 81 is a cross-sectional view taken along lines 81-81 of FIG. 76.
Figure 80:
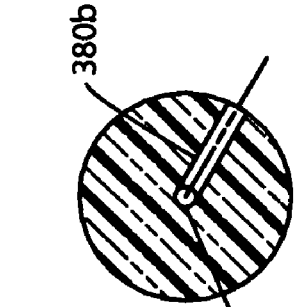
FIG. 80 is a cross-sectional view taken along lines 80-80 of FIG. 76.
Figure 79:
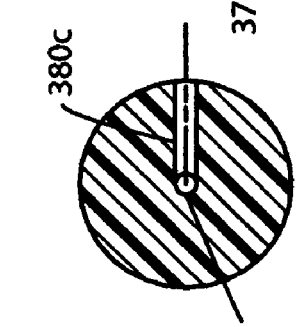
FIG. 79 is a cross-sectional view taken along lines 79-79 of FIG. 76.
Figure 78:
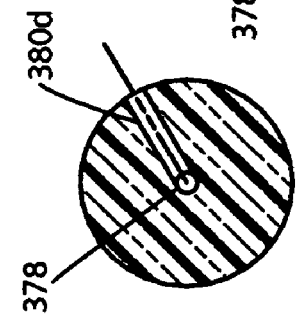
FIG. 78 is a cross-sectional view taken along lines 78-78 of FIG. 76.
Figure 77:
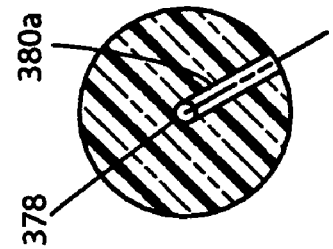
FIG. 77 is a cross-sectional view taken along lines 77-77 of FIG. 76.
Figure 82:
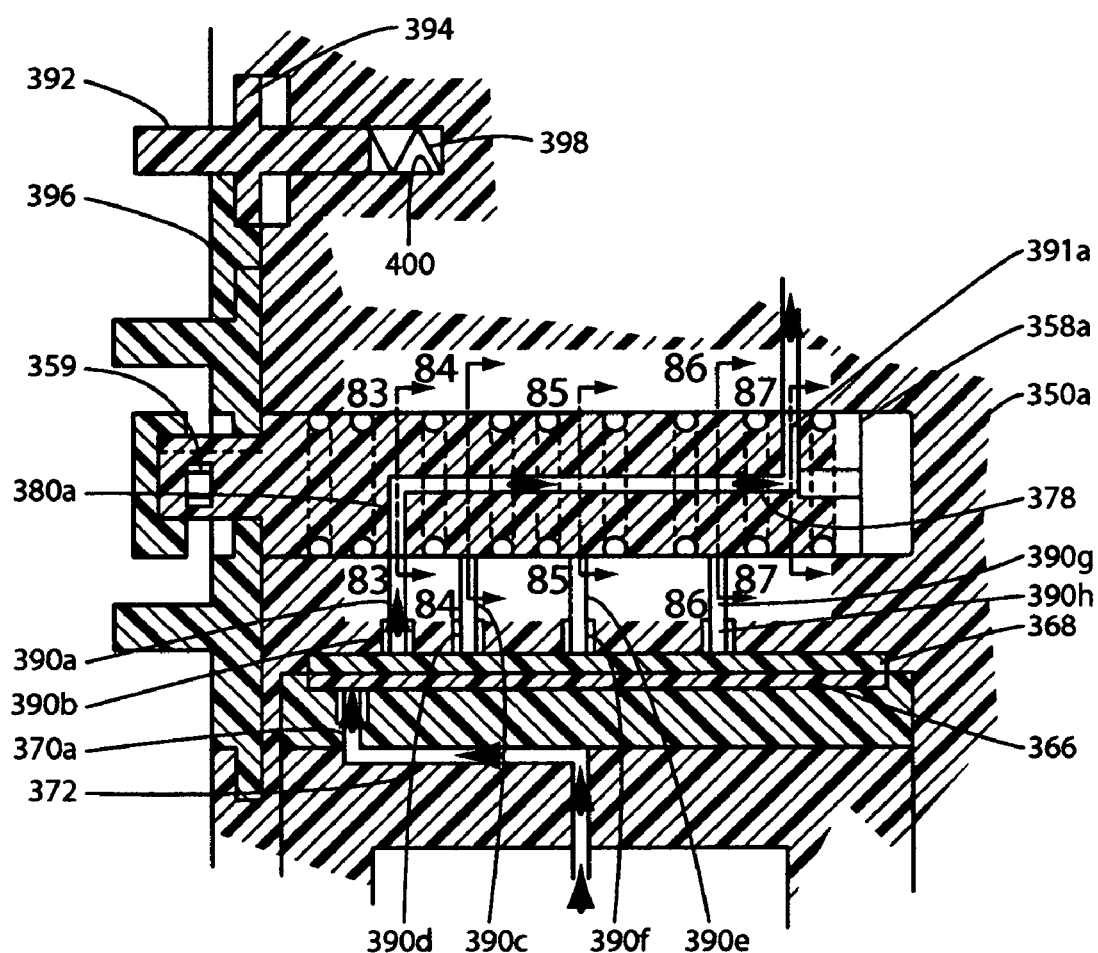
FIG. 82 is a fragmentary cross-sectional view illustrating the construction of one of the fluid rate control assemblies of the invention.
Figure 87:
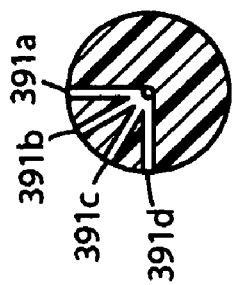
FIG. 87 is a cross-sectional view taken along lines 87-87 of FIG. 82 showing the shaft in a position blocking fluid flow through the fifth radial passageway of the shaft.
Figure 87A:
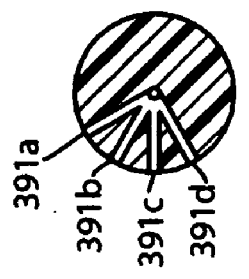
FIG. 87A is a cross-sectional view similar to FIG. 87, but showing the shaft in a position permitting fluid flow through the fifth radial passageway of the shaft.
Figure 86:
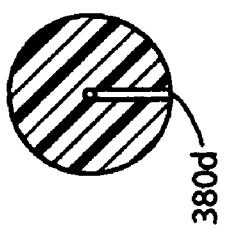
FIG. 86 is a cross-sectional view taken along lines 86-86 of FIG. 82 showing the shaft in a position blocking fluid flow through the fourth radial passageway of the shaft.
Figure 86A:
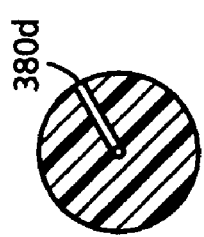
FIG. 86A is a cross-sectional view similar to FIG. 86, but showing the shaft in a position permitting fluid flow through the fourth radial passageway of the shaft.
Figure 85:
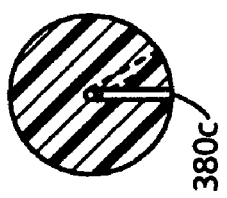
FIG. 85 is a cross-sectional view taken along lines 85-85 of FIG. 82, showing the shaft in a position blocking fluid flow through the third radial passageway of the shaft.
Figure 85A:
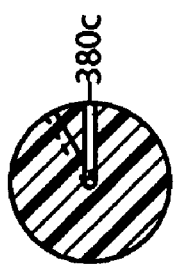
FIG. 85A is a cross-sectional view similar to FIG. 85, but showing the shaft in a position permitting fluid flow through the third radial passageway of the shaft.
Figure 84:
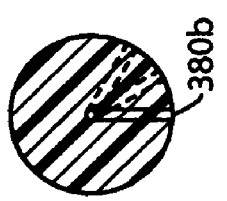
FIG. 84 is a cross-sectional view taken along lines 84-84 of FIG. 82 showing the shaft in a position blocking fluid flow through the second radial passageway of the shaft.
Figure 84A:
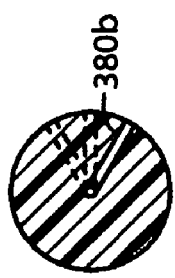
FIG. 84A is a cross-sectional view similar to FIG. 84, but showing the shaft in a position permitting fluid flow through the second radial passageway of the shaft.

Considering now in greater detail the construction and operation of the first and second rate control shafts 358a and 358b of the control assembly of the invention as shown in FIGS. 72 and 76. Each of these rate control shafts is provided with a plurality of longitudinally spaced apart O-ring grooves 377 that carry a plurality of longitudinally spaced apart O-rings 377a (FIG. 72) that circumscribe the body portion of the shaft and function to prevent fluid leakage between housing 350 and the body portion of the shaft. Additionally, each of these rate control shafts is provided with a longitudinally extending central bore 378 that communicates with the flow passageways of the previously identified penetrating members via a plurality of longitudinally spaced apart radially extending passageways 380a, 380b, 380c and 380d (see FIGS. 77 through 87A). Each of these radially extending flow passageways has an inlet that selectively communicates with the first and second rate control assemblies 360a and 360b.

In using the apparatus of the invention, the first step is to remove the sterile covers from assemblies 296 and 298. This done, the assemblies can be irreversibly interconnected with the fluid delivery and control assembly 302 in the manner illustrated in FIG. 59 by first inserting the neck of assembly 296 into the chamber of the bayonet like first connector ring 362a and rotating assembly 296 relative to first connector ring 362a. As the assemblies mate in a bayonet like connection manner penetrating member 304 will penetrate elastomeric member 78 and closure wall 72 of the container 300 of assembly 296.

With communication between the fluid reservoir 74 and the internal fluid passageway 304a of the penetrating member 304 having thusly been established, the fluid contained within the fluid reservoir 74 can be expelled from the reservoir in a manner presently to be described.

Following interconnection of assembly 296 with the fluid delivery and control assembly 302, assembly 298 can be irreversibly interconnected with the fluid delivery and control assembly 302 in the manner illustrated in FIG. 59 by first inserting the neck of assembly 298 into the chamber of the bayonet like second connector ring 362b and rotating assembly 298 relative to second connector ring 362b. As the assemblies mate in a bayonet like connection manner, penetrating member 306 will penetrate elastomeric member 78 and closure wall 72 of the container 300 of assembly 298.

With communication between the fluid reservoir 74 and the internal fluid passageway 306a of the penetrating member 306 having thusly been established, the fluid contained within the fluid reservoir can be expelled from the reservoir 74 in a manner next to be described.

To expel the fluid contained within the fluid reservoir of the container 300 of assembly 296, the carriage release member 120 of assembly 296 is controllably rotated. As before, carriage release member 120 comprises a part of the carriage locking means of assembly 296. This is accomplished by grasping the finger engaging arm 120a of the release member (FIG. 59) and rotating the member until the threaded shank 120b of the knob threadably disengages from the locking member receiving protuberance 60c. As in the previously described embodiments of the invention, release member 120 is held in position within the housing base 308a of assembly 296 by means of circumferentially spaced locking tabs 121 provided on shank 120b. Once the carriage release member is free from the locking member receiving protuberance, the stored energy means here shown as a coil spring 126, will urge the carriage forwardly in the manner illustrated in FIG. 62 of the drawings. As the carriage moves forwardly, the circumferentially spaced guide tabs 60e formed on the carriage will slide within and be guided by guide channel 62g formed in housing 308b. As the accordion side walls collapse, the fluid will be forced outwardly of the reservoir 74 into internal passageway 304a of the penetrating member. In the manner previously described, the fluid will then flow toward the fluid flow control means of this latest form of the invention. More particularly, as the fluid flows from reservoir 74 into the inlet 384 of rate control plate 366 via the orifice 370a of the rate control plate 366, each of the circuitous fluid channels 366a, 366b, 366c and 366d (see FIGS. 70 and 71) will fill with the medicinal fluid to be dispensed to the patient via rate control plate passageway 385 (FIG. 70).

To enable the fluid to flow from the rate control plate of assembly 360a to the patient via the reservoir selector means of the invention and the administration set 130 (FIG. 49), the fluid control locking means must be operated in the manner presently to be described.

As shown in FIG. 49 of the drawings, the administration set 130 is sealably interconnected with an outlet port 341 of the important reservoir selector means of the invention, the character of which will presently be described. Disposed between the proximal end and the distal end 136b of the administration line are a conventional clamp 140, a conventional gas vent and filter 142, and a generally Y-shaped injection site, generally designated by the numeral 144. A luer connector 146 of conventional construction is provided at the distal end 136b of the administration line.

To expel the fluid contained within the fluid reservoir of the container 300 of assembly 298, the carriage release member 120 of assembly 298 is controllably rotated. As before, carriage release member 120 comprises a part of the carriage locking means of assembly 298. This is accomplished by grasping the finger engaging arm 120a of the release member (FIG. 59) and rotating the member until the threaded shank 120b of the knob threadably disengages from the locking member receiving protuberance 60c. As in the previously described embodiments of the invention, release member 120 is held in position within the housing base 318a of assembly 298 by means of circumferentially spaced locking tabs 121 provided on shank 120b. Once the carriage release member is free from the locking member receiving protuberance, the stored energy means, here shown as a pair of constant force springs 324 will urge the carriage forwardly in the manner illustrated in FIG. 62 of the drawings. As the carriage moves forwardly, the circumferentially spaced guide tabs 60e formed on the carriage will slide within and be guided by guide channel 62g formed in housing 62. As the accordion side walls collapse, the fluid will be forced outwardly of the reservoir into internal passageway 306a of the penetrating member. In the manner previously described, the fluid will then flow toward the fluid flow control means of this latest form of the invention. More particularly, as the fluid flows from reservoir 74 into the inlet 384 of rate control plate 366 that is disposed within the second portion 350b of the housing via the orifice 370a of the rate control plate 366, each of the circuitous fluid channels 366a, 366b, 366c and 366d of this rate control plate (see FIGS. 70 and 71) will fill with the medicinal fluid to be dispensed to the patient via rate control plate passageway 385 (FIG. 70).

To enable the fluid to flow from the rate control plate of each of the assemblies 296 and 298 to the patient via the reservoir selector means and the administration set 130 (FIG. 49), the fluid control locking means must be operated in the manner presently to be described.

Figure 83:
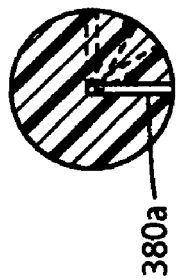
FIG. 83 is a cross-sectional view taken along lines 83-83 of FIG. 82 showing the shaft in a position blocking fluid flow through the first radial passageway.
Figure 83A:
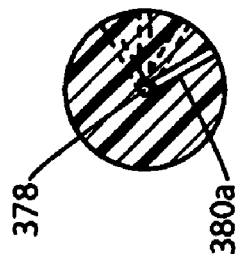
FIG. 83A is a cross-sectional view similar to FIG. 83, but showing the shaft in a position permitting fluid flow through the first radial passageway of the shaft.

Because the operation of each of the rate control shafts 358a and 358b and their relationship with their respective rate control assemblies is substantially the same, only the operation rate control shaft 358a will be described with the understanding that rate control shaft 358b operates in the same manner to allow fluid flow to the patient via the reservoir selector means and the administration set 130. To permit fluid flow from the rate control micro-channel 366a toward passageway 380a, the rate control shaft 358a must be rotated to a position wherein radial flow passageway 380a aligns with an outlet passageway 390a formed in housing portion 350a. Outlet passageway 390a is in communication with an outlet 390b formed on rate control cover 368 (FIGS. 57 and 82), which outlet communicates with micro channel 366a. With the rate control shaft 358a in this position, fluid can flow through the micro-channel at a controlled, fixed rate depending upon the configuration of the channel, into outlet 390b, into outlet passageway 390a, then into radial passageway 380a and finally into the longitudinal passageway 378 formed in the rate control shaft. From passageway 378 the fluid will flow out of the rate control shaft through a passageway 391a (FIG. 83A) and into a passageway 393 formed in housing portion 350a (FIG. 57). In a manner presently to be described, the fluid will then flow toward the administration set via the important reservoir selector means of the invention.

As previously mentioned, rotation of neither of the rate control shafts 358a and 358b can be accomplished until their respective rate control shaft locking means is operated by the caregiver. In the present form of the invention the locking means that controls rotation of shaft 358a is substantially identical in construction and operation to the locking means that controls rotation of shaft 358b. Each of the novel locking means here comprises a plunger 392 that includes a locking collar 394 (FIGS. 50 and 82) that prevents rotation of the rate control selector disk 396 and of the rate control shaft to which the disk is connected, unless and until the plunger 392 is moved inwardly of the housing against the urging of a biasing means shown here as coil spring 398 that is housed within a chamber 400 formed in housing portion 350a, or 350b. Once the plunger is appropriately urged inwardly, collar 394 moves out of one of the plurality of circumferentially spaced, semi-circular shaped retainer apertures 402a, 402b, 402c, 402d and 402e formed in the periphery of the rate control selector disk 396, thereby permitting rotation of the rate control selector disk 396 and of the rate control shaft (FIG. 73).

Once the rate control shaft locking means has been operated in the manner described in the preceding paragraph to move the locking collar 394 out of retainer aperture 402a (the "off" aperture) and into aperture 402b (FIG. 73), fluid flow from the rate control micro-channel 366a toward passageway 390a via outlet 390b can be achieved by rotating the rate control shaft 358a in the manner previously described. Similarly, fluid flow from the rate control micro-channel 366b toward passageway 390c via outlet 390d can be achieved by pushing the plunger 392 inwardly of the housing against the urging of the biasing means, so that collar 394 can be moved out of the retainer aperture wherein it resides and into aperture 402c (FIG. 73). In this position radial flow passageway 380b aligns with outlet passageway 390c formed in housing portion 350a and with outlet 390d, which outlet communicates with micro channel 366b. With the rate control shaft 358a in this position, fluid can flow through micro-channel 366b at a controlled, fixed rate depending upon the configuration of the channel, into outlet 390d, into outlet passageway 390c, then into radial passageway 380b and finally into the longitudinal passageway 378 formed in the rate control shaft. From passageway 378 the fluid will flow out of the rate control shaft through a passageway 391b (FIG. 87A) and into a passageway 393 formed in housing portion 350a. In a manner presently to be described, the fluid will then flow toward the administration set via the important reservoir selector means of the invention.

In a similar manner, fluid flow from the rate control micro-channel 366c toward passageway 390e via outlet 390f can be achieved by pushing the plunger 392 inwardly of the housing against the urging of the biasing means, so that collar 394 can be moved out of the retainer aperture wherein it resides and into aperture 402d (FIG. 73). In this position, radial flow passageway 380c aligns with outlet passageway 390e formed in housing portion 350a and with outlet 390f, which outlet communicates with micro channel 366c. With the rate control shaft 358a in this position fluid can flow through micro-channel 366c at a controlled, fixed rate depending upon the configuration of the channel, into outlet 390f, into outlet passageway 390e, then into radial passageway 380c and finally into the longitudinal passageway 378 formed in the rate control shaft. From passageway 378 the fluid will flow out of the rate control shaft through a passageway 391c (FIG. 87A) and into a passageway 393 formed in housing portion 350a. In a manner presently to be described, the fluid will then flow toward the administration set via the important reservoir selector means of the invention.

Finally, fluid flow from the rate control micro-channel 366d toward passageway 390g via outlet 390h can be achieved by pushing the plunger 392 inwardly of the housing against the urging of the biasing means, so that collar 394 can be moved out of the retainer aperture wherein it resides and into aperture 402e (FIG. 73). In this position radial flow passageway 380d aligns with outlet passageway 390g formed in housing portion 350a and with outlet 390h, which outlet communicates with micro channel 366d. With the rate control shaft 358a in this position, fluid can flow through micro-channel 366d at a controlled, fixed rate depending upon the configuration of the channel, into outlet 390h, into outlet passageway 390g, then into radial passageway 380d and finally into the longitudinal passageway 378 formed in the rate control shaft. From passageway 378 the fluid will flow out of the rate control shaft through a passageway 391d (FIG. 87A) and into a passageway 393 formed in housing portion 350a. In a manner presently to be described, the fluid will then flow toward the administration set via the important reservoir selector means of the invention.

Figure 60:
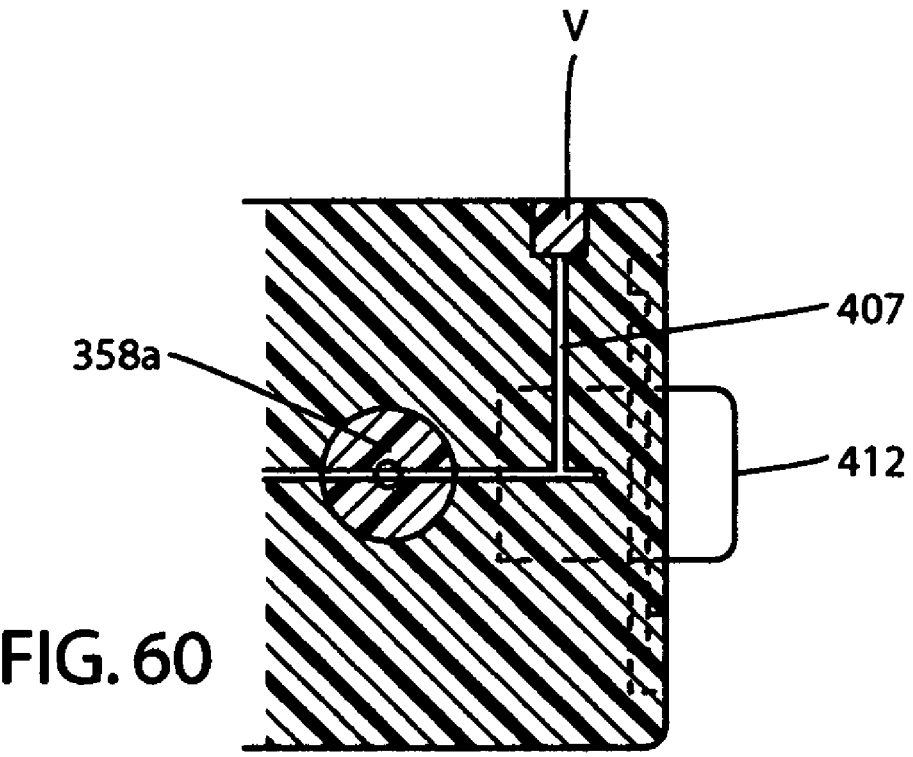
FIG. 60 is a cross-sectional view taken along lines 60-60 of FIG. 59.
Figure 61:
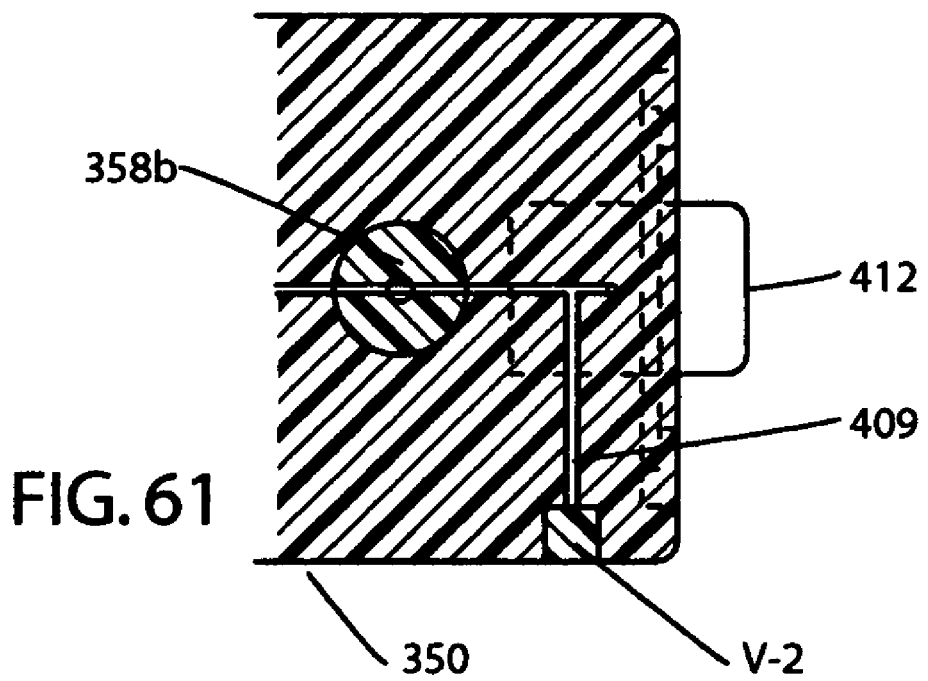
FIG. 61 is a cross-sectional view taken along lines 61-61 of FIG. 59.

During the fluid delivery step, any gases contained within the reservoir of the unitary fluid reservoir assembly 296 and the various fluid passageways are vented to atmosphere via vent port "V" and passageway 407 (FIG. 60). Similarly, during the fluid delivery step, any gases contained within the reservoir of the unitary fluid reservoir assembly 298 and the various fluid passageways are vented to atmosphere via vent port "V-1" and passageway 409 (FIG. 61).

The rate control shafts 358a and 358b can be disabled by disabling means of the character shown in FIGS. 72, 73 and 74. This disabling means here comprises a generally yoke-shaped disabling member 359 that is slidably mounted to the forward portion of the rate control shafts in the manner illustrated in FIGS. 72 and 73. By pushing the disabling member inwardly relative to the rate control shaft, the disabling member will effectively prevent rotation of the disabling shaft, thereby disabling its operation.

As previously discussed, because the operation of each of the rate control shafts 358a and 358b and their relationship with their respective rate control assemblies is substantially the same, only the operation rate control shaft 358a has been described. However, rate control shaft 358b operates in the same manner to allow fluid flow to the patient via a passageway 405 formed in housing portion 350b, via the reservoir selector means and via the administration set 130.

As illustrated in FIG. 57 of the drawings, as a result of the controlled rotation of shafts 358a and 358b, fluid will flow at a precisely controlled rate from passageways 393 and 405 toward the novel reservoir selector means of the invention. In the present form of the invention the reservoir selector means comprises a selector knob 412 that is rotatably mounted within a chamber 413 formed in housing 350 in the manner shown in FIG. 57 of the drawings. Knob 412 includes a head portion 414 having finger gripping wings 414a, a flange 414b and a generally cylindrically shaped shaft portion 416 (FIGS. 88 and 89). Shaft portion 416 is provided with a plurality of spaced apart grooves 417 for receiving a plurality of conventional O-rings 418 (FIG. 57) which function to prevent fluid leakage between the shaft portion and chamber 413 and within which the shaft portion 416 of the selector knob is disposed. For a purpose presently to be described, shaft portion 416 is also provided with an axially extending outlet passageway 420 having the outlet 342 and a plurality of longitudinally spaced, radially extending fluid passageways 422a, 422b and 422c that communicate with outlet passageway 420 (FIGS. 90, 91 and 92).

In operation, when the selector knob 412 is in the position shown in FIGS. 91A, 92A and 93B, fluid can flow from both of the reservoirs of the fluid reservoir components 296 or 298 via passageways 393 and 405 respectively, into axially extending passageway 420 via radial passageway 422a and then onto the administration set, which is in communication with passageway 420 in the manner illustrated in FIG. 49 of the drawings. However, when the selector knob is turned to the position shown in FIGS. 91B, 92B and 93C wherein fluid flow through passageway 422a is blocked and wherein passageway 422b in communication with passageway 393 of reservoir component 296, fluid can flow from the reservoir of the fluid reservoir component 296 through passageway 422b and onward to the administration set via passageway 420. Similarly, when the selector knob is turned to the position shown in FIGS. 91C, 92C and 93C wherein passageway 422c is in communication with passageway 405, fluid can flow only from the fluid reservoir of reservoir component 298 through passageway 422c and onward to the administration set via passageway 420. On the other hand, when the selector knob is turned to the position shown in FIGS. 91D, 92D and 93D fluid flow through all of the passageways is blocked and no fluid can flow from the fluid reservoir of either of the reservoir components 296 and 298 toward the administration set.

Notwithstanding the forgoing, it is to be understood that rotation of the selector knob 412 cannot be accomplished until the selector knob locking means is operated by the caregiver. In the present form of the invention the selector knob locking means here comprises a plunger 426 that includes a locking collar 428 (FIG. 50) that prevents rotation of the selector knob unless and until the plunger 426 is moved inwardly of the housing against the urging of a biasing means shown here as coil spring 430 that is housed within a chamber 432 formed in housing portion 350b. Once the plunger is appropriately urged inwardly, collar 428 moves out of one of the plurality of circumferentially spaced, semicircular shaped retainer apertures 434, 434a, 434b and 434c formed in the periphery of the flange 414b of the top portion of the selector knob 412, thereby permitting selective rotation of the selector knob.

With the construction described in the preceding paragraphs, it is apparent that, depending upon the position of reservoir selection knob 412, fluid can be delivered to the patient via the reservoir selector means in the administration set from the fluid reservoir of the unitary fluid reservoir assembly 296 at various rates of fluid flow, depending upon the position of rate control shaft 358*a*. Similarly, depending upon the position of reservoir selection knob 412, fluid can be delivered to the patient via the reservoir selector means and the administration set from the fluid reservoir of the unitary fluid reservoir assembly 298 at various rates of fluid flow depending upon the position of rate control shaft 358*b*. Additionally, depending upon the position of reservoir selection knob 412, fluid can be delivered to the patient via the reservoir selector means and the administration set simultaneously from both the fluid reservoirs of the unitary fluid reservoir assemblies 296 and 298 at various rates of fluid flow, depending upon the position of rate control shaft 358*a*.

Figure 94:
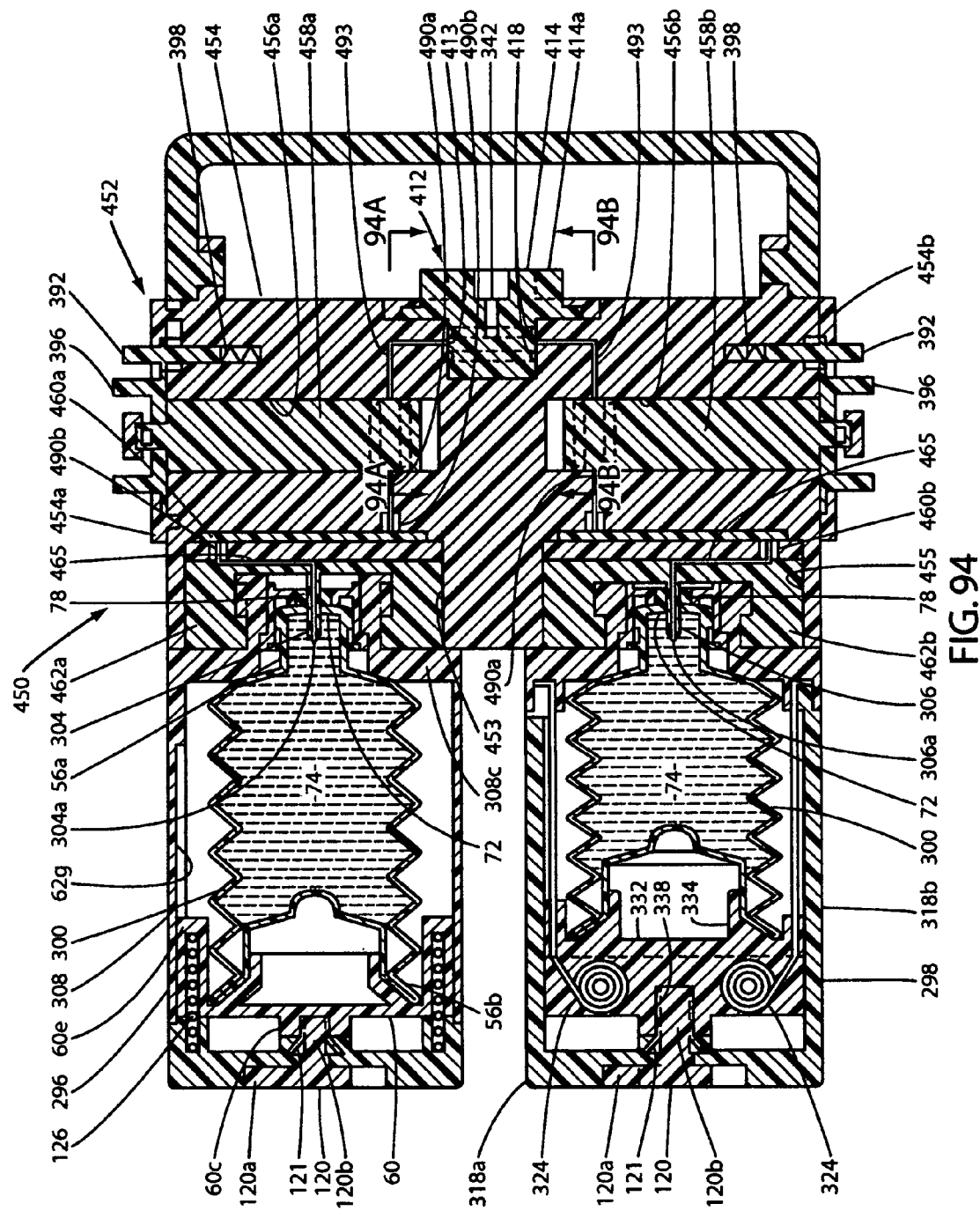
FIG. 94 is a longitudinal cross-sectional view of still another form of the fluid delivery system of the present invention, wherein the first and second stand-alone unitary fluid reservoir assembly components of the invention have been operably interconnected with the fluid delivery and control assembly.

Turning next to FIG. 94 of the drawings, still another embodiment of the invention is there shown and generally designated by the numeral 450. This alternate form of dispensing apparatus is similar in many respects to the embodiment of the invention illustrated in FIGS. 49 through 93 and like numerals are used in FIGS. 94 through 109 to identify like components. The primary difference between this latest form of the invention and that shown in FIGS. 49 through 93 resides in the fact that fluid is delivered to the patient at a fixed, rather than a variable rate.

As before, the dispensing apparatus here uniquely comprises two unitary fluid reservoir assemblies 296 and 298 which are substantially identical in construction and operation to the fluid reservoir assemblies previously described in connection with the embodiment of the invention illustrated in FIGS. 49 through 93. As illustrated in FIG. 94 of the drawings, the dispensing apparatus is also similar in many respects to the embodiment of the invention illustrated in FIGS. 49 through 93 and here comprises a fluid delivery and control assembly 452 that includes two spaced apart penetrating members 304 and 306 and a novel fluid flow control means that functions to control the flow of medicinal fluid toward the patient at a predetermined fixed rate. As before, the fluid delivery and control assembly 452 of this latest form of the invention includes a housing 454 that is provided with first and second chambers 453 and 455 that telescopically receive first and second unitary fluid reservoir assemblies 296 and 298 respectively (see FIG. 94).

Figure 102:
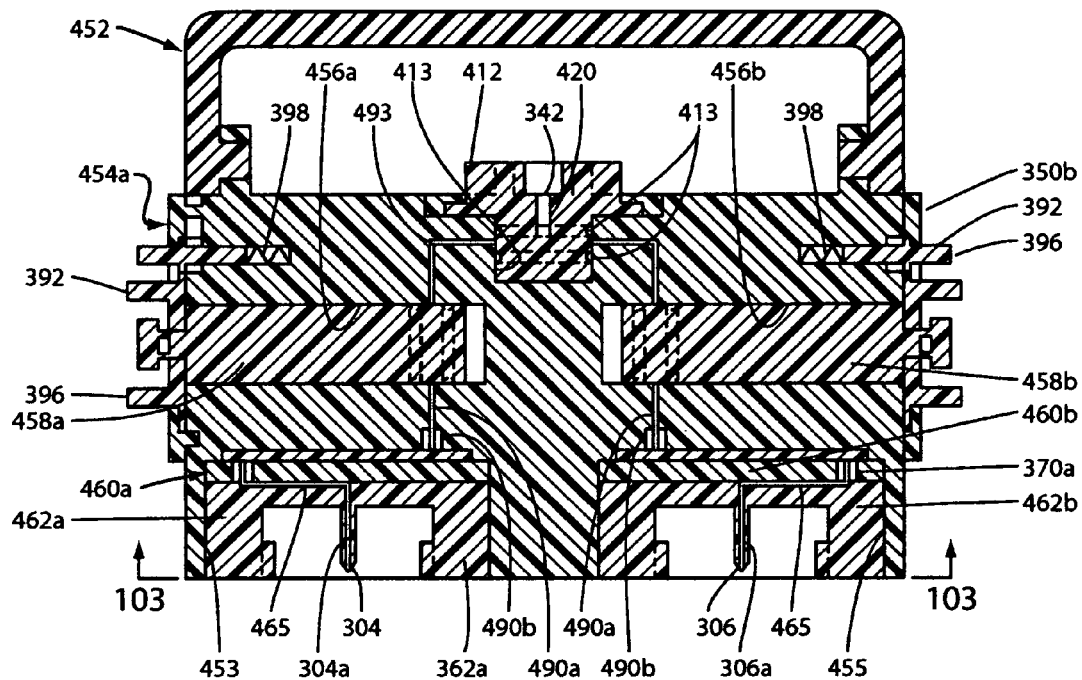
Figure 103:
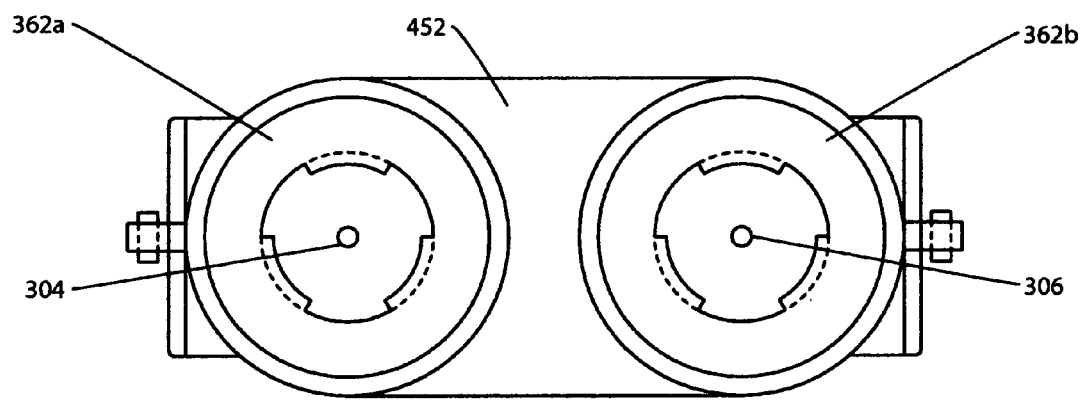

Housing 454 has a first side portion 454*a* that is provided with a transversely extending bore 456*a* that rotatably receives the first of the rate control shafts 458*a* of the control assembly of the invention. Similarly, housing 454 has a second side portion 454*b* that is provided with a transversely extending bore 456*b* that rotatably receives the second of the rate control shafts 458*b* of the control assembly of the invention (FIG. 102).

Also received within first and second chambers 453 and 455, respectively, are first and second rate control assemblies 460*a* and 460*b*. First rate control assembly 460*a* is held in position within first chamber 453 by a bayonet-like first connector ring 462*a*, which carries penetrating member 304, while second rate control assembly 460*b*, which carries penetrating member 306 is held in position within second chamber 455 by a bayonet-like second connector ring 462*b*. Unitary fluid reservoir assembly 296 is inter-connectable with bayonet-like first connector ring 462*a*, while unitary fluid reservoir assembly 298 is inter-connectable with bayonet-like second connector ring 462*b*.

Rate control assemblies 460*a* and 460*b*, which are substantially identical in construction and operation, form a part of the flow control means of this latest form of the invention and each comprises a rate control plate 466 and a rate control cover 468. As shown in FIGS. 104 through 109, rate control plate 466 is provided with a single fluid channel 466*a* of a predetermined length, depth, width and geometry. The length, width and depth of the micro-channel determine the rate at which the fluid will flow through the micro-channel and toward the patient. Rate control cover 468 covers the channels in the manner illustrated in FIG. 104.

Figure 104:
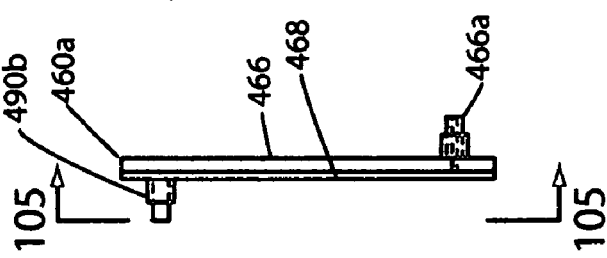
Figure 105:
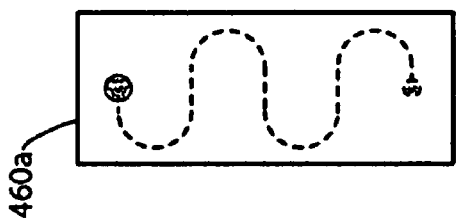

In the manner previously described, to expel the fluid contained within the fluid reservoirs of assemblies 296 and 298, the carriage release member 120 of each assembly is controllably rotated. Once the carriage release member is free from the locking member receiving protuberance, the stored energy means of the assembly will urge the carriage forwardly in the manner illustrated in FIG. 95 of the drawings. As the accordion side walls of the containers collapse, the fluid contained therein will be forced outwardly of the reservoir into the internal passageways of the penetrating members. From these internal passageways the fluid will flow via passageways 465 into the inlets 466*a* of the covers 466 of the fluid flow control means of the invention (FIGS. 94 and 104). However, as before, to enable the fluid to flow to the patient from the flow control means of each of the assemblies 296 and 298 via the reservoir selector means and the administration set 130 (FIG. 49), the fluid control locking means must be operated in the manner previously described.

Because the operation of each of the rate control shafts 458*a* and 458*b* and their relationship with their respective rate control assemblies is substantially the same, only the operation rate control shaft 458*a* will be described with understanding that rate control shaft 458*b* operates in the same manner to allow fluid flow to the patient via the reservoir selector means and the administration set 130. To permit fluid flow from the rate control micro-channel 466*b* toward passageway 480*a*, the rate control shaft 458*a* must be rotated to a position wherein radial flow passageway 480*a* (FIG. 109A) aligns with an outlet passageway 490*a* formed in housing portion 454*a*. As illustrated in FIGS. 94 and 104, outlet passageway 490*a* is in communication with an outlet 490*b*, formed on rate control cover 468, which outlet communicates with micro channel 466*b*. With the rate control shaft 458*a* in this position fluid can flow through the micro-channel at a controlled, fixed rate depending upon the configuration of the channel, into outlet 490*b*, into outlet passageway 490*a*, then into the radial passageway 480*a* of the rate control shaft. From passageway 480*a* the fluid will flow out of the rate control shaft through a passageway 493 formed in housing portion 454*b* (FIGS. 94 and 102). In the manner previously described, the fluid will then flow toward the administration set via the reservoir selector means which is substantially identical in construction and operation to the reservoir selector means previously described in connection with the embodiment of the invention illustrated in FIGS. 49 through 93.

Figure 94A:
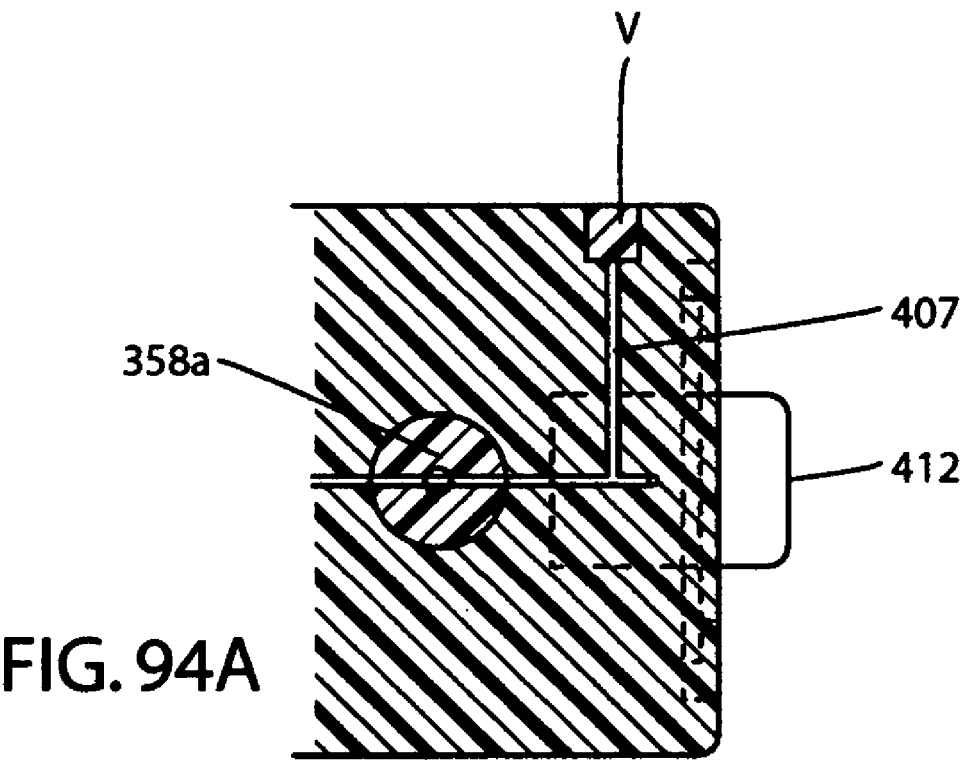
FIG. 94A is a cross-sectional view taken along lines 94A-94A of FIG. 94.
Figure 94B:
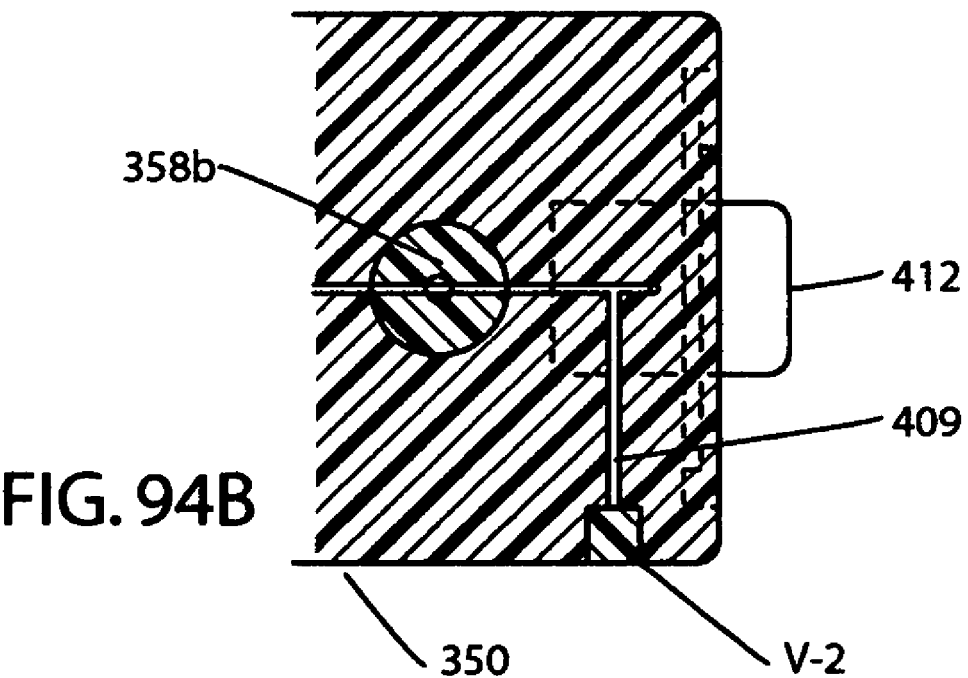
FIG. 94B is a cross-sectional view taken along lines 94B-94B of FIG. 94.
Figure 95:
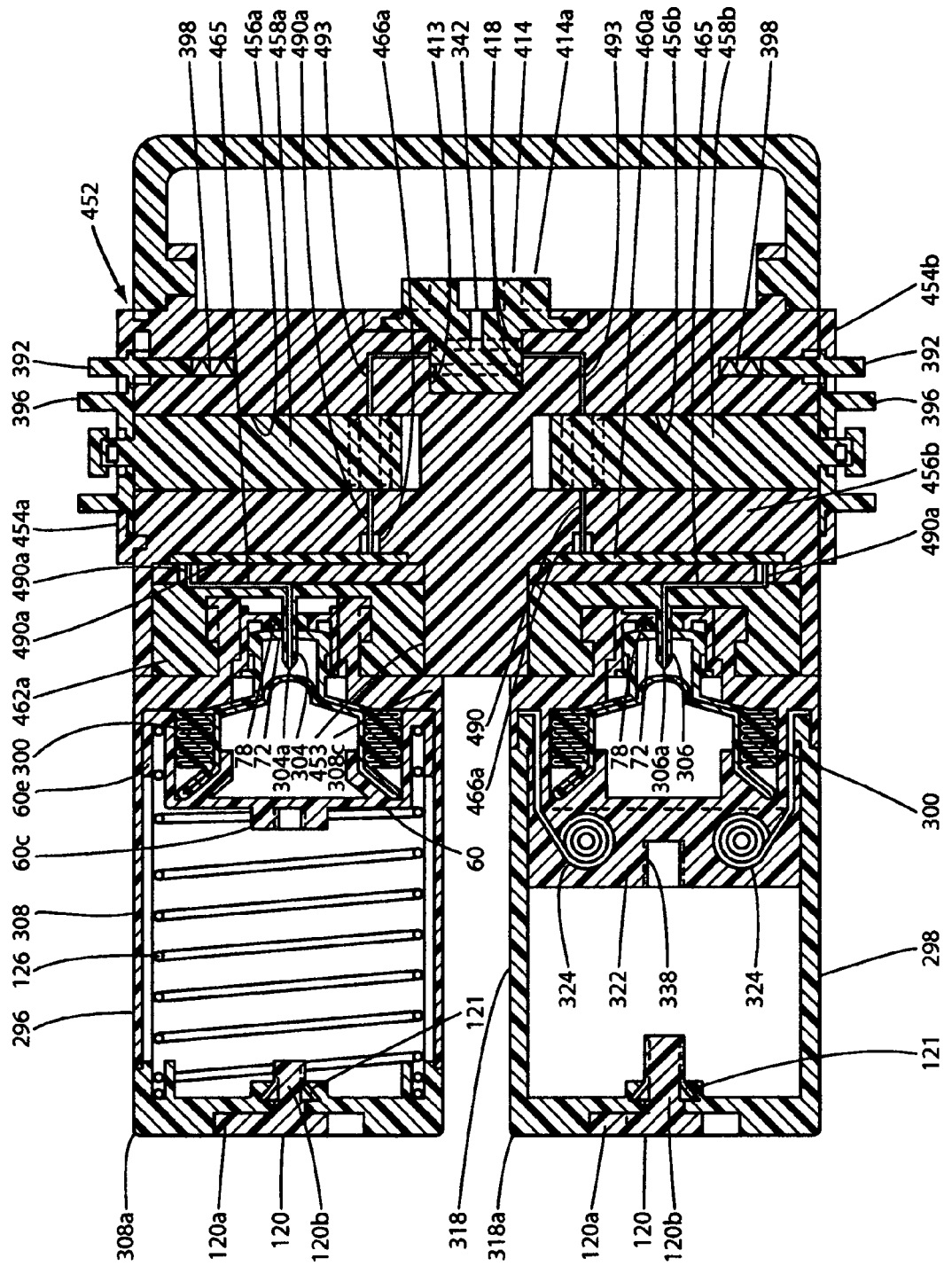
FIG. 95 is a longitudinal cross-sectional view of the fluid dispensing apparatus of the invention, similar to FIG. 94, but showing the appearance of the device following the collapse of the bellows type reservoirs of the apparatus by the stored energy means.
Figure 96:
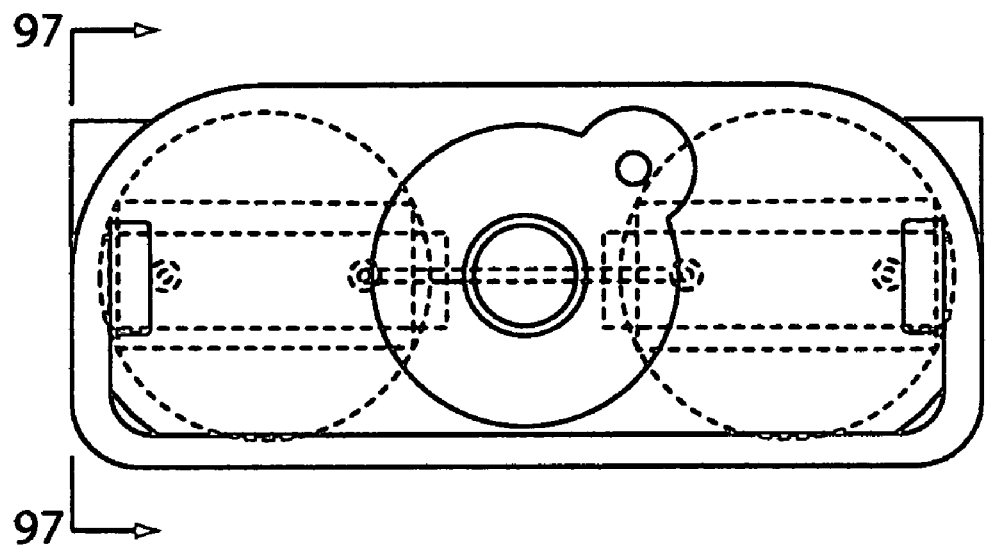
FIG. 96 is a top plan view of the housing of the stand-alone fluid delivery and control component of the alternate form of the two-part fluid delivery system shown in FIG. 94.
Figure 97:
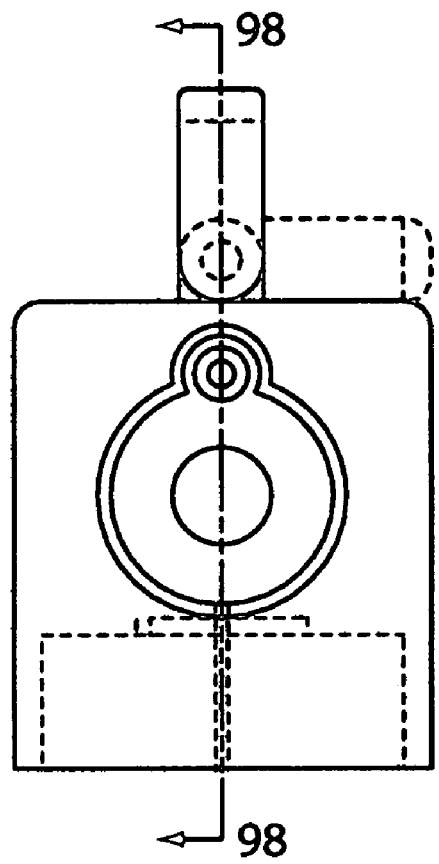
FIG. 97 is a view taken along lines 97-97 of FIG. 96.
Figure 98:
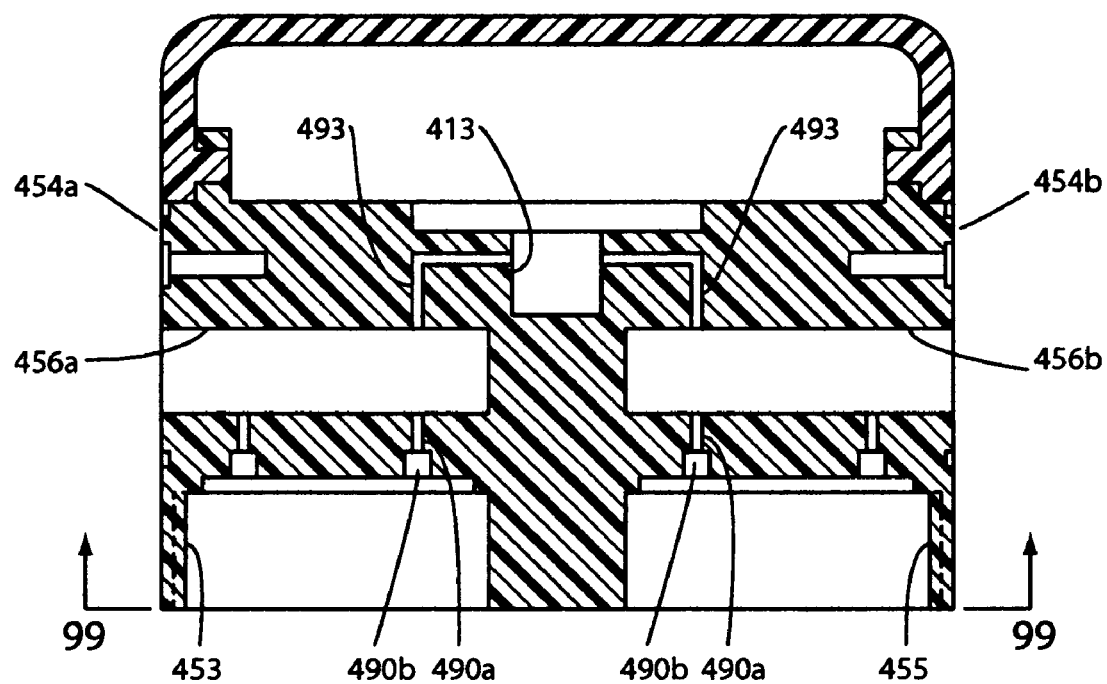
FIG. 98 is a cross-sectional view taken along lines 98-98 of FIG. 97.
Figure 99:
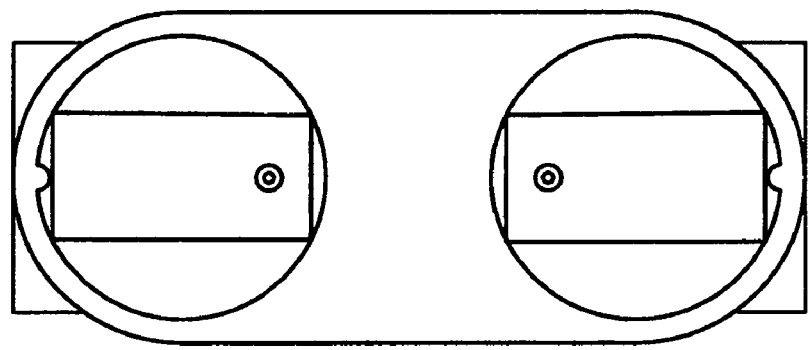
Figure 100:
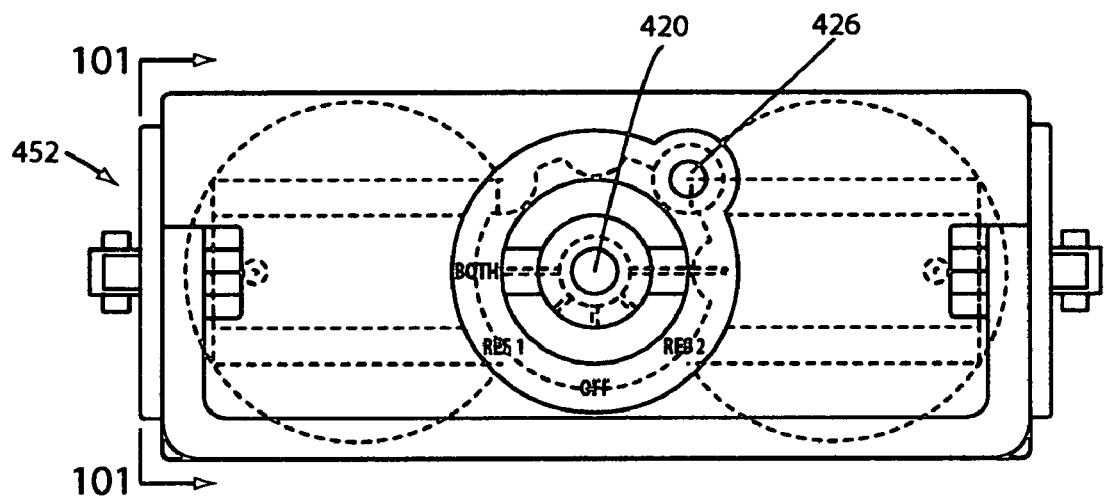
Figure 101:
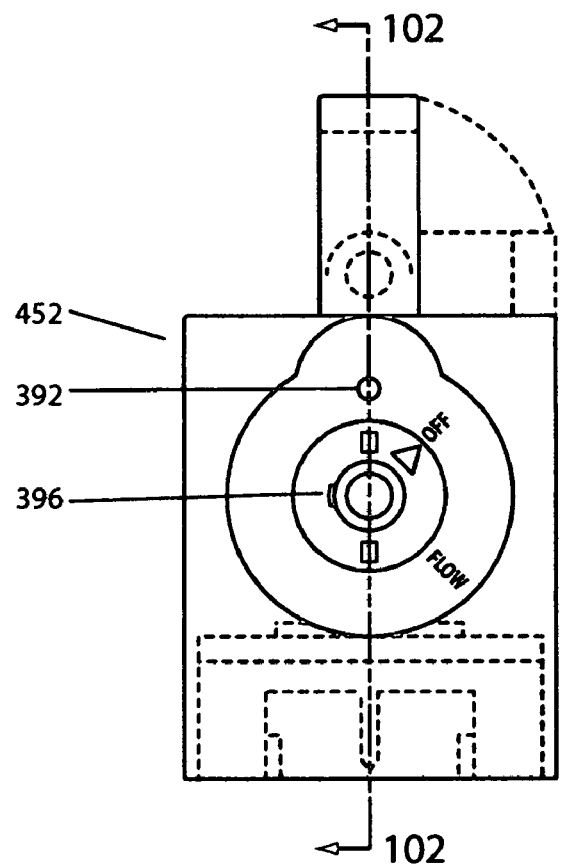

During the fluid delivery step, any gases contained within the reservoir of the unitary fluid reservoir assembly 296 and the various fluid passageways are vented to atmosphere via vent port "V" and passageway 407 (FIG. 94A). Similarly, during the fluid delivery step, any gases contained within the reservoir of the unitary fluid reservoir assembly 298 and the various fluid passageways are vented to atmosphere via vent port "V-1" and passageway 409 (FIG. 94B).

Turning next to FIG. 110 of the drawings, yet another embodiment of the invention is there shown and generally designated by the numeral 500. This alternate form of dispensing apparatus is similar in many respects to the embodiment of the invention illustrated in FIGS. 94 through 109 and like numerals are used in FIGS. 110 through 114 to identify like components. The primary difference between this latest form of the invention and that shown in FIGS. 94 through 109, resides in the fact that the two unitary fluid reservoir assemblies are substantially identical in construction and operation. Additionally, the configuration of the fluid reservoirs of these assemblies is of a somewhat different configuration from the reservoir defining components 300 of the previously described embodiment. However, the fluid delivery and control assembly of this latest form of the invention is substantially identical in construction as to that previously described herein in connection with the embodiment of the invention illustrated in FIGS. 49 through 93. Accordingly, in FIGS. 110 through 114, the fluid delivery and control assembly is designated as 452.

As in the embodiment of the invention illustrated in FIGS. 94 through 109, fluid is delivered to the patient at a fixed rather than a variable rate, and the first and second rate control assemblies 460a and 460b are substantially identical in construction and operation to those previously described in connection with the embodiment of the invention illustrated in FIGS. 94 through 109. Similarly, the rate control shafts as well as the reservoir selector means of the fluid delivery and control assembly are substantially identical in construction and operation to those previously described in connection with the embodiment of the invention illustrated in FIGS. 94 through 109.

As illustrated in FIGS. 111 through 114, each of the unitary fluid reservoir assemblies 502 comprises a generally cylindrically shaped housing 504 that houses the fluid reservoir 506 and the stored energy means (FIG. 111). Housing 504 includes a base 504a, an outer wall 504b and a top wall 504c. Connected to top wall 504c is a connector neck 510 within which a piercable septum 512 is mounted. As depicted in FIG. 111, connector neck 510 is initially closed by a sterile barrier 514 that is similar to sterile barrier 64a and is removably connected to the connector neck.

Disposed within reservoir 506 for movement there within between a first position shown in the upper portion of FIG. 110 and a second advanced position shown in the lower portion of FIG. 110 is a plunger assembly 516. Plunger assembly 516 includes a head portion 516a that sealably engages the walls of reservoir 506 and a stem portion 516b. In addition to pusher assembly 516, each assembly 502 includes a stored energy means that is operably associated with the pusher assembly for moving the pusher assembly between the first position and the second advanced position. The stored energy means of both of the assemblies 502 uniquely comprises a constant force spring 520 that is mounted within each of the housings 504 in the manner shown in FIG. 110. Constant force springs such as springs 520 are a special variety of extension spring. They comprise a pair of tightly coiled wound bands 520a of pre-hardened spring steel or stainless steel strip with built-in curvature so that each turn of the strip wraps tightly on its inner neighbor. When the strip is extended (deflected), the inherent stress resists the loading force, the same as a common extension spring but at a nearly constant (zero) rate. The constant-force spring is well suited to long extensions with no load build-up. As illustrated in FIGS. 110 and 111, springs 520 are mounted with each end thereof tightly wrapped on drums 522 that are housed with a mounting block 524 that forms a part of housing 504. The central portion 520b of each spring engages the stem portion 516b of each of the pusher assemblies so that as the spring contracts in the manner shown in the lower portion of FIG. 110, the pusher assembly will be controllably moved toward its second advanced position.

As best seen in FIG. 111, mounted on base 504a of each housing 504 is a threaded locking member 527 that threadably engages a locking block 530 that releasably locks spring 520 in an extended position in the manner illustrated in FIG. 111. When the locking member 527 is rotated from the first position shown in the upper portion of FIG. 110 to the second position shown in the lower portion of FIG. 110, the locking block 530 will be released allowing the spring to move toward its retracted position causing the plunger assembly to move toward its second advanced position as seen in the lower portion of FIG. 110.

In this latest form of the invention the fluid medicament reservoir 506 of each of the fluid reservoir assemblies is accessible via the previously identified penetrating members 304 and 306 which form the inlet to the fluid delivery and control assembly 452. More particularly, when the reservoir assemblies 502 are mated with the fluid delivery and control assembly, penetrating members 304 and 306 are adapted to pierce the pierceable septa 512 of the reservoir assemblies in the manner illustrated in FIG. 110 so as to permit fluid flow from the reservoirs 506 toward the rate control assemblies 460a and 460b.

With both the unitary reservoir assemblies 502 interconnected with the fluid delivery and control assembly 452 in the manner shown in FIG. 110, the first and second rate control shafts 458a and 458b of the control assembly of the invention can be operated in the manner previously described to permit fluid flow from the rate control assemblies toward the selector means of the invention and on toward the patient at a predetermined rate of flow.

Having now described the invention in detail in accordance with the requirements of the patent statues, those skilled in this art will have no difficulty in making changes and modifications in the individual parts or their relative assembly in order to meet specific requirements or conditions. Such changes and modifications may be made without departing from the scope and spirit of the invention, as set forth in the following claims:

I claim:

1. An apparatus for dispensing fluids to a patient comprising:
   (a) a fluid delivery and control assembly having a fluid outlet and comprising:
      (i) a body having first and second spaced apart chambers;
      (ii) a selector assembly connected to said body, said selector assembly having a fluid passageway in communication with said fluid outlet and being movable relative to said body from a first position wherein said fluid passageway is in communication with said first chamber and a second position where said fluid passageway is in communication with said second chamber; and
   (b) a first stand alone unitary reservoir unit having a threaded neck portion threadably received within said first chamber of said body of said fluid delivery and control assembly for communication with said fluid passageway of said selector assembly, said first unitary reservoir unit comprising a first housing having a first reservoir for containing a fluid and a first stored energy means for controllably urging said fluid from said first reservoir;
   (c) a second stand alone unitary reservoir unit having a threaded neck portion threadably received within said second chamber of said body of said fluid delivery and control assembly for communication with said fluid passageway of said selector assembly, said second unitary reservoir unit comprising a second housing having a second reservoir for containing a fluid and a second stored energy means for controllably urging said fluid from said second reservoir;

(d) a first rate control assembly connected to said body for controlling the rate of fluid flow from said first unitary reservoir unit toward said fluid outlet, said first rate control assembly comprising:
  (i) a first rate control plate having a plurality of fluid micro-channels; and
  (ii) a first rate control shaft in communication with said rate control plate, said first rate control shaft having a central bore and a plurality of radially extending passageways; and (e) a second rate control assembly connected to said body for controlling the rate of fluid flow from said second unitary reservoir unit toward said fluid outlet, said second rate control assembly comprising:
  (i) a second rate control plate having a plurality of fluid micro-channels; and
  ii) a second rate control shaft in communication with said rate control plate, said second rate control shaft having a central bore and a plurality of radially extending passageways.

2. The apparatus as defined in claim 1 in which said first unitary reservoir unit further includes a pusher member operably associated with said first stored energy means of said first unitary reservoir unit for controllably urging fluid from said first reservoir.

3. The apparatus as defined in claim 1 in which each of said first and second reservoirs is defined by an integrally formed, hermetically sealed collapsible container.

4. The apparatus as defined in claim 3 in which each of said collapsible containers includes a front portion, a rear portion and a collapsible accordion-like, continuous, uninterrupted side wall that interconnects said front and rear portions, said front portion of said collapsible container including a closure wall and said rear portion of said collapsible container including an inwardly extending ullage segment.

5. The apparatus as defined in claim 4 in which said first unitary reservoir unit further includes a carriage housed within said first housing, said carriage being operably associated with said collapsible container of said first unitary reservoir unit and with said first stored energy means and being movable by said first stored energy means from a first retracted position to a second advanced position.

6. The apparatus as defined in claim 4 in which said fluid delivery and control assembly further includes a first penetrating member disposed within said first chamber for piercing said closure wall of said collapsible container of said first unitary reservoir unit and a second penetrating member disposed within said second chamber for piercing said closure wall of said collapsible container of said second unitary reservoir unit.

7. The apparatus as defined in claim 4 in which said storage energy means comprises a spring.

8. The apparatus as defined in claim 4 in which said stored energy means comprises a constant force spring.

9. An apparatus for dispensing fluids to a patient comprising:
  (a) a fluid delivery and control assembly having a fluid outlet and comprising:
    (i) a body;
    (ii) a first rate control assembly connected to said body for controlling the rate of fluid flow toward said fluid outlet, said first rate control assembly comprising a first rate control plate having at least one micro-channel and a first rate control shaft in communication with said first rate control plate, said first rate control shaft having a central bore and a plurality of radially extending passageways;
    (iii) a second rate control assembly connected to said body for controlling the rate of fluid flow toward said fluid outlet, said second rate control assembly comprising a second rate control plate having at least one micro-channel and a second rate control shaft in communication with said second rate control plate, said second rate control shaft having a central bore and a plurality of radially extending passageways;
    (iv) a selector assembly connected to said body, said selector assembly being in communication with said fluid outlet and being movable relative to said body from a first position where said fluid outlet is in communication with said first rate control assembly and a second position where said fluid outlet is in communication with said second rate control assembly, said selector assembly comprising a selector knob having a head portion and a shaft portion, said shaft portion having an axially extending outlet passageway and a plurality of longitudinally-spaced, radially extending fluid passageways in communication with said axially extending outlet passageway; and
  (b) a first unitary reservoir unit connected to said body of said fluid delivery and control assembly for communication with said first rate control assembly, said first unitary reservoir unit comprising a first collapsible container for containing a medicinal fluid and first stored energy means for controllably collapsing said first collapsible container; and
  (c) a second unitary reservoir unit connected to said body of said fluid delivery and control assembly for communication with said second rate control assembly, said second unitary reservoir unit comprising a second collapsible container for containing a medicinal fluid and second stored energy means for controllably collapsing said second collapsible container.

10. The apparatus as defined in claim 9 in which each of said collapsible containers comprises an integrally formed, hermetically sealed collapsible container having a front portion, a rear portion and a collapsible accordion-like, continuous, uninterrupted side wall that interconnects said front and rear portions, said front portion of said collapsible container including a closure wall and said rear portion of said collapsible container including an inwardly extending ullage segment.

11. The apparatus as defined in claim 9 in which said first storage energy means comprises a spring.

12. The apparatus as defined in claim 9 in which said second stored energy means comprises a constant force spring.

13. An apparatus for dispensing fluids to a patient comprising:
  (a) a fluid delivery and control assembly having a fluid outlet and comprising:
    (i) a body;
    (ii) a first rate control assembly connected to said body for controlling the rate of fluid flow toward said fluid outlet, said first rate control assembly comprising a first rate control plate having a plurality of micro-channels formed therein, each said micro-channel having a different channel length, depth and width; and a first rate control shaft in communication with said first rate control plate, said first rate control shaft having a central bore and a plurality of radially extending fluid passageways;
(iii) a second rate control assembly connected to said body for controlling the rate of fluid flow toward said fluid outlet said second rate control assembly comprising a rate control plate having a plurality of micro-channels formed therein, each said micro-channel having a different channel length, depth and width; and a second rate control shaft in communication with said second rate control plate, said second rate control shaft having a central bore and a plurality of radially extending fluid passageways;
(iv) a selector assembly connected to said body, said selector assembly being in communication with said fluid outlet and being movable relative to said body from a first position where said fluid outlet is in communication with said first rate control assembly and a second position where said fluid outlet is in communication with said second rate control assembly;
(b) a first unitary reservoir unit threadably connected to said body of said fluid delivery and control assembly for communication with said first rate control assembly, said first unitary reservoir unit comprising:
(i) a first housing;
(ii) a first reservoir defining assembly comprising an integrally formed, hermetically sealed collapsible container mounted within said first housing, said first collapsible container having a front portion, a rear portion and a collapsible accordion-like, continuous, uninterrupted side wall that interconnects said front and rear portions, said front portion of said first collapsible container including a closure wall and said rear portion of said first collapsible container including an inwardly extending ullage segment, said first reservoir defining assembly further comprising a pierceable membrane positioned over said closure wall and a closure cap positioned over said pierceable membrane and secured to said collapsible container; and
(iii) a first spring mounted within said housing for controllably collapsing said first collapsible container; and
(c) a second unitary reservoir unit threadably connected to said body of said fluid delivery and control assembly for communication with said second rate control assembly, said second unitary reservoir unit comprising:
(i) a second housing;
(ii) a second reservoir defining assembly comprising an integrally formed, hermetically sealed collapsible container mounted within said second housing for containing a fluid, said second collapsible container having a front portion, a rear portion and a collapsible accordion-like, continuous, uninterrupted side wall that interconnects said front and rear portions, said front portion of said second collapsible container including a closure wall and said rear portion of said second collapsible container including an inwardly extending ullage segment, said second reservoir defining assembly further comprising a pierceable membrane positioned over said closure wall and a closure cap positioned over said pierceable membrane and secured to said collapsible container; and
(iii) a second spring mounted within said housing for controllably collapsing said second collapsible container.

* * * * *